United States Patent
Zhi et al.

(10) Patent No.: US 12,319,651 B2
(45) Date of Patent: Jun. 3, 2025

(54) CRYSTALLINE FORMS AND METHODS OF PRODUCING CRYSTALLINE FORMS OF A COMPOUND

(71) Applicant: Ligand Pharmaceuticals Incorporated, Emeryville, CA (US)

(72) Inventors: Lin Zhi, Austin, TX (US); Henri Sasmor, San Diego, CA (US)

(73) Assignee: Ligand Pharmaceuticals Incorporated, San Diego, CA (US)

( * ) Notice: Subject to any disclaimer, the term of this patent is extended or adjusted under 35 U.S.C. 154(b) by 831 days.

(21) Appl. No.: 17/604,729

(22) PCT Filed: Apr. 16, 2020

(86) PCT No.: PCT/US2020/028550
§ 371 (c)(1),
(2) Date: Oct. 18, 2021

(87) PCT Pub. No.: WO2020/214834
PCT Pub. Date: Oct. 22, 2020

(65) Prior Publication Data
US 2022/0204448 A1    Jun. 30, 2022

Related U.S. Application Data

(60) Provisional application No. 62/836,517, filed on Apr. 19, 2019.

(51) Int. Cl.
C07D 207/08    (2006.01)
(52) U.S. Cl.
CPC ........ *C07D 207/08* (2013.01); *C07B 2200/13* (2013.01)
(58) Field of Classification Search
CPC .................................................. C07D 207/08
See application file for complete search history.

(56) References Cited

U.S. PATENT DOCUMENTS

| | | |
|---|---|---|
| 3,710,795 A | 1/1973 | Higuchi et al. |
| 3,847,988 A | 11/1974 | Gold |
| RE28,819 E | 5/1976 | Thompson |
| 4,044,126 A | 8/1977 | Cook et al. |
| 4,097,578 A | 6/1978 | Perronnet et al. |
| 4,202,895 A | 5/1980 | Inaba et al. |
| 4,231,938 A | 11/1980 | Monaghan et al. |
| 4,294,926 A | 10/1981 | Monaghan et al. |
| 4,319,039 A | 3/1982 | Albers-Schonberg |
| 4,328,245 A | 5/1982 | Yu et al. |
| 4,346,227 A | 8/1982 | Terahara et al. |
| 4,358,603 A | 11/1982 | Yu |
| 4,364,923 A | 12/1982 | Cook et al. |
| 4,409,239 A | 10/1983 | Yu |
| 4,410,545 A | 10/1983 | Yu et al. |
| 4,410,629 A | 10/1983 | Terahara et al. |
| 4,414,209 A | 11/1983 | Cook et al. |
| 4,444,784 A | 4/1984 | Hoffman et al. |
| 4,522,811 A | 6/1985 | Eppstein et al. |
| 4,537,859 A | 8/1985 | Terahara et al. |
| 4,636,505 A | 1/1987 | Tucker |
| 4,681,893 A | 7/1987 | Roth |
| 4,729,999 A | 3/1988 | Young |
| 4,761,406 A | 8/1988 | Flora et al. |
| 4,782,084 A | 11/1988 | Vyas et al. |
| 4,820,850 A | 4/1989 | Verhoeven et al. |
| 4,876,248 A | 10/1989 | Breliere et al. |
| 4,885,314 A | 12/1989 | Vyas et al. |
| 4,894,373 A | 1/1990 | Young |
| 4,911,165 A | 3/1990 | Lennard et al. |
| 4,916,239 A | 4/1990 | Treiber |
| 4,927,814 A | 5/1990 | Gall et al. |
| 4,929,437 A | 5/1990 | Tobert |
| 4,970,335 A | 11/1990 | Isomura et al. |
| 4,981,784 A | 1/1991 | Evans et al. |
| 5,030,447 A | 7/1991 | Joshi et al. |
| 5,033,252 A | 7/1991 | Carter |
| 5,052,558 A | 10/1991 | Carter |
| 5,071,773 A | 12/1991 | Evans et al. |
| 5,118,853 A | 6/1992 | Lee et al. |
| 5,177,080 A | 1/1993 | Angerbauer et al. |
| 5,180,589 A | 1/1993 | Joshi et al. |
| 5,189,164 A | 2/1993 | Kapa et al. |
| 5,204,350 A | 4/1993 | Egbertson et al. |

(Continued)

FOREIGN PATENT DOCUMENTS

| | | |
|---|---|---|
| CL | 3237-2005 | 4/2006 |
| CL | 1709-2007 | 11/2007 |

(Continued)

OTHER PUBLICATIONS

Abdallah et al. STN Accession No. 1983:611894 Document No. 99:211894, Abstract of Journal of the Chemical Society, Perkin Transactions 2: Physical Organic Chemistry (1972-1999) (1983),(8):1243-9.

Abela Medici et al., "Cytotoxic compounds. Part 21. Chloro-, methoxy-, and methoxycarbonylderivatives of (bis-2-chloroethylamino)-phenols and -anilines," Journal of the Chemical Society, Perkin Transactions 1, Organic and Bio-organic Chemistry, 20:2258-2263, (1977).

Adams et al., "Time course of myosin heavy chain transitions in neonatal rats: importance of innervation and thyroid state," Am. J. Physiol. 276(4 Pt 2): R954-961 (1999).

Adesanya et al., "Sex steroid induced changes on the morphology of prostate of sprague-dawley rats," Sci. Res. Essays 2(8):309-314 (2007).

(Continued)

*Primary Examiner* — John S Kenyon
*Assistant Examiner* — Rehana Ismail
(74) *Attorney, Agent, or Firm* — Knobbe, Martens, Olson & Bear, LLP

(57) ABSTRACT

Disclosed herein are methods of crystallizing the compound of Formula (I), as well as crystalline forms thereof. Crystalline forms of Formula (I) disclosed include crystalline Form C, crystalline Form E, and Crystalline form B.

22 Claims, 10 Drawing Sheets

(56) References Cited

U.S. PATENT DOCUMENTS

| | | |
|---|---|---|
| 5,217,994 A | 6/1993 | Egbertson et al. |
| 5,273,995 A | 12/1993 | Roth |
| 5,278,034 A | 1/1994 | Ohki et al. |
| 5,290,946 A | 3/1994 | Lee et al. |
| 5,323,907 A | 6/1994 | Kalvelage |
| 5,342,952 A | 8/1994 | Butler et al. |
| 5,354,772 A | 10/1994 | Kathawala |
| 5,356,896 A | 10/1994 | Kabadi et al. |
| 5,393,763 A | 2/1995 | Black et al. |
| 5,489,961 A | 3/1996 | Butler et al. |
| 5,501,969 A | 3/1996 | Hastings et al. |
| 5,506,102 A | 4/1996 | McDonnell |
| 5,510,517 A | 4/1996 | Dauer et al. |
| 5,576,324 A | 11/1996 | Kyotani et al. |
| 5,639,754 A | 6/1997 | Heeres et al. |
| 5,648,491 A | 7/1997 | Dauer et al. |
| 5,677,336 A | 10/1997 | Jones et al. |
| 5,688,808 A | 11/1997 | Jones et al. |
| 5,688,810 A | 11/1997 | Jones et al. |
| 5,693,646 A | 12/1997 | Jones et al. |
| 5,696,130 A | 12/1997 | Jones et al. |
| 5,696,133 A | 12/1997 | Jones et al. |
| 5,710,159 A | 1/1998 | Voss et al. |
| 5,723,480 A | 3/1998 | Gante et al. |
| 5,736,357 A | 4/1998 | Bromme et al. |
| 5,741,796 A | 4/1998 | Hartman et al. |
| 5,760,028 A | 6/1998 | Jadhav et al. |
| 5,773,644 A | 6/1998 | Chen et al. |
| 5,773,646 A | 6/1998 | Chandrakumar et al. |
| 5,780,426 A | 7/1998 | Palladino et al. |
| 5,843,906 A | 12/1998 | Chandrakumar et al. |
| 5,852,210 A | 12/1998 | Chen et al. |
| 5,919,792 A | 7/1999 | Duggan et al. |
| 5,925,655 A | 7/1999 | Duggan et al. |
| 5,929,120 A | 7/1999 | Hartman et al. |
| 5,952,281 A | 9/1999 | Mondin et al. |
| 5,952,341 A | 9/1999 | Duggan et al. |
| 5,981,546 A | 11/1999 | Duggan et al. |
| 6,008,213 A | 12/1999 | Bondinell et al. |
| 6,017,924 A | 1/2000 | Edwards et al. |
| 6,017,925 A | 1/2000 | Duggan |
| 6,017,926 A | 1/2000 | Askew et al. |
| 6,028,223 A | 2/2000 | Ruminski et al. |
| 6,040,311 A | 3/2000 | Duggan et al. |
| 6,048,861 A | 4/2000 | Askew et al. |
| 6,066,648 A | 5/2000 | Duggan et al. |
| 6,069,158 A | 5/2000 | Miller et al. |
| 6,159,964 A | 12/2000 | Ali et al. |
| 6,358,947 B1 | 3/2002 | Zhi et al. |
| 6,380,207 B2 | 4/2002 | Coghlan et al. |
| 6,437,167 B1 | 8/2002 | Sunjic et al. |
| 6,444,642 B1 | 9/2002 | Sklar et al. |
| 6,462,038 B1 | 10/2002 | Higuchi et al. |
| 6,489,333 B2 | 12/2002 | Pitts et al. |
| 6,492,554 B2 | 12/2002 | Dalton et al. |
| 6,506,766 B1 | 1/2003 | Coghlan et al. |
| 6,534,516 B1 | 3/2003 | Edwards et al. |
| 6,566,372 B1 | 5/2003 | Zhi et al. |
| 6,569,896 B2 | 5/2003 | Dalton et al. |
| 6,596,298 B2 | 7/2003 | Leung et al. |
| 6,622,729 B1 | 9/2003 | Peyman |
| 6,630,128 B1 | 10/2003 | Love et al. |
| 6,667,313 B1 | 12/2003 | Hamann et al. |
| 6,670,386 B2 | 12/2003 | Sun et al. |
| 6,673,799 B1 | 1/2004 | Taniguchi et al. |
| 6,696,459 B1 | 2/2004 | Jones et al. |
| 6,710,066 B2 | 3/2004 | Kennedy et al. |
| 6,723,750 B2 | 4/2004 | Voet |
| 6,777,427 B2 | 8/2004 | Miyakawa et al. |
| 6,784,190 B2 | 8/2004 | Askew et al. |
| 6,806,284 B1 | 10/2004 | Moser |
| 6,838,484 B2 | 1/2005 | Steiner et al. |
| 6,845,378 B1 | 1/2005 | Pauly et al. |
| 6,899,888 B2 | 5/2005 | Steiner et al. |
| 6,960,474 B2 | 11/2005 | Salvati et al. |
| 6,964,973 B2 | 11/2005 | Zhi et al. |
| 6,995,284 B2 | 2/2006 | Dalton et al. |
| 6,998,500 B2 | 2/2006 | Dalton et al. |
| 7,011,812 B1 | 3/2006 | Griffiths |
| 7,012,075 B2 | 3/2006 | Prasit et al. |
| 7,018,395 B2 | 3/2006 | Chen |
| 7,018,993 B2 | 3/2006 | Ohta |
| 7,022,870 B2 | 4/2006 | Dalton et al. |
| 7,026,484 B2 | 4/2006 | Zhi et al. |
| 7,026,500 B2 | 4/2006 | Dalton |
| 7,037,888 B1 | 5/2006 | Sklar et al. |
| 7,037,919 B1 | 5/2006 | Hanada et al. |
| 7,053,263 B2 | 5/2006 | Sawyers et al. |
| 7,056,909 B2 | 6/2006 | Wang |
| 7,067,116 B1 | 6/2006 | Bess et al. |
| 7,074,930 B2 | 7/2006 | Wells et al. |
| 7,112,589 B2 | 9/2006 | Altmann et al. |
| 7,138,426 B2 | 11/2006 | DiNinno et al. |
| 7,151,196 B2 | 12/2006 | Wilkening et al. |
| 7,153,862 B2 | 12/2006 | Askew et al. |
| 7,157,604 B2 | 1/2007 | Meng et al. |
| 7,169,772 B2 | 1/2007 | Koshio et al. |
| 7,182,964 B2 | 2/2007 | Kupper et al. |
| 7,186,838 B2 | 3/2007 | Meissner et al. |
| 7,196,076 B2 | 3/2007 | Coleman et al. |
| 7,205,437 B2 | 4/2007 | Dalton et al. |
| 7,214,690 B2 | 5/2007 | Higuchi et al. |
| 7,214,693 B2 | 5/2007 | Dalton et al. |
| 7,214,804 B2 | 5/2007 | Zhai et al. |
| 7,217,720 B2 | 5/2007 | Meissner et al. |
| 7,220,736 B2 | 5/2007 | Yamada et al. |
| 7,241,411 B2 | 7/2007 | Berry |
| 7,241,753 B2 | 7/2007 | Loria |
| 7,253,210 B2 | 8/2007 | Dalton et al. |
| 7,268,153 B2 | 9/2007 | Hanney et al. |
| 7,268,232 B2 | 9/2007 | Schlienger et al. |
| 7,279,472 B2 | 10/2007 | Emmanuel et al. |
| 7,279,478 B2 | 10/2007 | Boyd et al. |
| 7,288,553 B2 | 10/2007 | Lanter et al. |
| 7,291,673 B2 | 11/2007 | Hubbell et al. |
| 7,301,026 B2 | 11/2007 | Tan et al. |
| 7,649,001 B2 | 1/2010 | Shiraishi et al. |
| 7,696,246 B2 | 4/2010 | Zhi et al. |
| 7,727,980 B2 | 6/2010 | Zhi et al. |
| 7,816,372 B2 | 10/2010 | Zhi et al. |
| 8,354,446 B2 | 1/2013 | Zhi |
| 8,519,158 B2 | 8/2013 | Zhi et al. |
| 8,748,063 B2 | 6/2014 | Zhi |
| 8,748,633 B2 | 6/2014 | Zhi |
| 8,865,918 B2 | 10/2014 | Zhi et al. |
| 9,139,520 B2 | 9/2015 | Zhi |
| 9,359,285 B2 | 6/2016 | Zhi et al. |
| 9,675,583 B2 | 6/2017 | Zhi |
| 10,106,500 B2 | 10/2018 | Zhi |
| 10,730,831 B2 | 8/2020 | Zhi |
| 11,358,931 B2 | 6/2022 | Zhi |
| 2002/0022621 A1 | 2/2002 | Chaturvedula et al. |
| 2002/0025955 A1 | 2/2002 | Han et al. |
| 2002/0183314 A1 | 12/2002 | Higuchi et al. |
| 2002/0183346 A1 | 12/2002 | Zhi et al. |
| 2003/0055094 A1 | 3/2003 | Sun et al. |
| 2003/0114496 A1 | 6/2003 | Churcher et al. |
| 2003/0130505 A1 | 7/2003 | Zhi et al. |
| 2003/0149268 A1 | 8/2003 | Hamann et al. |
| 2003/0186970 A1 | 10/2003 | Higuchi et al. |
| 2003/0212070 A1 | 11/2003 | Schwink et al. |
| 2005/0288350 A1 | 12/2005 | Zhi et al. |
| 2006/0111441 A1 | 5/2006 | Dalton et al. |
| 2007/0066650 A1 | 3/2007 | Zhi et al. |
| 2007/0293528 A9 | 12/2007 | Zhi et al. |
| 2008/0300241 A9 | 12/2008 | Higuchi et al. |
| 2009/0203725 A1 | 8/2009 | Van Oeveren et al. |
| 2009/0227571 A1 | 9/2009 | Loren et al. |
| 2009/0264455 A9 | 10/2009 | Pedram et al. |
| 2010/0069379 A1 | 3/2010 | Zhi et al. |

(56) References Cited

U.S. PATENT DOCUMENTS

| | | |
|---|---|---|
| 2010/0152236 A1 | 6/2010 | Yamamoto et al. |
| 2010/0210678 A1 | 8/2010 | Zhi et al. |
| 2012/0004220 A9 | 1/2012 | Zhi |

FOREIGN PATENT DOCUMENTS

| | | |
|---|---|---|
| EP | 0 638 571 | 2/1995 |
| EP | 0 711 768 | 5/1996 |
| EP | 1 122 242 | 8/2001 |
| EP | 0 800 519 | 10/2003 |
| EP | 2 222 636 | 9/2010 |
| EP | 2 489 656 | 8/2012 |
| GB | 1177545 | 1/1970 |
| JP | 2002-088073 A | 3/2002 |
| WO | WO 95/11215 | 4/1995 |
| WO | WO 95/031722 | 11/1995 |
| WO | WO 96/019458 | 6/1996 |
| WO | WO 97/049709 | 12/1997 |
| WO | WO 98/022432 | 5/1998 |
| WO | WO 98/28268 | 7/1998 |
| WO | WO 99/67221 | 12/1999 |
| WO | WO 00/07995 | 2/2000 |
| WO | WO 00/38618 | 7/2000 |
| WO | WO 00/44777 | 8/2000 |
| WO | WO 00/50391 | 8/2000 |
| WO | WO 00/61186 | 10/2000 |
| WO | WO 00/066590 | 11/2000 |
| WO | WO 01/02235 | 1/2001 |
| WO | WO 01/16108 | 3/2001 |
| WO | WO 01/016133 | 3/2001 |
| WO | WO 01/016139 | 3/2001 |
| WO | WO 01/19797 | 3/2001 |
| WO | WO 01/027086 | 4/2001 |
| WO | WO 01/27091 | 4/2001 |
| WO | WO 01/027107 | 4/2001 |
| WO | WO 01/27108 | 4/2001 |
| WO | WO 01/34571 | 5/2001 |
| WO | WO 01/34639 | 5/2001 |
| WO | WO 01/49288 | 7/2001 |
| WO | WO 01/53255 | 7/2001 |
| WO | WO 01/60826 | 8/2001 |
| WO | WO 01/66564 | 9/2001 |
| WO | WO 01/70677 | 9/2001 |
| WO | WO 01/74783 | 10/2001 |
| WO | WO 01/74784 | 10/2001 |
| WO | WO 01/74796 | 10/2001 |
| WO | WO 01/77073 | 10/2001 |
| WO | WO 01/77086 | 10/2001 |
| WO | WO 01/77144 | 10/2001 |
| WO | WO 01/83460 | 11/2001 |
| WO | WO 01/90084 | 11/2001 |
| WO | WO 01/92235 | 12/2001 |
| WO | WO 02/16310 | 2/2002 |
| WO | WO 02/022585 | 3/2002 |
| WO | WO 02/30912 | 4/2002 |
| WO | WO 02/36555 | 5/2002 |
| WO | WO 02/47671 | 6/2002 |
| WO | WO 02/057252 | 7/2002 |
| WO | WO 02 066475 | 8/2002 |
| WO | WO 02/068427 | 9/2002 |
| WO | WO 02/081433 | 10/2002 |
| WO | WO 02/081435 | 10/2002 |
| WO | WO 03/011824 | 2/2003 |
| WO | WO 03/018543 | 3/2003 |
| WO | WO 03/037905 | 5/2003 |
| WO | WO 03/042181 | 5/2003 |
| WO | WO 03/049675 | 6/2003 |
| WO | WO 03/090672 | 11/2003 |
| WO | WO 04/016576 | 2/2004 |
| WO | WO 05/000795 | 1/2005 |
| WO | WO 05/090282 | 9/2005 |
| WO | WO 05/108351 | 11/2005 |
| WO | WO 06/064944 | 6/2006 |
| WO | WO 06/124447 | 11/2006 |
| WO | WO 06/138347 | 12/2006 |
| WO | WO 07/015567 | 2/2007 |
| WO | WO 07/075884 | 7/2007 |
| WO | WO 07/145349 | 12/2007 |
| WO | WO-2009082437 A2 * | 7/2009 ........... A61K 31/401 |
| WO | WO 09/082437 | 9/2009 |
| WO | WO 15/108988 | 7/2015 |
| WO | WO 20/214834 | 10/2020 |

OTHER PUBLICATIONS

Allan et al. "A selective androgen receptor modulator with minimal prostate hypertrophic activity enhances lean body mass in male rats and stimulates sexual behavior in female rats," Endocrine 32(1):41-51 (2007).

Allegretto et al., "Transactivation properties of retinoic acid and retinoid X receptors in mammalian cells and yeast. Correlation with hormone binding and effects of metabolism," J. Biol. Chem. 268(35):26625-26633 (1993).

American Society for Reproductive Medicine, "Sexual Dysfunction—Patient's Fact Sheet," 1 page (1998).

Ames et al., "Methods for detecting carcinogens and mutagens with the *Salmonella*/mammalian-microsome mutagenicity test," Mutation Res. 31(6):347-364 (1975).

Anderson et al., "Androgen supplementation in eugonadal men with osteoporosis-effects of 6 months of treatment on bone mineral density and cardiovascular risk factors," Bone 18(2):171-177 (1996).

Anlezark et al., "Bioactivation of dinitrobenzamide mustards by an *E. coli* B nitroreductase," Biochemical Pharmacology, 50:609-618, (1995).

Anastasiou et al. STN Accession No. 1994:605178, Document No. 121:205178, Abstract of Australian Journal of Chemistry (1994), 47(6), 1043-59. *.

Ansel, H.C., Introduction to Pharmaceutical Dosage Forms, Fourth Edition, Lea and Febiger, Philadelphia, P.A., p. 126, (1985).

Antonio et al., "Effects of castration and androgen treatment on androgen-receptor levels in rat skeletal muscles," J. Appl. Physiol. 87(6):2016-2019 (1999).

Arlt, "Dehydroepiandrosterone replacement in women with adrenal insufficiency," N. Engl. J. Med. 341(14):1013-1020 (1999).

Arlt, W., "Androgen therapy in women," Eur. J. Endocrinol. 154(1):1-11 (2006).

Arriza et al., "Cloning of human mineralocorticoid receptor complementary DNA: structural and functional kinship with the glucocorticoid receptor," Science 237(4812):268-275 (1987).

Ashby et al., "The peripubertal male rat assay as an alternative to the Hershberger castrated male rat assay for the detection of anti-androgens, oestrogens and metabolic modulators," J. Appl. Tox. 20(1):35-47 (2000).

Bains and Tacke, "Silicon chemistry as a novel source of chemical diversity in drug design," Current Opinion in Drug Discovery and Development, 6(4):526-543, (2003).

Balbach, et al., "Pharmaceutical evaluation of early development candidates 'The 100 mg-Approach,'" International Journal of Pharmaceutics, 275 (2004) 1-12.

Bandeen-Roche et al., "Phenotype of frailty: characterization in the women's health and aging studies," J. Gerontol. A: Biol. 61A(3):262-266 (2006).

Beers et al., Eds., "Chapter 52: Osteoarthritis and neurogenic arthropathy," in Merck Manual, 17th Edition, pp. 449-452 (1999).

Behre et al., "Long-term effect of testosterone therapy on bone mineral density in hypogonadal men," J. Clin. Endocrinol. Metabol. 82(8):2386-2390 (1997).

Bellido et al., "Regulation of interleukin-6, osteoclastogenesis, and bone mass by androgens. The role of the androgen receptor," J. Clin. Invest. 95(6):2886-2895 (1995).

Ben-Av et al., "Induction of vascular endothelial growth factor expression in synovial fibroblasts by prostaglandin E and interleukin-1: a potential mechanism for inflammatory angiogenesis," FEBS Lett. 372(1):83-87 (1995).

Benezra et al., "In vivo angiogenic activity of interleukins," Arch. Ophthalmol. 108:573-576 (1990).

(56) References Cited

OTHER PUBLICATIONS

Bentel et al., "Androgen receptor expression in primary prostate cancers of Lobund-Wistar rats and in tumor-derived cell lines," In Vitro Cell Dev. Biol. 35(10):655-662 (1999).
Beresford et al., "Formation of mineralized nodules by bone derived cells in vitro: a model of bone formation?" 45(2):163-178 (2005).
Berge et al., "Pharmaceutical salts," J. Pharm. Sci. 66(1):1-19 (1977).
Berger et al., "Interaction of glucocorticoid analogues with the human glucocorticoid receptor," Journal of Steroid Biochemistry and Molecular Biology, 41:733-748, (1992).
Berrevoets et al. Selective modulation of androgen receptor function, 12th International Congress of Endocrinology, 2004, p. 43-48.
Bhasin et al., "Testosterone replacement increases fat-free mass and muscle size in hypogonadal men," J. Clin. Endocrinol. Metabol. 82(2):407-413 (1997).
Bhasin et al., "Drug Insight: testosterone and selective androgen receptor modulators as anabolic therapies for chronic illness and aging," Nat. Clin. Pract. Endocrin. Metabol. 2(3):146-159 (2006).
Bhasin et al., "Proof of the effect of testosterone on skeletal muscle," J. Endocrinol. 170(1):27-38 (2001).
Bhasin et al., "The effects of supraphysiologic doses of testosterone on muscle size and strength in normal men," N. Engl. J. Med. 335(1):1-7 (1996).
Bijlsma et al., "Estrogens and rheumatoid arthritis," Am. J. Reprod. Immunol. 28(3-4):231-234 (1992).
Bissonnette et al., "9-cis Retinoic acid inhibition of activation-induced apoptosis is mediated via regulation of Fas ligand and requires retinoic acid receptor and retinoid X receptor activation," Mol. Cell Biol. 15(10):5576-5585 (1995).
Boehm et al., "Synthesis and structure-activity relationships of novel retinoid X receptor-selective retinoids," J. Med. Chem. 37(18):2930-2941 (1994).
Boudou et al., "Effect of oral isotretinoin treatment on skin androgen receptor levels in male acneic patients," J. Clin. Endocrinol. Metabol. 80(4):1158-1161 (1995).
Bouma et al., "Thrombin-activatable fibrinolysis inhibitor (TAFI, plasma procarboxypeptidase B, procarboxypeptidase R, procarboxypeptidase U," Thromb. Res. 101(5):329-354 (2001).
Box et al., "Correcting inhomogeneity of variance with power transformation weighting," Technometrics 16:385-389 (1974).
Box, G. and D. Cox, "An analysis of transformations," J. Roy. Stat. Soc. B 26:211-252 (1964).
Braga, Dario, "Crystal Polymorphism and Multiple Crystal Forms," Struct Bond (2009) 132:25-50.
Brady et al., "Depot testosterone with etonogestrel implants result in induction of azoospermia in all men for long-term contraception," Hum. Reprod. 19(11):2658-2667 (2004).
Brittain, et al., "Polymorphism in Pharmaceutical Solids," 1999 ISBN: 0-8247-0237-9, pp. 235-238 paragraph 2, p. 236.
Broulik, P. and L. Starka, "Effect of antiandrogens casodex and epitestosterone on bone composition in mice," Bone 20(5):473-475 (1997).
Brower, V., "Tumor angiogenesis: new drugs on the block," Nature Biotechnol. 17(10):963-968 (1999).
Brown, T., "Nonsteroidal selective androgen receptor modulators (SARMs): designer androgens with flexible structures provide clinical promise," Endocrinol. 145(12):5417-5419 (2004).
Buhler et al., "Intermittent androgen suppression in the LuCaP 23.12 prostate cancer xenograft model," The Prostate 43(1):63-70 (2000).
Buijsman et al., "Non-steroidal steroid receptor modulators," Curr. Med. Chem. 12(9):1017-1075 (2005).
Bundgaard et al., "A novel solution-stable, water-soluble prodrug type for drugs containing a hydroxyl or an NH-acidic group," J. Med. Chem. 32(12):2503-2507 (1989).
Cadilla et al., "Selective androgen receptor modulators in drug discovery: medicinal chemistry and therapeutic potential," Curr. Top. Med. Chem. 6(3):245-270 (2006).
Caira, "Crystalline Polymorphism of Organic Compounds," Topicvs in Current Chemistry, Springer, Berlin, DE (19980101), vol. 198, ISSN 0340-1022, pp. 163-208, 1998.
Carmina, "Ovarian and andrenal hyperandrogenism," Ann NY Acad Sci (2006) 1092:130-137.
Carnahan, R. and P. Perry, "Depression in aging men: the role of testosterone," Drugs Aging 21(6):361-376 (2004).
Cesario et al., "The rexinoid LG100754 is a novel RXR:P-PARgamma agonist and decreases glucose levels in vivo," Mol. Endocrinol. 15(8):1360-1369 (2001).
Chakraborty et al., "Developmental expression of the cyclo-oxygenase-1 and cyclo-oxegenase-2 genes in the peri-implantation mouse uterus and their differential regulation by the blastocyst and ovarian steroids," J. Mol. Endocrinol. 16:107-122 (1996).
Chan, S., "A review of selective estrogen receptor modulators in the treatment of breast and endometrial cancer," Semin Oncol. 29(3 Suppl 11):129-133 (2002).
Chen et al., "A selective androgen receptor modulator (SARM) for hormonal male contraception," JPET Fast Forward, JPET #75424, 46 pages (2004).
Chen et al., "A selective androgen receptor modulator for hormonal male contraception," J. Pharmacol. Exp. Ther. 312(2):546-553 (2005).
Chen et al., "Androgen-dependent and -independent human prostate xenograft tumors as models for drug activity evaluation," Cancer Res. 58(13):2777-2783 (1998).
Chen et al., "Discovery and therapeutic promise of selective androgen receptor modulators," Mol. Interv. 5(3):173-188 (2005).
Chen et al., "Testosterone inhibits osteoclast formation stimulated by parathyroid hormone through androgen receptor," FEBS Lett. 491(1-2):91-93 (2001).
Cheng, Y. and W. Prusoff, "Relationship between the inhibition constant (K1) and the concentration of inhibitor which causes 50 per cent inhibition (150) of an enzymatic reaction," Biochem. Pharmacol. 22(23):3099-3108 (1973).
Chiarugi et al., "Cox-2, iNOS and p53 as play-makers of tumor angiogenesis (review)," Int. J. Mol. Med. 2(6):715-719 (1998).
Chung, L., "LNCaP human prostate cancer progression model," Urol. Oncol. 2(4):126-128 (1996).
Corbould, A., "Chronic testosterone treatment induces selective insulin resistance in subcutaneous adipocytes of women," J. Endocrinol. 192(3):585-594 (2007).
Coxam et al., "Effects of dihydrotestosterone alone and combined with estrogen on bone mineral density, bone growth, and formation rates in ovariectomized rats," Bone 19(2):107-114 (1996).
Craft et al., "Evidence for clonal outgrowth of androgen-independent prostate cancer cells from androgen-dependent tumors through a two-step process," Cancer Res. 59(19):5030-5036 (1999).
Cutolo et al., "Androgens and estrogens modulate the immune and inflammatory responses in rheumatoid arthritis," Ann. N.Y. Acad. Sci. 966:131-142 (2002).
Cutolo, M., "Sex hormone adjuvant therapy in rheumatoid arthritis," Rheum. Dis. Clin. N. Am. 26(4):881-895 (2000).
Dalton et al. Drug Delivery Technology, Sep. 2004, 4(7), 54-60. *.
Davis, S., "Androgen replacement in women: a commentary," Clin. Endocrinol. Metab. 84:1886-1891 (1999).
Deaton, D. and F. Tavares, "Design of cathepsin K inhibitors for osteoporosis," Curr. Top. Med. Chem. 5(16):1639-1675 (2005).
Dei et al., "Synthesis and cholinergic affinity of diastereomeric and enantiomeric isomers of 1-methyl-2-(2-methyl-1,3-dioxolan-4-yl)-pyrrolidine, 1-methyl-2-(2-methyl-1,3-oxathiolan-5-yl)pyrrolidine and of their iodomethylates," Bioorg. Med. Chem. 11(14):3153-3164 (2003).
Deplewski et al., "Preputial sebocyte 5-reductase isoform specificity," Endocrinol. 138(10):4416-4420 (1997).
Devogelaer et al., "Low bone mass in hypogonadal males. Effect of testosterone substitution therapy, a densitometric study," Maturitas 15(1):17-23 (1992).
Dorwald F. A. (Side Reactions in Organic Synthesis, 2005, Wiley: VCH, Weinheim p. IX of Preface p. 1-15).
Eagleson et al., "Polycystic ovarian syndrome: evidence that flutamide restores sensitivity of the gonadotropin-releasing hormone pulse

(56) References Cited

OTHER PUBLICATIONS generator to inhibition by estradiol and progesterone," J. Clin. Endocrinol. Metab. 85(11): 4047-4052 (2000).
Edwards et al., "Nonsteroidal androgen receptor agonists based on 4-(trifluoromethyl)-2H-pyrano[3,2-g]quinolin-2-one," Bioorganic Medicine and Chemistry Letters, 9(7):1003-1008, (1999).
Edwards et al., "New nonsteroidal androgen receptor modulators based on 4-(trifluoromethyl)-2(1H)-pyrrolidino[3,2-g]quinolinone," Bioorg. Med. Chem. Lett. 8:745-750 (1998).
Eisenberg, E. and G. Gordan, "The levator ani muscle of the rat as an index of myotrophic activity of steroidal hormones," J. Pharmacol. Exp. Ther. 99(1):38-44 (1950).
Elslager et al., "Folate antagonists. 3. 2,4-Diamino-6-(heterocyclic)quinazolines, a novel class of antimetabolites with potent antimalarial and antibacterial activity," J. Med. Chem. 15(8):827-836 (1972).
Etreby et al., "Antitumor activity of mifepristone in the human LNCaP, LNCaP-C4, and LNCaP-C4-2 prostate cancer models in nude mice," The Prostate 42(2): 99-106 (2000).
Evans et al., "The steroid and thyroid hormone receptor superfamily," Science, 240:889-895, (1988).
Evans et al., "Ostarine increases lean body mass and improves physical performance in healthy elderly subjects: Implications for cancer cachexia patients," J. Clin. Oncol., 2007 ASCO Annual Meeting Proceedings (Post-Meeting Edition) vol. 25, No. 18S (Jun. 20 Supplement), Abstract #9119 (2007).
Fernandez et al., "Neovascularization produced by angiotensin II," J. Lab. Clin. Med. 105(2):141-145 (1985).
Ferrando et al., "Testosterone administration to older men improves muscle function: molecular and physiological mechanisms," Am. J. Physiol. Endocrinol. Metabol. 282(3):E601-E607 (2002).
Fine, S., "Erectile dysfunction and comorbid diseases, androgen deficiency, and diminished libido in men," J. Am. Osteopath. Assoc. 104(1 Supplement 1):S9-S15 (2004).
Fingl et al., The Pharmacological Basis of Therapeutics, Ch. 1, Eds. Goodman and Gilman, Macmillan Publishing Co., New York, N.Y., pp. 1-46, (1975).
Finkelstein et al., "Increases in bone density during treatment of men with idiopathic hypogonadotropic hypogonadism," J. Clin. Endocrinol. Metabol. 69(4):776-783 (1989).
Food and Drug Administration, "International conference on harmonization; guidance on specific aspects of regulatory genotoxicity tests for pharmaceuticals; availability; notice," Federal Register 61(80):18198-18202 (Apr. 24, 1996).
Food and Drug Administration, "International conference on harmonization; draft guideline on genotoxicity: a standard battery for genotoxicity testing of pharmaceuticals; notice," Federal Register 62(64):16026-16030 (Apr. 3, 1997).
Forman et al., "Identification of a nuclear receptor that is activated by farnesol metabolites," Cell 81(5):687-693 (1995).
Fujisaki et al., "Halogenation using N-halogenocompounds. I. Effect of amines on ortho bromination of phenols with NBS," Bull. Chem. Soc. Jpn. 66:1576-1579 (1993).
Fuller et al., "Androgens in the etiology of Alzheimer's disease in aging men and possible therapeutic interventions," J. Alzheimers Dis. 12(2):129-142 (2007).
Furr, "The development of Casodex (bicalutamide): preclinical studies," Eur. Urol. 29:83-95 (1996).
Furr, B. and H. Tucker, "The preclinical development of bicalutamide: pharmacodynamics and mechanism of action," Urology 47 (Suppl. 1A): 13-25 (1996).
Galloway et al., "Report from working group on in vitro tests for chromosomal aberrations," Mutat. Res. 312(3):241-261 (1994).
Gao et al., "Pharmacokinetics and pharmacodynamics of nonsteroidal androgen receptor ligands," Pharm. Res. 23(8):1641-1658 (2006).
Gao et al., "Selective androgen receptor modulator treatment improves muscle strength and body composition and prevents bone loss in orchidectomized rats," Endocrinol. 146(11):4887-4897 (2005).
Gao, W. and J. Dalton, "Expanding the therapeutic use of androgens via selective androgen receptor modulators (SARMs)," Drug Discov. Today 12(5-6):241-248 (2007).
Gerdes et al., "Transforming growth factor-betal induces nuclear to cytoplasmic distribution of androgen receptor and inhibits androgen response in prostate smooth muscle cells," Endocrinol. 139(8):3569-3577 (1998).
Ghosh et al., "A global model to define the behavior of partial agonists (bell-shaped dose-response inducers) in pharmacological evaluation of activity in the presence of the full agonist," J. Biopharm. Stat. 8(4):645-665 (1998).
Giguere et al., "Functional domains of the human glucocorticoid receptor," Cell 46:645-652 (1986).
Goldstein et al., "A pharmacological review of selective oestrogen receptor modulators," Hum. Reprod. Update 6(3):212-224 (2000).
Gonzalez-Cadavid et al., "Up-regulation of the levels of androgen receptor and its mRNA by androgens in smooth-muscle cells from rat penis," Mol. Cell. Endocrinol. 90(2):219-229 (1993).
Gooren et al., "Recent insights into androgen action on the anatomical and physiological substrate of penile erection," Asian J. Androl. 8(1):3-9 (2006).
Gouras et al., "Testosterone reduces neuronal secretion of Alzheimer's β-amyloid peptides," Proc. Nat. Acad. Sci. U.S.A. 97(3):1202-1205 (2000).
Gowen et al., "Antagonizing the parathyroid calcium receptor stimulates parathyroid hormone secretion and bone formation in osteopenic rats," J. Clin. Invest. 105(11):1595-1604 (2000).
Gravatt et al., "DNA-directed alkylating agents. 6. Synthesis and antitumor activity of DNA minor groove-targeted aniline mustard analogues of pibenzimol (Hoechst 33258)," Journal of Medicinal Chemistry 37:4338-4345, (1994).
Green et al., "Mutagen testing using TRP+ reversion in *Escherichia coli*," Mutat. Res. 38(1):3-32 (1976).
Gregory, et al., "Androgen Receptor Stabilization in Recurrent Prostate Cancer is Associated with Hypersensitivity to Low Androgen," Cancer Research (2001) 61:2892-2898.
Hamann et al., "Synthesis and biological activity of a novel series of nonsteroidal, peripherally selective androgen receptor antagonists derived from 1,2-dihydropyridono[5,6-g]quinolines," Journal of Medicinal Chemistry, 41(4):623-639, (1998).
Hammond et al., "Testosterone-mediated neuroprotection through the androgen receptor in human primary neurons," J. Neurochem. 77(5):1319-1326 (2001).
Hannon, R. and R. Eastell, "Bone markers and current laboratory assays," Cancer Treat. Rev. 32(Suppl 1):7-14 (2006).
Harada et al., "Expression and regulation of vascular endothelial growth factor in osteoblasts," Clin. Orthop. Relat. Res. 313:76-80 (1995).
Harris et al., "Nilutamide. A review of its pharmacodynamic and pharmacokinetic properties, and therapeutic efficacy in prostate cancer," Drugs and Aging 3:9-25 (1993).
Harris, K. and E. Small, "Hormonal treatment for prostate cancer," Expert Opin. Investig. Drugs 10(3):493-510 (2001).
Hasselgren et al., "Muscle wasting: current progress and future aims," Intl. J. Biochem. Cell Biol. 37:1932 (2005).
Harrowven et al., "A new cascade radical reaction for the synthesis of biaryls and triaryls from benzyl iodoaryl ethers," Tet. Lett. 42:961-964 (2001).
Hershberger et al., "Myotrophic activity of 19-nortestosterone and other steroids determined by modified levator ani muscle method," Proc. Soc. Exptl. Biol. Med. 83:175-178 (1953).
Higuchi et al., "4-Alkyl- and 3,4-dialkyl-1,2,3,4-tetrahydro-8-pyridono[5,6-g]quinolines potent, nonsteroidal androgen receptor agonists," Bioorganic Medicine and Chemistry Letters, 9(9):1335-1340, (1999).
Higuchi et al., "Potent, nonsteroidal selective androgen receptor modulators (SARMs) based on 8H-[1,4]oxazino[2,3-f]quinolin-8-ones," Bioorg. Med. Chem. Lett. 17:5442-5446 (2007).
Hilfker, Rolf, "Relevance of Solid-State Properties for Pharmaceutical Products," Polymorphism: in the Pharmaceutical Industry, 2006 pp. 1-19.

(56) References Cited

OTHER PUBLICATIONS

Hirayama, N., ed., Handbook of Organic Compound Crystal Preparation—Principles and Know-How, Maruzen Publishing Co., Ltd., Jul. 25, 2008, pp. 57-84.
Hla et al., "Human cyclooxygenase-2 cDNA," Proc. Natl. Acad. Sci. U.S.A. 89:7384-7388 (1992).
Hofbauer, L. and S. Khosla, "Androgen effects on bone metabolism: recent progress and controversies," Eur. J. Endocrinol. 140:271-286 (1999).
Hunter et al., "Biochemical markers of bone turnover and their association with bone marrow lesions," Arthritis Res. Ther. 10(4):R102, 8 pages (2008).
Ilio et al., "The primary culture of rat prostate basal cells," J. Androl. 19(6):718-724 (1998).
Ivaska et al., "Release of intact and fragmented osteocalcin molecules from bone matrix during bone resorption in vitro," J. Biol. Chem. 279(18):18361-18369 (2004).
Jackson et al., "Suppression of androgen receptor expression by dibenzoylmethane as a therapeutic objective in advanced prostate cancer," Anticancer Res. 27(3B):1483-1488 (2007).
Jansson, L. and R. Holmdahl, "Enhancement of collagen-induced arthritis in female mice by estrogen receptor blockage," Arthritis Rheum. 44(9):2168-2175 (2001).
Jasuja et al., "Delta-4-androstene-3,17-dione binds androgen receptor, promotes myogenesis in vitro, and increases serum testosterone levels, fat-free mass, and muscle strength in hypogonadal men," J. Clin. Endocrinol. Metabol. 90(2):855-863 (2005).
Jasuja et al., "Tetrahydrogestrinone is an androgenic steroid that stimulates androgen receptor-mediated, myogenic differentiation in C3H10T1/2 multipotent mesenchymal cells and promotes muscle accretion in orchidectomized male rats," Endocrinology 146(10):4472-4478 (2005).
Jilka et al., "Increased osteoclast development after estrogen loss: mediation by interleukin-6," Science 257(5066):88-91 (1992).
Jin et al., "Poled, chromophore-functionalized polymeric nonlinear optical materials. Probing second harmonic generation temporal characteristics via site-selective crosslinking/hydrogen bonding," Chem. Materials 4(5):963-965 (1992).
Jin et al., STN Document No. 117:151996, Abstract of Chemistry of Materials (1992) 4(5):963-5.
Johnson, S., "Premenstrual syndrome therapy," Clin. Obstet. Gynecol. 41(2):405-421 (1998).
Jones, "The structure, reactions, synthesis and uses of heterocyclic compounds," Comprehensive Heterocyclic Chemistry, vol. 2, Ch. 2, p. 421-426 (1984).
Jongsma et al., "Androgen deprivation of the prohormone convertase-310 human prostate cancer model system induces neuroendocrine differentiation," Cancer Res. 60:741-748 (2000).
Jongsma et al., "Kinetics of neuroendocrine differentiation in an androgen-dependent human prostate xenograft model," Amer. J. Path. 154(2):543-551 (1999).
Jordan, V., "Selective estrogen receptor modulation: A personal perspective," Cancer Res. 61:5683-5687 (2001).
Joseph et al., "Role of endocrine-immune dysregulation in osteoporosis, sarcopenia, frailty and fracture risk," Mol. Aspects Med. 26(3):181-201 (2005).
Kapil et al., "Phase I clinical trial of LGD-4033, a novel selective androgen receptor modulator (SARM)," 14th International Congress of Endocrinology, Kyoto, Japan, Mar. 26-30, 2010, 1 page [poster presentation].
Kang, et al., "Mechanisms and Clinical Relevance of Androgens and Androgen Receptor Actions," Chang Gung Med J (2003) 26(6):388-402.
Katznelson et al., "Increase in bone density and lean body mass during testosterone administration in men with acquired hypogonadism," J. Clin. Endocrinol. Metabol. 81(12):4358-4365 (1996).
Kawaguchi, Y., et al., Journal of Human Environmental Engineering, 2002, vol. 4, No. 2, pp. 310-317.
Kazmin et al., "Linking ligand-induced alterations in androgen receptor structure to differential gene expression: a first step in the rational design of selective androgen receptor modulators," Mol Endocrinol. 20(6):1201-1217 (2006).
Keller et al., "Inhibition of NFkappaB activity through maintenance of IkappaBalpha levels contributes to dihydrotestosterone-mediated repression of the interleukin-6 promoter," J. Biol. Chem. 271(42):26267-26275 (1996).
Kilbourne et al., "Selective androgen receptor modulators for frailty and osteoporosis," Curr. Opin. Investig. Drugs 8(10):821-829 (2007).
Kim et al., "Inhibition of vascular endothelial growth factor-induced angiogenesis suppresses tumour growth in vivo," Nature 362(6423):841-844 (1993).
Kingsberg, S., "Testosterone treatment for hypoactive sexual desire disorder in postmenopausal women," J. Sex Med. 4 Suppl 3: 227-234 (2007).
Kliewer et al., "Retinoid X receptor interacts with nuclear receptors in retinoic acid, thyroid hormone and vitamin D3 signalling," Nature 355(6359):446-449 (1992).
Kolvenbag, G. and G. Blackledge, "Worldwide activity and safety of bicalutamide: a summary review," Urology 47 (Suppl. 1A):70-79 (1996).
Kong et al., "Effects of isosteric pyridone replacements in androgen receptor antagonists based on 1,2-dihydro- and 1,2, 3,4-tetrahydro-2,2-dimethyl-6-trifluoromethyl-8-pyridono[5,6-g]quinolines," Bioorganic Medicine and Chemistry Letters, 10(5):411-414, (2000).
Korte, W., "Changes of the coagulation and fibrinolysis system in malignancy: their possible impact on future diagnostic and therapeutic procedures," Clin. Chem. Lab Med. 38(8):679-692 (2000).
Koyama et al., "A one step sandwich enzyme immunoassay for gamma-carboxylated osteocalcin using monoclonal antibodies," J. Immunol. Methods 139(1):17-23 (1991).
Kurokouchi et al., "TNF-alpha increases expression of IL-6 and ICAM-1 genes through activation of NF-kappaB in osteoblast-like ROS17/2.8 cells," J. Bone Mineral Res. 13(8):1290-1299 (1998).
Laaksonen et al., "Sex hormones, inflammation and the metabolic syndrome: a population-based study," Euro. J. Endocrinol. 149(6):601-608 (2003).
Laaksonen et al., "Testosterone and sex hormone-binding globulin predict the metabolic syndrome and diabetes in middle-aged men," Diabetes Care 27(5):1036-1041 (2004).
Labrie et al., "Tetrahydrogestrinone induces a genomic signature typical of a potent anabolic steroid," J. Endocrinol. 184(2):427-433 (2005).
Lapointe et al., "Androgens down-regulate bcl-2 protooncogene expression in ZR-75-1 human breast cancer cells," Endocrinology 140(1): 416-421 (1999).
Lemus et al., "5alpha-reduction of norethisterone enhances its binding affinity for androgen receptors but diminishes its androgenic potency," J. Steroid Biochem. Mol. Biol. 60(1-2):121-129 (1997).
Lin et al., "Insulin and leptin resistance with hyperleptinemia in mice lacking androgen receptor," Diabetes 54(6): 1717-1725 (2005).
Long et al., "Selective androgen receptor modulators based on a series of 7H-[1,4]oxazino[3,2-g]quinolin-7-ones with improved in vivo activity," Bioorg. Med. Chem. Lett. 18(9):2967-2671 (2008).
Lovejoy et al., "Exogenous androgens influence body composition and regional body fat distribution in obese postmenopausal women—a clinical research center study," J. Clin. Endocrinol. Metabol. 81(6):2198-2203 (1996).
Lovejoy et al., "Oral anabolic steroid treatment, but not parenteral androgen treatment, decreases abdominal fat in obese, older men," Int. J. Obesity 19(9):614-624 (1995).
Lufkin et al., The role of selective estrogen receptor modulators in the prevention and treatment of osteoporosis, Rheum. Dis. Clin. N. Am. 27(1):163-185 (2001).
Ly et al., "Rates of suppression and recovery of human sperm output in testosterone-based hormonal contraceptive regimens," Hum. Reprod. 20(6):1733-1740 (2005).
Lynch et al., "Therapeutic approaches for muscle wasting disorders," Pharmacol. Therapeut. 113(3):461-487 (2007).
Lynch, G., "Emerging drugs for sarcopenia: age-related muscle wasting," Expert Opin. Emerg. Drugs 9(2):345-361 (2004).

(56) References Cited

OTHER PUBLICATIONS

Mahfouz et al., "Synthesis, chemical and enzymatic hydrolysis, and bioavailability evaluation in rabbits of metronidazole amino acid ester prodrugs with enhanced water solubility," J. Pharm. Pharmacol. 53(6):841-848 (2001).
Majumdar et al., "Studies on the amine oxide rearrangements: regioselective synthesis of pyrrolo[3,2-f]quinolin-7-ones," J. Chem. Res. S. 9:310-311 (1997).
Mangelsdorf et al., "A direct repeat in the cellular retinol-binding protein type II gene confers differential regulation by RXR and RAR," Cell 66:555-561 (1991).
Marhefka et al., "Design, synthesis, and biological characterization of metabolically stable selective androgen receptor modulators," J. Med. Chem. 47(4):993-998 (2004).
Marin et al., "Androgen treatment of abdominally obese men," Obesity Res. 1(4):245-251 (1993).
Maron et al., "Revised methods for the *Salmonella* mutagenicity test," Mutat. Res. 113(3-4):173-215 (1983).
Martinborough et al., "Substituted 6-(1-pyrrolidine)quinolin-2(1H)-ones as novel selective androgen receptor modulators," J. Med. Chem. 50(21):5049-5052 (2007).
Marynick et al., "Androgen Excess in Cystic Acne," n. Engl J Med (1983) 308:981-986.
Maucher, A. and E. von Angerer, "Antiproliferative activity of Casodex (ICI 176.334) in hormone-dependent tumours," J. Cancer Res. Clin. Oncol. 119(11):669-674 (1993).
Max et al., "Cytosolic androgen receptor in regenerating rat levator ani muscle," Biochem. J. 200(1): 77-82 (1981).
McDonnell et al., "RU486 exerts antiestrogenic activities through a novel progesterone receptor A form-mediated mechanism," J. Biol. Chem. 269(16):11945-11949 (1994).
Michellys et al., "Design, synthesis, and structure-activity relationship studies of novel 6,7-locked-[7-(2-alkoxy-3,5-dialkylbenzene)-3-methylocta]-2,4,6-trienoic acids," Journal of Medicinal Chemistry, 46(19):4087-4103, (2003).
Miller, C., and B. Komm, "Section IV: Immunology, endriconology and metabolic diseases. Chapter 15: Targeting the Estrogen Receptor with SERMs," Ann. Rep. Med. Chem. 36:149-158 (2001).
Miller, K., "Androgen deficiency in women," Clin. Endocrinol. Metabol. 86:2395-2401 (2001).
Miner et al., "An orally active selective androgen receptor modulator is efficacious on bone, muscle, and sex function with reduced impact on prostate," Endocrinology 148(1):363-373 (2007).
Miyake et al., "Androgen receptor expression in the preputial gland and its sebocytes," J. Invest. Dermatol. 103(5):721-725 (1994).
Mooradian et al., "Biological action of androgens," Endocr. Rev. 8(1):1-28 (1987).
Morrissey et al., "Changes in hormone sensitivity in the ventral prostate of aging Sprague-Dawley rats," J. Androl. 23(3):341-351 (2002).
Navone et al., "Establishment of two human prostate cancer cell lines derived from a single bone metastasis," Clin. Cancer Res. 3:2493-2500 (1997).
Navone et al., "TabBO: A model reflecting common molecular features of androgen-independent prostate cancer," Clin. Cancer Res. 6:1190-1197 (2000).
Negro-Vilar, "Selective androgen receptor modulators (SARMs) a novel approach to androgentherapy for the new millennium," J. Clin. Endocrinol. Metabol. 84(10):3459-3462 (1999).
Neri et al., "Complete androgen blockade as treatment for advanced prostate cancer: clinical response and side-effects," Anticancer Res. 9(1):13-16 (1989).
Neri, R. and E. Peets, "Biological aspects of antiandrogens," J. Steroid Biochem. 6(6):815-819 (1975).
Neri, R., "Pharmacology and pharmacokinetics of flutamide," Urology 34(4 Suppl.):19-21 (1989).
Neri, R., "Pharmacology and pharmacokinetics of flutamide," Urology 34(4 Suppl.):46-56 (1989).
Ng et al., "Differential induction of the interleukin-6 gene by tumor necrosis factor and interleukin-1," J. Biol. Chem. 269(29):19021-19027 (1994).
Nickerson et al., "Effect of testosterone propionate on the ultrastructure of the preputial gland in the rat," Acta Anat. (Basel) 94:481-489 (1976).
Niculescu-Duvaz et al., "Self-immolative nitrogen mustard prodrugs for suicide gene therapy," Journal of Medicinal Chemistry, 41:5297-5309, (1998).
Niikura et al., "A novel inhibitor of vacuolar ATPase, FR167356, which can discriminate between osteoclast vacuolar ATPase and lysosomal vacuolar ATPase," Br. J. Pharmacol. 142:558-566 (2004).
Niikura, K., "Vacuolar ATPase as a drug discovery target," Drug News Perspect. 19(3):139-144 (2006).
Nogrady, T., Medicinal Chemistry A Biochemical Approach, Oxford University Press, New York, N.Y., pp. 388-392, (1985).
Notelovitz, M., "Hot flashes and androgens: a biological rationale for clinical practice," Mayo Clin. Proc. 79(4 Suppl):S8-S13 (2004).
Omwancha, J. and T. Brown, "Selective androgen receptor modulators: in pursuit of tissue-selective androgens," Curr. Opin. Investig. Drugs 7(10):873-881 (2006).
O'Reilly et al., "Regulation of expression of a baculovirus ecdysteroid UDP glucosyltransferase gene," in Baculovirus Expression Vectors, WH Freeman:NY, 139-179 (1992).
Okazaki et al., "Thiazolidinediones inhibit osteoclast-like cell formation and bone resorption in vitro," Endocrinology 140:5060-5065 (1999).
Palmer et al., "Hypoxia-selective antitumor agents. 3. Relationships between structure and cytotoxicity against cultured tumor cells for substituted N,N-bis(2-chloroethyl)anilines," Journal of Medicinal Chemistry, 33:112-121, (1990).
Palmer et al., "Hypoxia-selective antitumor agents. 5. Synthesis of water-soluble nitroaniline mustards with selective cytotoxicity for hypoxic mammalian cells," Journal of Medicinal Chemistry, 35:3214-3222, (1992).
Palmer et al., "Nitro analogues of chlorambucil as potential hypoxia-selective anti-tumour drugs," Anti-Cancer Drug Design, 5:337-349, (1990).
Pan, H. and T. Fletcher, "Derivatives of fluorene. IX. 4-hydroxy-2-fluorenamine; new 3,4-benzocoumarin derivatives," J. Org. Chem. 25:1106-1109 (1960).
Panthananickal et al., "Structure-activity relationship of aniline mustards acting against B-16 melanoma in mice," Journal of Medicinal Chemistry, 22:1267-1269, (1979).
Papasozomenos et al., "Testosterone prevents the heat shock-induced overactivation of glycogen synthase kinase-3β but not of cyclin-dependent kinase 5 and c-Jun NH2-terminal kinase and concomitantly abolishes hyperphosphorylation of I[: Implications for Alzheimer's disease," Proc. Nat. Acad. Sci. U.S.A. 99:1140-1145 (2002).
Pasquali, R., "Obesity and androgens: facts and perspectives," Fertil. Steril. 85(5):1319-1340 (2006).
Pasqualotto et al., "Trends in male contraception," Rev. Hosp. Clin. Fac. Med. Sao Paulo 58(5):275-283 (2003).
Pathirana et al., "Nonsteroidal human progesterone receptor modulators from the marine alga *Cymopolia barbatam*," Molecular Pharmacology, 47:630-635, (1995).
Peehl, D., "Human prostatic epithelial and stromal cell lines and strains," Urol. Oncol. 2(4):100-102 (1996).
Peltier et al., "Technical note: application of the box-cox data transformation to animal science experiments," J. Anim. Sci. 76: 847-849 (1998).
Petrangolini et al., "Effect of a novel vacuolar-H+-ATPase inhibitor on cell and tumor response to camptothecins," J. Pharmacol. Exp. Ther. 318 (3):939-946 (2006).
Pfankuch et al., "Role of circulating androgen levels in effects of apoE4 on cognitive function," Brain Res. 1053(1-2): 88-96 (2005).
Pietschmann et al., "Bone structure and metabolism in a rodent model of male senile osteoporosis," Exp. Gerontol. 42(11): 1099-1108 (2007).
Pooley et al., "Discovery and preliminary SAR studies of a novel, nonsteroidal progesterone receptor antagonist pharmacophore," Journal of Medicinal Chemistry, 41:3461, (1998).

(56) References Cited

OTHER PUBLICATIONS

Popp, "Synthesis of potential antineoplastic agents X. Preparation and reactions of aldehydes related to benzaldehyde mustard," Journal of Medicinal Chemistry, 7:210-212, (1964).
Prakash et al., "Synthetic methods and reactions. 141. Fluorine-induced trifluoromethylation of carbonyl compounds withtrifluoromethyltrimethylsilane (TMS-CF3). A trifluoromethide equivalent," J. Am. Chem. Soc. 111(1):393-395 (1989).
Prasmickiene et al., "Synthesis and study of the reactivity of p-[bis(2-chloropropyl)amino]phenylalkanoic acids," Izvestiya Akademii Nauk SSSR, Seriya Khimicheskaya, 3:643-646, (1969).
Prasmitskene et al., "The synthesis and study of the reactivity of p-[di-(2-chloropropyl)amino]phenylalkanoic acids," Bull.Acad.Sci. USSR. Chem. Sci. 3:576-579 (1969).
Preston et al., "Mammalian in vivo and in vitro cytogenetic assays: a report of the U.S. EPA's gene-tox program," Mutat. Res. 87(2):143-188 (1981).
Purdie, D., "Consequences of long-term hormone replacement therapy," Br. Med. Bull. 56(3):809-823 (2000).
Quimby et al., "Tetrasodium carbonyldiphosphonate. Synthesis, reactions, and spectral properties," J. Org. Chem. 32(12):4111-4114 (1967).
Raber et al., "Androgens protect against Apolipoprotein E-4 induced cognitive deficits," J. Neurosci. 22(12):5204-5209 (2002).
Reid et al., "Antiandrogens in prostate cancer," Investig. New Drugs 17:271-284 (1999).
Remington, "The Science and Practice of Pharmacy, 19th Ed.," Mack Publishing Co., Easton, PA., pp. 1399-1404 (1995).
Rettig et al. Journal of Physical Chemistry (1985), 89(22), 4676-80.
Ricciardelli et al., "Effects of oestradiol-17β and 5-dihydrotestosterone on guinea-pig prostate smooth muscle cell proliferation and steroid receptor expression in vitro," J. Endocrinol. 140(3):373-383 (1994).
Rivera-Woll et al., "Androgen insufficiency in women: diagnostic and therapeutic implications," Hum. Reproduct. Update 10(5):421-432 (2004).
Roche, E. ed., "Bioreversible carriers in drug design: theory and application," Pergamon Press: New York, pp. 14-21 (1987).
Sadeghi-Nejad et al., "Preliminary report on the development and characterization of rabbit clitoral smooth muscle cell culture," Int. J. Impotence Res. 10(3):165-169 (1998).
Salm et al., "Transforming growth factor-beta is an autocrine mitogen for a novel androgen-responsive murine prostatic smooth muscle cell line, PSMC1," J. Cell. Physiol. 185(3):416-424 (2000).
Sastry et al., "Synthesis and antibacterial activity of 1,4-oxazinoquinolone carboxylic acids," Indian J. Chem. Section B 27:649-652 (1988).
Seed et al., "The inhibition of colon-26 adenocarcinoma development and angiogenesis by topical diclofenac in 2.5% hyaluronan," Cancer Res. 57:1625-1629 (1997).
Segal et al., "Therapeutic potential of the SARMs: revisiting the androgen receptor for drug discovery," Expert Opin. Investig. Drugs 15(4):377-387 (2006).
Selvakumar et al., Observation of Q->N Type Smiles Rearrangement in Certain Alkyl Aryl Nitro Compounds1, Synthesis (2002) (16):2421-2425.
Serizawa, K., et al., Science of Polymorphic Phenomena and Crystallization of Pharmaceuticals, Mauzen Planet Co., Ltd., Sep. 20, 2002, pp. 305-317.
Sharifi et al., "Androgen Receptor as a Therapeutic Target for Androgen Independent Prostate Cancer," American Journal of Theraputics (2006) 13(2):166-170.
Sharma, P. and N. Schreiber-Agus, "Mouse models of prostate cancer," Oncogene 18(38):5349-5355 (1999).
Shayeganpour et al., "Determination of the enzyme(s) involved in the metabolism of amiodarone in liver and intestine of rat: the contribution of cytochrome P450 3A isoforms," Drug Metab. Dispos. 34 (1):43-50 (2006).
Shen et al., "Androgen-induced growth inhibition of androgen receptor expressing androgen-independent prostate cancer cells is mediated by increased levels of neutral endopeptidase," Endocrinology 141(5):1699-1704 (2000).
Simental et al., "Transcriptional activation and nuclear targeting signals of the human androgen receptor," J. Biol. Chem. 266(1):510-518 (1991).
Sinclair, et al., "Male pattern androgenetic alopecia," BMJ. Sep. 26, 1998; 317(7162): 865-869.
Singhal, et al., "Drug polymorphism and dosage form design: a practical perspective," Advanced Drug Delivlery Reviews 56 (2004) 335-347.
Sit et al., "Relationship between bone mineral density and biochemical markers of bone turnover in hemodialysis patients," Adv. Ther. 24(5):987-995 (2007).
Smith et al., "March's Advanced Organic Chemistry, 6th ed.," Wiley, NJ, pp. 1053-1062 (2007).
Smith ct al., "March's Advanced Organic Chemistry, 6th ed.," Wiley, NJ, pp. 1300-1309 (2007).
Smith et al., "March's Advanced Organic Chemistry, 6th ed.," Wiley, NJ, pp. 1715-1728 (2007).
Smith et al., "March's Advanced Organic Chemistry, 6th ed.," Wiley, NJ, pp. 1805-1806 (2007).
Sokolov et al. Zhurnal Obshchei Khimi (1966), 2(6), 1088-92.
Srinivasan, G. and E. Thompson, "Overexpression of full-length human glucocorticoid receptor in Spodoptera frugiperda cells using the baculovirus expression vector system," Mol. Endo. 4(2):209-216 (1990).
Srivastava et al., "Development and application of a serum C-telopeptide and osteocalcin assay to measure bone turnover in an ovariectomized rat model," Calcified Tissue Int. 66(6):435-442 (2000).
Steinman et al., "1-Polyfluoroalkylbenzodiazepines; 1.," Journal of Medicinal Chemistry, 16:1354-1360, (1973).
Stoch et al., "Bone loss in men with prostate cancer treated with gonadotropin-releasing hormone agonists," J. Clin. Endocrinol. Metabol. 86(6):2787-2791 (2001).
Sulak, P., "Ovulation suppression of premenstrual symptoms using oral contraceptives," Am. J. Manag. Care 11:S492-S497 (2005).
Suzuki et al., "Effects of antiandrogens on growth of androgen-dependent mouse mammary tumor (Shionogi carcinoma 115) in vivo and in vitro," J. Steroid Biochem. Mol. Biol. 37(4):559-567 (1990).
Svartberg, J. Androgens and chronic obstructive pulmonary disease. Current Opinion in Endocrinology, Diabetes and Obesity Issue: vol. 17(3), Jun. 2010, p. 257-261 (abstract only).
Szulc et al., "Biochemical assessment of bone turnover and bone fragility in men," Osteoporos Int. 18(11):1451-1461 (2007).
Tacke and Zilch, "Sila-substitution—a useful strategy for drug design?" Endeavour, 10:191-197, (1986).
Tajana et al., "Synthesis of a testosterone-dependent secretory protein by rat seminal vesicle-derived cell lines," EMBO J. 3(3):637-644 (1984).
Takada, N., Active Pharmaceutical Ingredient Form Screening and Selection in Drug Development State, Pharm Stage, vol. 6, No. 10, Jan. 15, 2007, pp. 20-25.
Thevis et al., "Screening for 2-quinolinone-derived selective androgen receptor agonists in doping control analysis," Rapid Commun. Mass Spectrom. 21(21):3477-3486 (2007).
Tobias et al., "5 alpha-Dihydrotestosterone partially restores cancellous bone volume in osteopenic ovariectomized rats," Am. J. Physiol. 267(6 Pt 1): E853-E859 (1994).
Tsujii et al., "Cyclooxygenase regulates angiogenesis induced by colon cancer cells," Cell 93(5):705-716 (1998).
Turnbull et al., "The Reaction of 4-Substituted Aryl Isocyanates with NaBH4/Trifluoroacetic Acid (TFA)," Synthesis, 3:391-392, (1999).
Turner et al., "Contraceptive efficacy of a depot progestin and androgen combination in men," J. Clin. Endocrinol. Metabol. 88(10):4659-4667 (2003).
Turner, C. and D. Burr, "Basic biomedical measurements of bone: a tutorial," Bone 14:595-608 (1993).
Umesono et al., "Retinoic acid and thyroid hormone induce gene expression through a common responsive element," Nature 336:262-265 (1988).

(56) References Cited

OTHER PUBLICATIONS

Vadja et al., "LGD-4033 builds muscle and bone with reduced prostate activity and may be beneficial in age-related frailty," Gerontological Society of America 62nd Annual Scientific Meeting, Atlanta, Georgia, Nov. 18-22, 2009, 1 page [poster presentation].
Van Oeveren et al., "Discovery of 6-N,N-bis(2,2,2-trifluoroethyl)amino-4-trifluoromethylquinolin-2(1H)-one as a novel selective androgen receptor modulator," J. Med. Chem. 49(21):6143-6146 (2006).
Van Oeveren et al., "Discovery of an androgen receptor modulator pharmacophore based on 2-quinolinones," Bioorg. Med. Chem. Lett. 17(6):1523-1526 (2007).
Van Oeveren et al., "Novel selective androgen receptor modulators: SAR studies on 6-bisalkylamino-2-quinolinones," Bioorg. Med. Chem. Lett. 17(6):1527-1531 (2007).
Van Weerden et al., "Human prostate tumor xenografts as representative models for clinical prostate cancer," Urol. Oncol. 2: 122-125 (1996).
Vandenput et al., "The estrogen receptor ligand ICI 182,780 does not impair the bone-sparing effects of testosterone in the young orchidectomized rat model," Calcified Tissue Int. 70(3):170-175 (2002).
Vanderschueren et al., "Time-related increase of biochemical markers of bone turnover in androgen-deficient male rats," Bone Miner. 26(2): 123-131 (1994).
Vanderschueren et al., "An aged rat model of partial androgen deficiency: prevention of both loss of bone and lean body mass by low-dose androgen replacement," Endocrinology 141(5):1642-1647 (2000).
Vanderschueren et al., "Androgens and bone," Endocrine Rev. 25(3):389-425 (2004).
Vegeto et al., "The mechanism of RU486 antagonism is dependent on the conformation of the carboxy-terminal tail of the human progesterone receptor," Cell 69(4):703-713 (1992).
Visentin et al., "A selective inhibitor of the osteoclastic V-H(+)-ATPase prevents bone loss in both thyroparathyroidectomized and ovariectomized rats," J. Clin. Invest. 106(2):309-318 (2000).
Wagaw et al., "Palladium-catalyzyed coupling of optically active amines with aryl bromides," J. Am. Chem. Soc. 119(12):8451-8458 (1997).
Wakley et al., "Androgen treatment prevents loss of cancellous bone in the orchidectomized rat," J. Bone Min. Res. 6(4):325-330 (1991).
Wang et al., "Male rodent model of age-related bone loss in men," Bone 29(2):141-148 (2001).
Willy et al., "LXR, a nuclear receptor that defines a distinct retinoid response pathway," Genes Dev. 9(9):1033-1045 (1995).
Wright et al., "Analysis of myosin heavy chain mRNA expression by RT-PCR," J. Appl. Physiol. 83(4):1389-1396 (1997).
Wuts et al., "Green's Protective Groups in Organic Synthesis, 4th ed.," Wiley, NJ, pp. 725-727 (2007).
Wuts et al., "Green's Protective Groups in Organic Synthesis, 4th ed.," Wiley, NJ, pp. 727-735 (2007).
Xin et al., "Peroxisome proliferator-activated receptor γ ligands are potent inhibitors of angiogenesis in vitro and in vivo," J. Biol. Chem. 274(13):9116-9121 (1999).
Yalpani, "Cholesterol Lowering Drugs," Chem. Ind. 3:85-89 (1996).
Yamada et al., "Comparative evaluation of a 5-day hershberger assay utilizing mature male rats and a pubertal male assay for detection of flutamide's antiandrogenic activity," Tox. Sciences 53: 289-296 (2000).
Yamano, M., Approach to Crystal Polymorph in Process Research of New Drug, Japanese Journal of Synthetic Organic Chemistry, Sep. 1, 2007, vol. 65, No. 9.
Yassin et al., "Treatment of sexual dysfunction of hypogonadal patients with long-acting testosterone undecanoate (Nebido)," World J. Urol. 24:6:639-644 (2006).
Ye et al., "Androgen and epidermal growth factor down-regulate cyclin-dependent kinase inhibitor p27Kipl and costimulate proliferation of MDA PCa 2a and MDA PCa 2b prostate cancer cells," Clin. Cancer Res. 5(8):2171-2177 (1999).
Ye et al., Synthesis and Biological Evaluation of Menthol-Based Derivatives as Inhibitors of Plasminogen Actiator Inhibitor-1 (PAI-1-Bioorganic & Medicinal Chemistry Letters (2003) 13(19):3361-3365.
Yeap et al., "Differential posttranscriptional regulation of androgen receptor gene expression by androgen in prostate and breast cancer cells," Endocrinology 140:3282-3291 (1999).
Yin et al., "Key structural features of nonsteroidal ligands for binding and activation of the androgen receptor," Molecular Pharmacology, 63(1):211-223, (2003).
Yin et al., "Pharmacodynamics of selective androgen receptor modulators," J. Pharmacol. Exp. Ther. 304(3):1334-1340 (2003).
Yki-Järvinen, H., "Thiazolidinediones," N. Eng. J. Med. 351(11):1106-1118 (2004).
Yoshino et al. STN Accession No. 1990:523190, Abstract of Yoshino et al. Technology Reports of the Osaka University (1990), 40(1986-2003), 81-5.
Zacharski, L. and D. Orenstein, "Heparin and cancer," Thromb. Haemost. 80(1):10-23 (1998).
Zhang et al., "Design, synthesis, and in vivo SAR of a novel series of pyrazolines as potent selective androgen receptor modulators," J. Med. Chem. 50(16):3857-3869 (2007).
Zhang et al., "Human prostatic smooth muscle cells in culture: estradiol enhances expression of smooth muscle cell-specific markers," Prostate 30(2):117-129 (1997).
Zhi and Martinborough, "Chapter 17: Selective androgen receptor modulators (SARMs)," Annual Reports in Medicinal Chemistry, 36:169-180, (2001).
Zhi et al., "Switching androgen receptor antagonists to agonists by modifying C-ring substituents on piperidino[3,2-g]quinolinone," Bioorganic and Medicinal Chemistry Letters, 9(7):1009-1012, (1999).
Zhi et al., "Nonsteroidal progesterone receptor antagonists based on 6-thiophenehydroquinolines," Bioorganic and Medicinal Chemistry Letters, 10:415-418, (2000).
Zhi et al., "5-aryl-1,2-dihydrochromeno[3,4-f]quinolines: a novel class of nonsteroidal human progesterone receptor agonists," J. Med. Chem. 41(3):291-302 (1998).
Zhi, L. and K. Marschke, "Novel class of non-steroidal progesterone receptor antagonists," Expert Opin. Ther. Patents 9(6):695-700 (1999).
Zhuang et al., "Subcellular location of androgen receptor in rat prostate, seminal vesicle and human osteosarcoma MG-63 cells," J. Steroid Biochem. Mol. Biol. 41(3-8):693-696 (1992).
Zyss et al., Chirality and hydrogen bonding in molecular crystals for phase-matched second-harmonic generation: N-(4-nitropheyl)-(L)-prollnol (NPP), Journal of Chemical Physics (1984) 81(9):4160-7.

\* cited by examiner

Differential Scanning Calorimetry and Thermogravimetric Analysis overlay for crystalline Form C of compound of Formula (I)

Differential Scanning Calorimetry results for crystalline Form E of compound of Formula (I)

Differential Scanning Calorimetry and Thermogravimetric Analysis overlay for crystalline Forms E + C of compound of Formula (I)

VT-XRPD data for Crystalline Form E of compound of Formula (I)

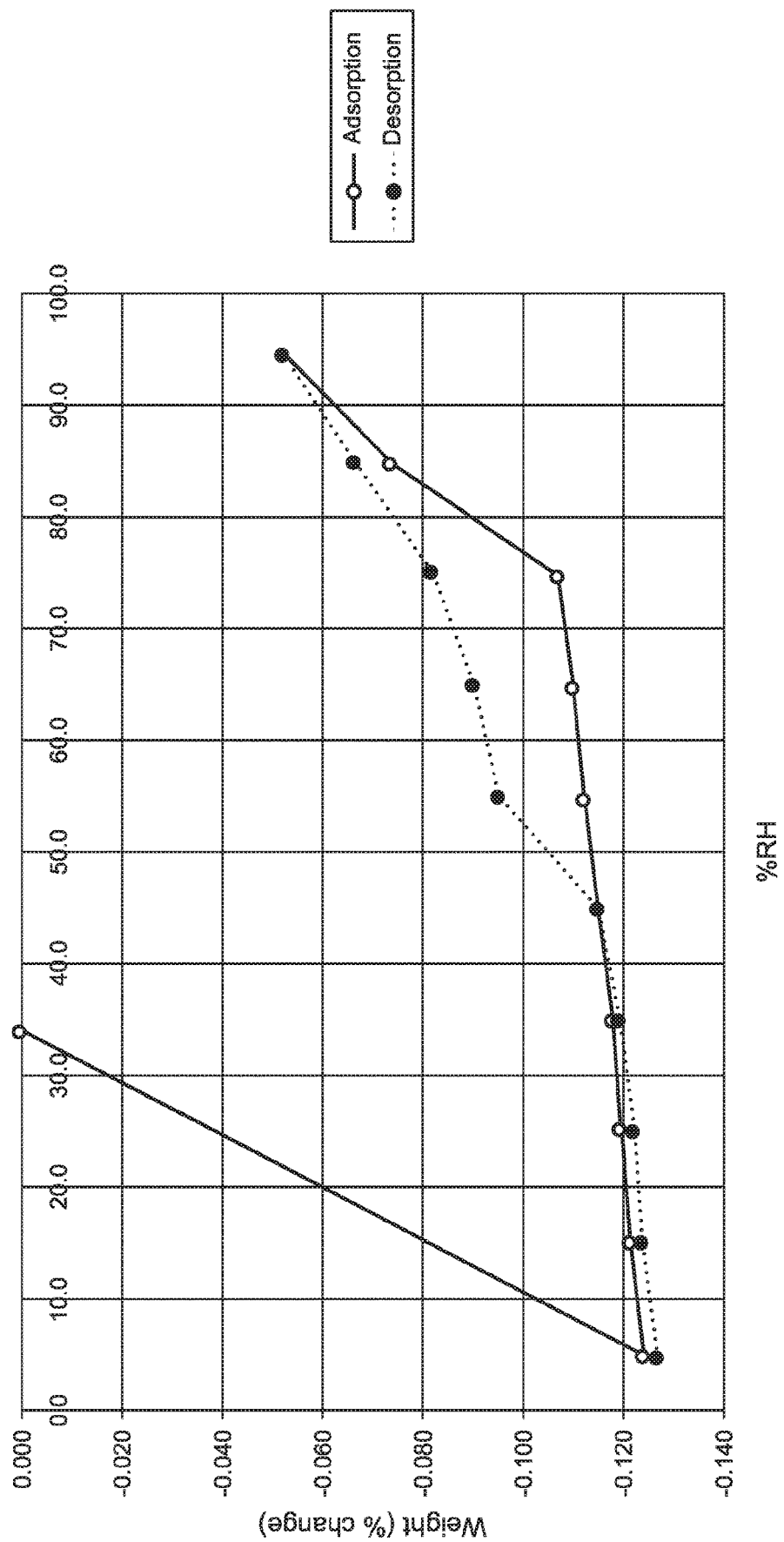

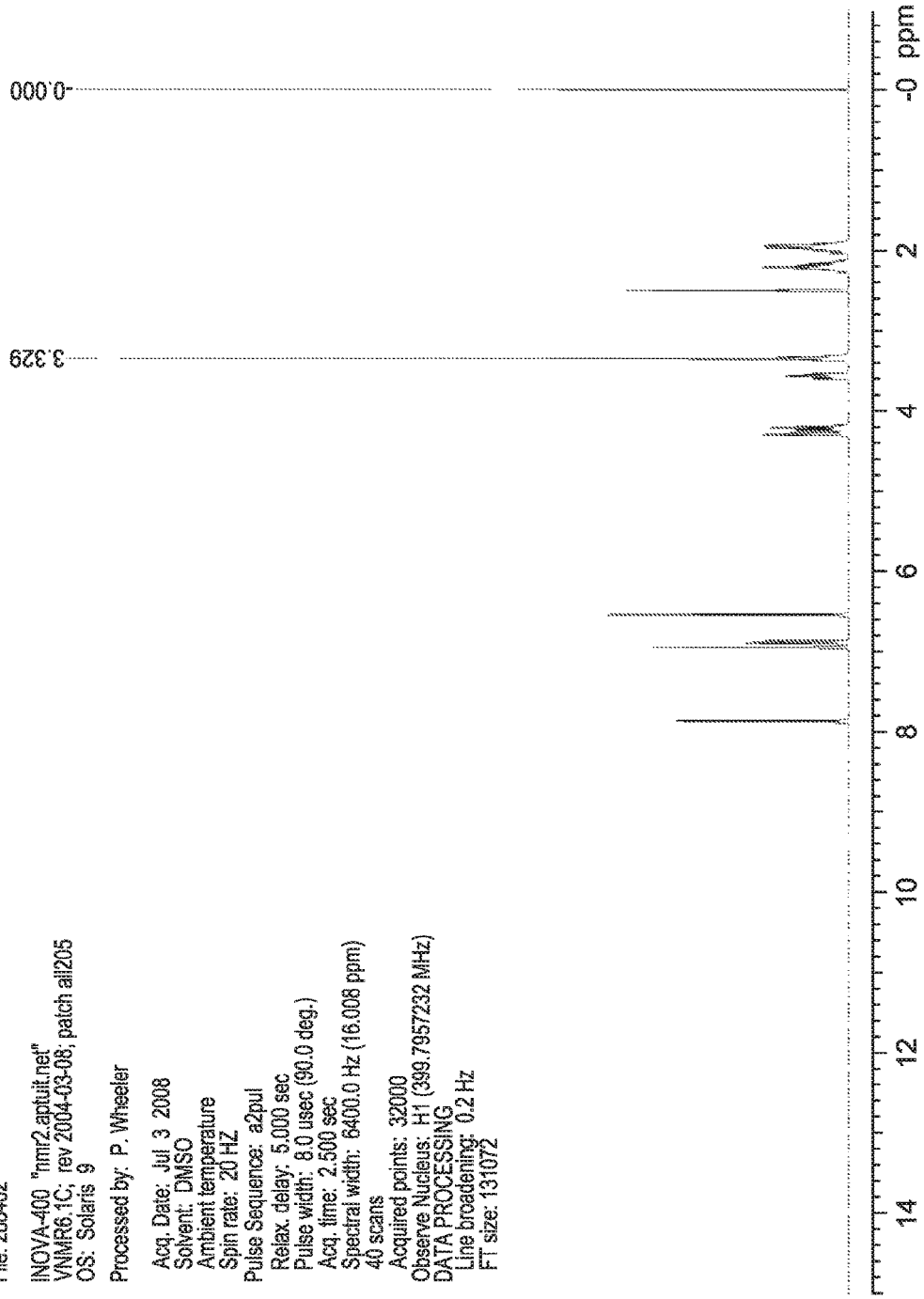

CRYSTALLINE FORMS AND METHODS OF PRODUCING CRYSTALLINE FORMS OF A COMPOUND

CROSS REFERENCE TO RELATED APPLICATIONS

This application is U.S. National Phase under 35 U.S.C. § 371 of International Application No. PCT/US2020/028550, filed Apr. 16, 2020, designating the U.S. and published in English as International Pub. No. WO 2020/214834, which claims the benefit of U.S. Provisional Application No. 62/836,517, filed Apr. 19, 2019, each of which is incorporated herein by reference in its entirety.

BACKGROUND

Field of the Invention

The present application relates to the fields of pharmaceutical chemistry, biochemistry, and medicine. In particular, it relates to crystalline forms of the compound of Formula (I) and methods of making and using the same.

Description of the Related Art

Certain intracellular receptors (IRs) have been shown to regulate transcription of certain genes (e.g., see R. M. Evans, Science 240: 889 (1988)). Certain of such IRs are steroid receptors, such as androgen receptors, estrogen receptors, mineralo-corticoid receptors, and progesterone receptors. Gene regulation by such receptors typically involves binding of an IR by a ligand.

In certain instances, a ligand binds to an IR, forming a receptor/ligand complex. Such a receptor/ligand complex can then translocate to the nucleus of a cell, where it binds to the DNA of one or more gene regulatory regions. Once bound to the DNA of a particular gene regulatory region, a receptor/ligand complex can modulate the production of the protein encoded by that particular gene. In certain instances, an androgen receptor/ligand complex regulates expression of certain proteins. In certain instances, an androgen receptor/ligand complex can interact directly with the DNA of a particular gene regulatory region or with other transcription factors. In certain instances, such interactions result in modulation of transcriptional activation.

Androgen therapy has been used to treat a variety of male disorders such as reproductive disorders and primary or secondary male hypogonadism. A number of natural or synthetic AR agonists have been investigated for the treatment of musculoskeletal disorders, such as bone disease, hematopoietic disorders, neuromuscular disease, rheumatological disease, wasting disease, and for hormone replacement therapy (HRT), such as female androgen deficiency. In addition, AR antagonists, such as flutamide and bicalutamide, are used to treat prostate cancer. The effectiveness of known modulators of steroid receptors is often tempered by their undesired side-effect profile, particularly during long-term administration. For example, potential side effects of androgen therapy for women include acne, weight gain, excess facial and body hair, permanent lowering of the voice, and adverse lipid changes. In men, adverse effects can include disordered sleep and breathing, polycythemia, and repression of high density lipoprotein. Thus there is a need for compounds that do not exhibit the adverse side-effects.

It is among the objects herein to provide such compounds that modulate the activity of androgen receptor.

SUMMARY OF THE INVENTION

Some embodiments provide a crystalline form of a compound of Formula

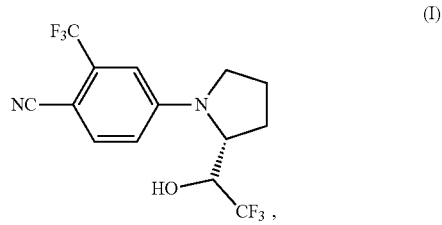 [SMILES: N#Cc1ccc(N2CCC[C@@H]2C(O)C(F)(F)F)cc1C(F)(F)F]

or a solvate thereof.

In some embodiments, the crystalline form of the compound of Formula (I) may exhibit an X-ray powder diffraction pattern comprising at least one characteristic peak selected from the group consisting of approximately 8.5, 11.8, 12.4, 13.3, 13.7, 15.0, 17.1, 17.5, 18.2, 18.5, 19.5, 21.1, 21.7, 22.1, 22.6, 23.1, 23.7, 24.8, 25.0, 25.5, 26.2, 27.5, and 29.6 degrees 2θ. In some embodiments, the crystalline form of the compound of Formula (I) may exhibit an X-ray powder diffraction pattern comprising at least three characteristic peaks, wherein said characteristic peaks are selected from the group consisting of 8.5, 13.3, 13.7, 15.0, 17.5, 18.2, 18.5, 19.5, 21.1, 23.1, 23.7, 25.5, and 26.2 degrees 2θ. In some embodiments, the crystalline form of the compound of Formula (I) may have a melting point of about 163° C.

In some embodiments, the crystalline form of the compound of Formula (I) may exhibit an X-ray powder diffraction pattern comprising at least one characteristic peak selected from the group consisting of approximately 9.6, 11.7, 13.0, 13.9, 14.2, 15.2, 15.8, 17.5, 19.1, 19.4, 21.2, 21.9, 22.6, 23.3, 23.6, 24.7, 25.3, 25.6, 25.9, 26.9, 28.1, and 29.0 degrees 2θ. In some embodiments, the crystalline form of the compound of Formula (I) may exhibit an X-ray powder diffraction pattern comprising at least three characteristic peaks selected from the group consisting of approximately 9.6, 11.7, 13.0, 13.9, 15.8, 17.5, 19.1, 19.4, 21.2, 21.9, 22.6, 23.3, 23.6, 25.3, and 25.6 degrees 2θ. In some embodiments, the crystalline form of the compound of Formula (I) may have a melting point of about 162° C.

In some embodiments, the crystalline form of the compound of Formula (I) may exhibit an X-ray powder diffraction pattern comprising at least one characteristic peak selected from the group consisting of approximately 9.0, 10.3, 11.7, 12.7, 13.3, 14.0, 14.8, 16.0, 17.1, 17.6, 19.2, 19.8, 21.3, 21.9, 22.6, 23.4, 23.7, 24.6, 25.4, 25.7, 26.2, 27.4, 28.3, and 29.2 degrees 2θ. In some embodiments, the crystalline form of the compound of Formula (I) may exhibit an X-ray powder diffraction pattern comprising at least three characteristic peak selected from the group consisting of approximately 9.0, 10.3, 11.7, 12.7, 13.3, 16.0, 17.6, 21.3, 21.9, 22.6, 24.6, and 26.2 degrees 2θ. In some embodiments, the crystalline form of the compound of Formula (I) may have a melting point of about 162° C.

In some embodiments, the crystalline forms of the compound of Formula (I) provided herein may be solvated. In other embodiments, of the compound of Formula (I) may be unsolvated.

Additional embodiments provided herein include compositions comprising a crystalline form of the compound of Formula (I). In some embodiments, the total weight of the compound of Formula (I) in the composition may comprise greater than 50% by weight of the crystalline form. In some embodiments, the total weight of the compound of Formula (I) in the composition may comprise greater than 80% by weight of the crystalline form. In some embodiments, the total weight of the compound of Formula (I) in the composition may comprise greater than 95% by weight of the crystalline form. In some embodiments, the total weight of the compound of Formula (I) in the composition may consist essentially of the crystalline form. In some embodiments, the crystalline form may be crystalline Form C. In other embodiments, the crystalline form may be crystalline Form E. In some embodiments, the crystalline form may be crystalline Form B.

A further embodiments provided herein include a method of treating a disease or disorder comprising administering to a subject a therapeutically effective amount of a composition comprising a crystalline form of the compound of Formula (I). In some embodiments, the disease or disorder may be selected from the group consisting of: aging skin; Alzheimer's disease; anemias; anorexia; arthritis; arteriosclerosis; atherosclerosis; bone disease; distraction osteogenesis; reduced bone mass, density or growth; bone weakening; musculoskeletal impairment; cachexia; cancer; cardiac dysfunction; catabolic side effects of glucocorticoids; Crohn's disease; growth retardation in connection with Crohn's disease; short bowel syndrome; irritable bowel syndrome; inflammatory bowel disease; ulcerative colitis; cognitive decline and impairment; dementia; short term memory loss; contraception (male and female); chronic obstructive pulmonary disease (COPD); chronic bronchitis; decreased pulmonary function; emphysema; decreased libido in both men and women; depression; nervousness, irritability and/or stress; reduced mental energy and low self-esteem; dyslipidemia; erectile dysfunction; frailty; age-related functional decline ("ARFD") in the elderly; growth hormone deficiency; hematopoietic disorders; hormone replacement (male and female); hyper-cholesterolemia; hyperinsulinemia; hyperlipidemia; hypertension; hyperandrogenemia; hypogonadism; hypothermia; impotence; insulin resistance; type 2 diabetes; lipodystrophy; male menopause; metabolic syndrome (syndrome X); loss of muscle strength and/or function; muscular dystrophies; muscle loss following surgery; muscular atrophy; neurodegenerative diseases; neuromuscular disease; decreased platelet count; platelet aggregation disorders; obesity; osteoporosis; osteopenia; glucocorticoid-induced osteoporosis; osteochondro-dysplasias; periodontal disease; premenstrual syndrome; postmenopausal symptoms in women; Reaven's syndrome; rheumatological disease; sarcopenia; male and female sexual dysfunction; physiological short stature; tooth damage; thrombocytopenia; vaginal dryness; atrophic vaginitis; ventricular dysfunction; and wasting. In some particular embodiments, the disease or disorder may be selected from the group consisting of: loss of muscle strength and/or function; muscular dystrophies; muscle loss following surgery; and muscular atrophy.

BRIEF DESCRIPTION OF THE DRAWINGS

FIG. 9 shows moisture sorption/desorption curves for crystalline Form C of compound of Formula (I).

FIG. 10 shows the $^{1}$H-NMR spectrum for crystalline Form C of compound of Formula (I).

DETAILED DESCRIPTION

Disclosed herein are crystalline forms of the compound of Formula (I), or solvates thereof, and methods of crystallizing the compound of Formula (I). The compound of Formula (I) is show below:

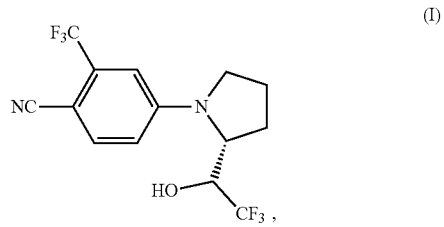 [SMILES: N#Cc1ccc(N2CCC[C@@H]2C(O)C(F)(F)F)cc1C(F)(F)F]

(I)

Crystalline forms of Formula (I), include crystalline Form C, crystalline Form E, and crystalline Form B (described herein).

The present application relates to the first crystalline forms of the compounds of Formula (I), as well as methods of crystallizing the various crystalline forms of the compounds of Formula (I). The crystalline forms advantageously exhibit improved bioavailability, stability, processability and ease of manufacture. As a result, the crystalline forms of Formula (I), particularly crystalline Form C, provide long-term stability and low adsorption and desorption of water vapor. Accordingly, the crystalline forms provide significant clinical improvements as modulators of androgen receptor activity.

The present application also relates to the method using the various crystalline forms of the compound of Formula (I), particularly crystalline Form C, for treating diseases and disorders by administering to a patient a therapeutically effective amount of a composition comprising one or more crystalline forms of a compound of Formula (I), and one or more pharmaceutically acceptable excipients.

Crystalline Forms of the Compound of Formula (I)

Disclosed herein are crystalline forms of the compound of Formula (I), and in particular crystalline Form C, crystalline Form E, and crystalline Form B. (described below). Unless otherwise stated, the X-ray powder diffraction data provided herein was determined using a Cu Kα radiation source.

Crystalline Form C

Some embodiments include an unsolvated crystalline form of Formula (I), referred to herein as crystalline Form C. The precise conditions for forming crystalline Form C may be empirically determined and it is only possible to give a number of methods which have been found to be suitable in practice.

Figure 1:
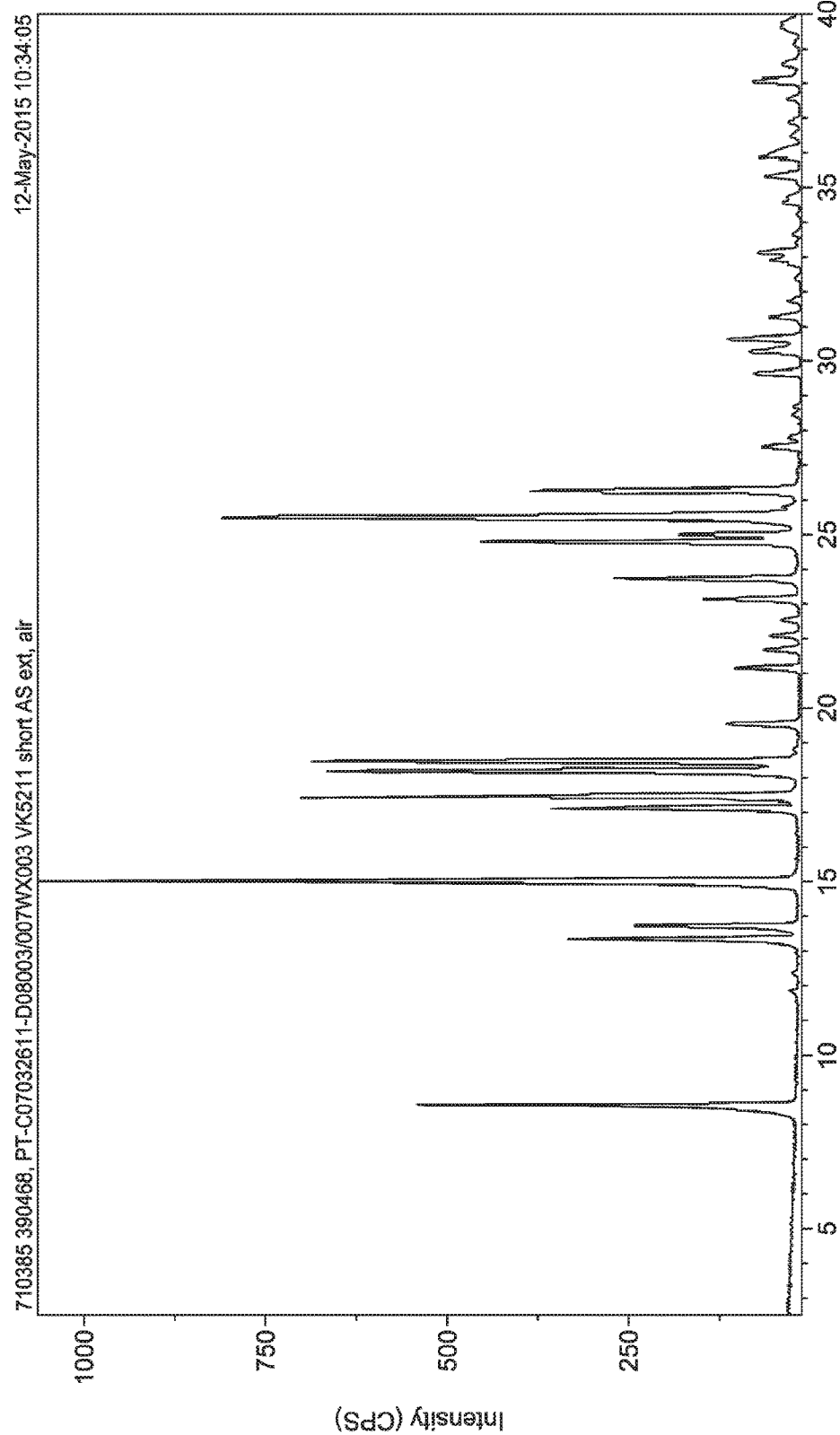
FIG. 1 is an X-ray powder diffraction pattern of crystalline Form C of Formula (I).

Crystalline Form C was characterized using various techniques which are described in further detail in the experimental methods section. FIG. 1 shows the crystalline structure of Form C as determined by X-ray powder diffraction (XRPD). Crystalline Form C, which may be obtained by the methods disclosed herein, exhibits prominent peaks at approximately 8.5, 13.3, 13.7, 15.0, 17.5, 18.2, 18.5, 19.5, 21.1, 23.1, 23.7, 25.5, and 26.2 degrees 2θ. Thus, in some embodiments, a crystalline form of the compounds of Formula (I) has at least one characteristic peak (e.g., one, two, three, four, five, six, seven, eight, nine, ten or eleven characteristic peaks) selected from approximately 8.5, 13.3, 13.7, 15.0, 17.5, 18.2, 18.5, 19.5, 21.1, 23.1, 23.7, 25.5, and 26.2 degrees 2θ. In some embodiments, a crystalline form of the compounds of Formula (I) has at least three characteristic peaks selected from approximately 8.5, 13.3, 13.7, 15.0, 17.5, 18.2, 18.5, 19.5, 21.1, 23.1, 23.7, 25.5, and 26.2 degrees 2θ.

As is well understood in the art, because of the experimental variability when X-ray diffraction patterns are measured on different instruments, the peak positions are assumed to be equal if the two theta (2θ) values agree to within a certain degree of variability. For example, the United States Pharmacopeia states that if the angular setting of the 10 strongest diffraction peaks agree to within +0.2 degrees with that of a reference material, and the relative intensities of the peaks do not vary by more than 20%, the identity is confirmed. Accordingly, in some embodiments, peak positions recited herein include variability within +0.5 degrees 2θ. In other embodiments, peak positions recited herein include variability within +0.2 degrees 2θ. As disclosed herein, the term "approximately" when referring to values of 2θ is defined as +0.5 degrees 2θ.

Figure 5:
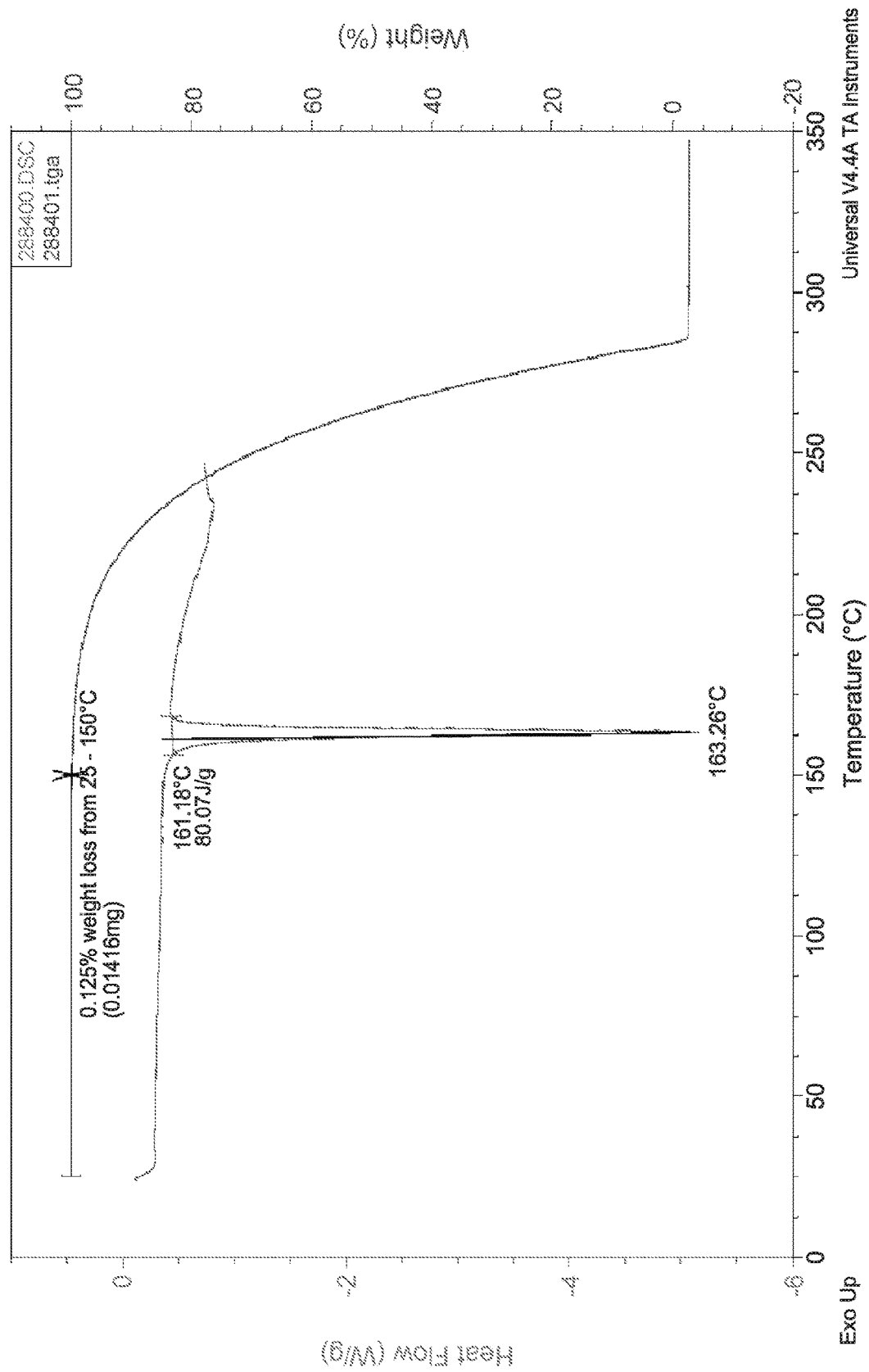
FIG. 5 shows a differential scanning calorimetry and thermogravimetric analysis overlay for crystalline Form C of compound of Formula (I).

FIG. 5 shows results obtained by differential scanning calorimetry (DSC) and thermogravimetric analysis for crystalline Form C. The DSC results indicate a peak at a temperature of about 163° C. for Crystalline Form C, which indicates the melting point for the crystal. Accordingly, in some embodiments, Crystalline Form C exhibits a melting point from about 160° C. to 166° C., from about 158° C. to about 168° C., or at about 163° C. Crystalline Form C was analysed by thermogravimetric gravimetric analysis (TG), and in one instance exhibited a 0.125% weight loss when carried out from 25° C. to 150° C. Meanwhile, FIG. 9 shows dynamic vapor sorption (DVS) results for Crystalline Form C, and shows negligible water uptake.

Crystalline Form C can therefore be characterized as non-hygroscopic and stable over a wide range of humidity. Crystal Form C also shows good crystallinity, the content of residual solvents is very low (<0.1%), the melting point is relatively high (approx. 163° C.) and crystal Form C does not show any evidence of hydrate formation.

Crystalline Form E

Some embodiments include an unsolvated crystalline form of Formula (I), referred to herein as crystalline Form E. The precise conditions for forming crystalline Form E may be empirically determined and it is only possible to give a number of methods which have been found to be suitable in practice.

Figure 2:
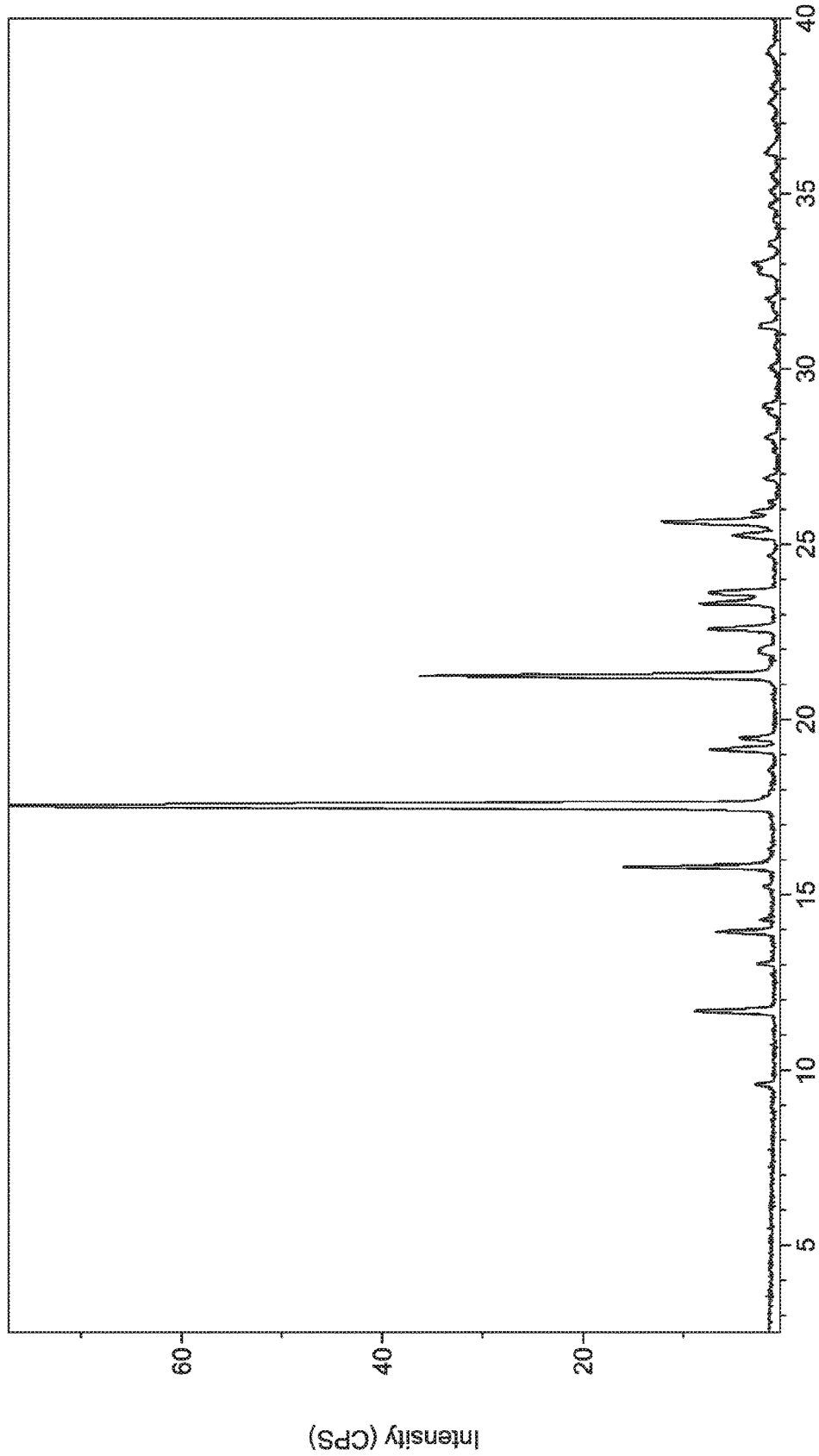
FIG. 2 is an X-ray powder diffraction pattern of crystalline Form E of Formula (I).

Crystalline Form E was characterized using various techniques which are described in further detail in the experimental methods section. FIG. 2 shows the crystalline structure of Form E as determined by X-ray powder diffraction (XRPD). Crystalline Form E, which may be obtained by the methods disclosed herein, exhibits prominent peaks at approximately 9.6, 11.7, 13.0, 13.9, 15.8, 17.5, 19.1, 19.4, 21.2, 21.9, 22.6, 23.3, 23.6, 25.3, and 25.6 degrees 2θ. Thus, in some embodiments, a crystalline form of the compounds of Formula (I) has at least one characteristic peak (e.g., one, two, three, four, five, six, seven, eight, nine, ten or eleven characteristic peaks) selected from approximately 9.6, 11.7, 13.0, 13.9, 15.8, 17.5, 19.1, 19.4, 21.2, 21.9, 22.6, 23.3, 23.6, 25.3, and 25.6 degrees 2θ. In some embodiments, a crystalline form of the compounds of Formula (I) has at least three characteristic peaks selected from approximately 9.6, 11.7, 13.0, 13.9, 15.8, 17.5, 19.1, 19.4, 21.2, 21.9, 22.6, 213, 23.6, 25.3, and 25.6 degrees 2θ.

Figure 6:
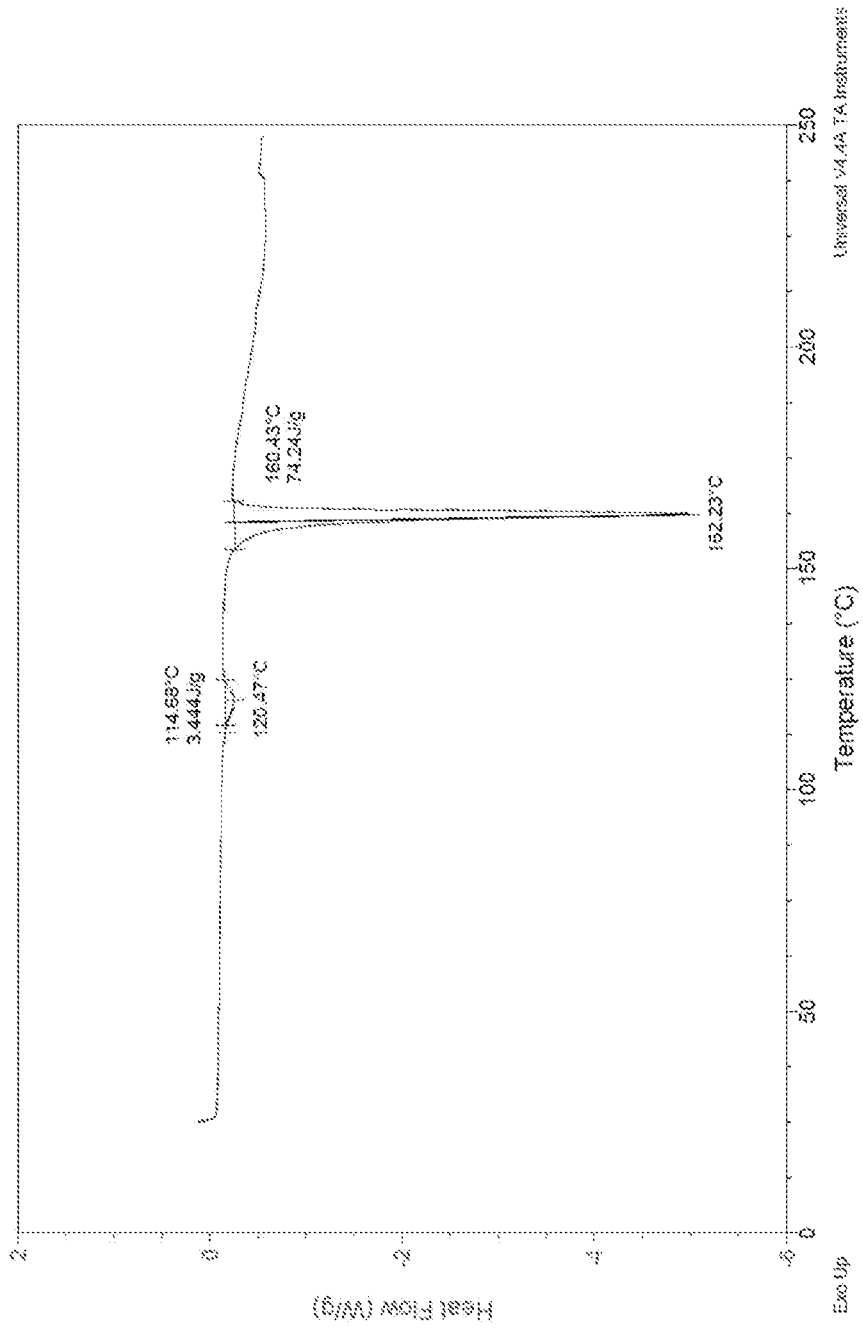
FIG. 6 shows differential scanning calorimetry results for crystalline Form E of compound of Formula (I).

FIG. 6 shows results obtained by differential scanning calorimetry (DSC) for Crystalline Form E. These results indicate a small peak at a temperature of about 120° C. and a large peak at a temperature of about 162° C. for Crystalline Form E, which indicates the melting point for the crystal. Accordingly, in some embodiments, Crystalline Form E exhibits a melting point from about 157° C. to 167° C., from about 160° C. to about 164° C., or at about 162° C.

Crystalline Form E can be characterized as slightly hygroscopic and stable over a wide range of humidity. Crystal form E also shows good crystallinity and the melting point is relatively high (approx. 162° C.).

Crystalline Form B

Some embodiments include an unsolvated crystalline form of Formula (I), referred to herein as crystalline Form B. The precise conditions for forming crystalline Form B may be empirically determined and it is only possible to give a number of methods which have been found to be suitable in practice.

Figure 4:
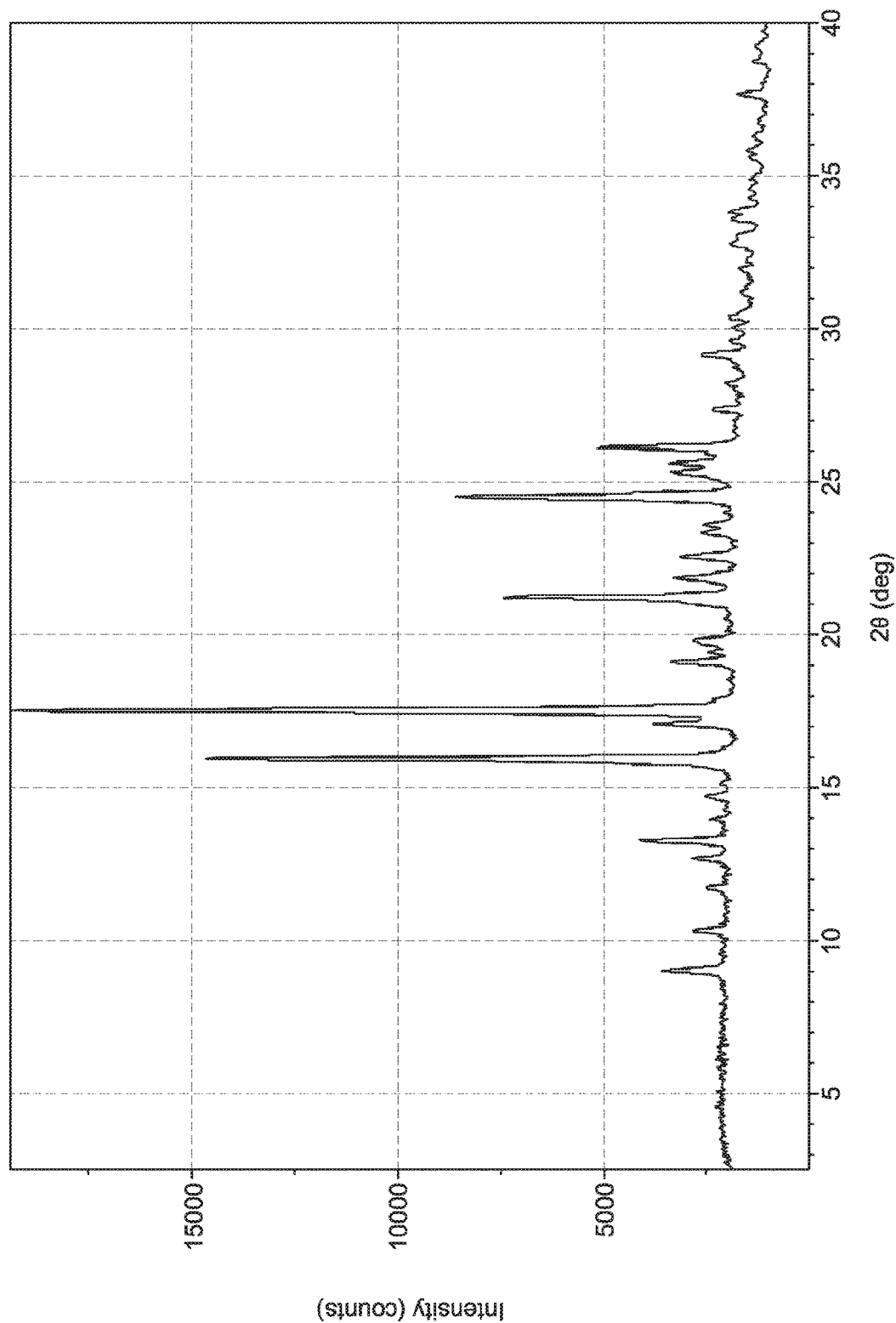
FIG. 4 is an X-ray powder diffraction pattern of crystalline Form B of Formula (I).

Samples of crystalline Form B contained small quantities of Form C and Form E. Crystalline Form B was characterized using various techniques which are described in further detail in the experimental methods section. FIG. 4 shows the crystalline structure of Form B as determined by X-ray powder diffraction (XRPD). Crystalline Form B, which may be obtained by the methods disclosed herein, exhibits prominent peaks at approximately 9.0, 10.3, 11.7, 12.7, 13.3, 16.0, 17.6, 21.3, 21.9, 22.6, 24.6, and 26.2 degrees 2θ. Thus, in some embodiments, a crystalline form of the compounds of Formula (I) has at least one characteristic peak (e.g., one, two, three, four, five, six, seven, eight, nine, ten or eleven characteristic peaks) selected from approximately 9.0, 10.3, 11.7, 12.7, 13.3, 16.0, 17.6, 21.3, 21.9, 22.6, 24.6, and 26.2 degrees 2θ. In some embodiments, a crystalline form of the compounds of Formula (I) has at least three characteristic peaks selected from approximately 9.0, 10.3, 11.7, 12.7, 13.3, 16.0, 17.6, 21.3, 21.9, 22.6, 24.6, and 26.2 degrees 2θ.

DSC results for crystalline Form B (not shown) indicate a peak at a temperature of about 159° C. for crystalline Form B, which indicates the melting point for the crystal. Accordingly, in some embodiments, crystalline Form B exhibits a melting point from about 154° C. to 164° C., from about 157° C. to about 161° C., or at about 159° C.

Crystalline Form B can therefore be characterized as stable over a wide range of humidity. Crystalline Form B also shows good crystallinity, the melting point is relatively high (approx. 159° C.) and crystal Form B does not show any evidence of hydrate formation.

Methods of Crystalizing the Compound of Formula (I)

Disclosed are methods of crystalizing the compound of Formula (I). Crystalline forms of the compound of Formula (I) may generally be obtained or produced by crystallizing the compound of Formula (I) under controlled conditions. In some embodiments, the method may produce an unsolvated crystalline form. In some embodiments, the method may produce the crystalline Form C. In some embodiments, the method may produce the crystalline Form E. In some embodiments, the method may produce the crystalline Form B. In some embodiments, the method may produce a mixture of crystalline Form C and crystalline Form E. In some embodiments, the method may produce a mixture of crystalline Form B and crystalline Form E. In some embodiments, the method may produce a mixture of crystalline Form C and crystalline Form B. In some embodiments, the method may produce a mixture of crystalline Form C, crystalline Form E, and crystalline Form B.

In some embodiments, the method may comprise dissolving an amorphous form of the compound of Formula (I) in a first solvent to create a first solution. In some embodiments, the method may comprise dissolving a crystalline form of the compound of Formula (I) in a first solvent to create a first solution. In some embodiments, the method may comprise dissolving a mixture of amorphous and crystalline forms of the compound of Formula (I) in a first solvent to create a first solution. In some embodiments, the method may comprise adding a second solvent to the first solution to create a second mixture. In some embodiments, the second solvent may comprise toluene, hexanes, or a combination thereof. In some embodiments, the method may comprise evaporating the second mixture. In some embodiments, the method may further comprise cooling the second mixture. In some embodiments, the second mixture may be cooled to 25° C., 20° C., 15° C., 10° C., 5° C., 0° C., −5° C., −10° C., −20° C., −25° C., or below.

In some embodiments, the method may comprise adding a crystalline form of the compound of Formula (I) to a solution of the compound of Formula (I) to create a seeded mixture. In some embodiments, the method may comprise adding crystalline Form C, crystalline Form B, crystalline Form E, or a combination thereof to a solution of the compound of Formula (I) to create a seeded mixture In some embodiments, the method may comprise isolating the crystalline form of the compound of Formula (I). In some embodiments, isolation may performed by filtration, such as hot-filtration. In some embodiments, the isolated product may be dried, such as by air drying.

In some embodiments, the first solvent may be a single solvent. In some embodiments, the first solvent may be a mixture of two or more solvents. In some embodiments, the first solvent may comprise acetone, acetonitrile, 1-butanol, 2-butanone, tert-butyl methyl ether, chloroform, dichloromethane, acetonitrile, diethyl ether, 1,4-dioxane, ethanol, ethyl acetate, hexafluoroisopropanol, hexanes, isopropanol, isopropyl ether, methanol, methyl isobutyl ketone, 1-propanol, tetrahydrofuran, toluene, 2,2,2-trifluoroethanol, or water.

In some embodiments, the second solvent may be a single solvent. In some embodiments, the second solvent may be a mixture of two or more solvents. In some embodiments, the first solvent may comprise acetone, acetonitrile, 1-butanol, 2-butanone, tert-butyl methyl ether, chloroform, dichloromethane, acetonitrile, diethyl ether, 1,4-dioxane, ethanol, ethyl acetate, hexafluoroisopropanol, hexanes, isopropanol, isopropyl ether, methanol, methyl isobutyl ketone, 1-propanol, tetrahydrofuran, toluene, 2,2,2-trifluoroethanol, or water. In some embodiments, the second solvent may be toluene, n-hexane, hexanes, n-pentane, pentanes, or heptane.

In some embodiments, the method may further comprise agitation. In some embodiments, agitation may be performed by stirring. In some embodiments, agitation may be performed by sonication.

In some embodiments, portions of the method may performed at the same temperature. In some embodiments, portions of the method may be performed at various temperatures. In some embodiments, portions of the method may be performed at room temperature. In some embodiments, portions of the method may be performed at −40° C. to 200° C. In some embodiments, portions of the method may be performed at −40° C. to 25° C. In some embodiments, portions of the method may be performed at −25° C. to −10° C. In some embodiments, portions of the method may be performed at 2° C. to 8° C. In some embodiments, portions of the method may be performed at 50° C. to 60° C. In some embodiments, portions of the method may be performed at 65° C. to 75° C. In some embodiments, portions of the method may be performed at 75° C. to 150° C. In some embodiments, portions of the method may include the first solution, second mixture, seeded mixture, isolation of the crystalline form, and agitation.

Formulations of Pharmaceutical Compositions

The compound of Formula (I) and crystalline forms thereof (e.g., crystalline Form C, crystalline Form E, and/or crystalline Form B disclosed herein) can be provided as combinations with other therapeutic agents or in pharmaceutical compositions. The pharmaceutical compositions provided herein include therapeutically effective amounts of one or more of the selective androgen receptor activity modulators provided herein that are useful in the prevention, treatment, or amelioration of one or more of the symptoms of diseases or disorders associated with androgen receptor activity.

The compositions provided herein may include one or more crystalline forms of the compound of Formula (I) provided herein. The compositions are formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers. Typically the compounds described above are formulated into pharmaceutical compositions using techniques and procedures well known in the art (see, e.g., Ansel, *Introduction to Pharmaceutical Dosage Forms*, 4$^{th}$ Edition (1985), 126).

In some embodiments, the composition comprising the compound of Formula (I) may include one or more crystalline forms of the compound of Formula (I). In some embodiments, the total amount of the compound of Formula (I) in the composition may include at least about 50% by weight of a crystalline form of the compound of Formula (I). In some embodiments, the total amount of compound of Formula (I) in the composition may include at least about 80% by weight of a crystalline form of the compound of Formula (I). In some embodiments, the total amount of compound of Formula (I) in the composition may include at least about 95% by weight of a crystalline form of the compound of Formula (I). In some embodiments, the total amount of compound of Formula (I) in the composition may include at least about 50% by weight of crystalline Form C. In some embodiments, the total amount of compound of Formula (I) in the composition may include at least about 80% by weight of crystalline Form C. In some embodiments, the total amount of compound of Formula (I) in the composition may include at least about 95% by weight of crystalline Form C. In some embodiments, the total amount of compound of Formula (I) in the composition may include at least about 99% by weight of crystalline Form C. In some embodiments, the compound of Formula (I) in the composition may consist essentially of a crystalline form of the compound of Formula (I). In some embodiments, the compound of Formula (I) in the composition may consist essentially of crystalline Form C. In some embodiments, the compound of Formula (I) in composition includes a mixture of at least two (e.g., two, three or four forms) of a crystalline form of compound of Formula (I), The compositions, in some embodiments, include crystalline Form C. For example, the total amount of compound of Formula (I) in the composition may include at least about 20%; at least about 50%; at least about 90%; at least about 95%; or at least about 99% of crystalline Form C. Similarly, the compositions may also include, for example, crystalline Form E. The amount of the total amount of a compound of Formula (I) in the composition may include at least about 20%; at least about 50%; at least about 90%; at least about 95%; or at least about 99% of crystalline Form E.

In certain embodiments, a pharmaceutical composition including one or more compounds provided herein is prepared using known techniques, including, but not limited to, mixing, dissolving, granulating, dragée-making, levigating, emulsifying, encapsulating, entrapping or tableting processes.

In the compositions, effective concentrations of one or more compounds or pharmaceutically acceptable derivatives is (are) mixed with a suitable pharmaceutical carrier or vehicle. The compounds can be derivatized as the corresponding salts, esters, enol ethers or esters, acids, bases, solvates, hydrates or prodrugs prior to formulation, as described above. The concentrations of the compounds in the compositions are effective for delivery of an amount, upon administration, that treats, prevents, or ameliorates one or more of the symptoms of diseases or disorders associated with androgen activity or in which androgen activity is implicated.

Typically, the compositions are formulated for single dosage administration. To formulate a composition, the weight fraction of compound is dissolved, suspended, dispersed or otherwise mixed in a selected vehicle at an effective concentration such that the treated condition is relieved or ameliorated. Pharmaceutical carriers or vehicles suitable for administration of the compounds provided herein include any such carriers known to those skilled in the art to be suitable for the particular mode of administration.

In addition, the compounds can be formulated as the sole pharmaceutically active ingredient in the composition or can be combined with other active ingredients. Liposomal suspensions, including tissue-targeted liposomes, such as tumor-targeted liposomes, also can be suitable as pharmaceutically acceptable carriers. These can be prepared according to methods known to those skilled in the art. For example, liposome formulations can be prepared as described in U.S. Pat. No. 4,522,811. Briefly, liposomes such as multilamellar vesicles (MLV's) can be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

One or more than one of the compounds provided herein is included in the pharmaceutically acceptable carrier in an amount sufficient to exert a therapeutically useful effect in the absence of undesirable side effects on the subject treated.

The concentration of the one or more than one compounds provided herein in the pharmaceutical composition will depend on absorption, inactivation and excretion rates of the compound, the physicochemical characteristics of the compound, the dosage schedule, and amount administered as well as other factors known to those of skill in the art. For example, the amount that is delivered is sufficient to ameliorate one or more of the symptoms of diseases or disorders associated with androgen activity or in which androgen activity is implicated, as described herein.

The effective amount of a compound provided herein can be determined by one of ordinary skill in the art, and includes exemplary dosage amounts for a mammal of from about 0.05 to 100 mg/kg of body weight of active compound per day, which can be administered in a single dose or in the form of individual divided doses, such as from 1 to 4 times per day. It will be understood that the specific dose level and frequency of dosage for any particular subject can be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. In some embodiments, the daily dosage of a compound provided herein can be varied over a wide range from about or 0.01 to about or 1000 mg per adult human per day. For example, dosages can range from about or 0.1 to about or 200 mg/day. In some embodiments, the dosage can range from 0.2 mg to 20 mg per day. In some embodiments, the dosage can range from 0.5 mg to 10 mg per day. In some embodiments, the daily dosage can be 0.1 mg, 0.25 mg, 0.5 mg, 0.75 mg, 1 mg, 1.25 mg, 1.5 mg, 1.75 mg, 2 mg, 2.25 mg, 2.5 mg, 2.75 mg, 3 mg, 3.25 mg, 3.5 mg, 3.75 mg, 4 mg, 4.25 mg, 4.5 mg, 4.75 mg, 5 mg, 5.25 mg, 5.5 mg, 5.75 mg, 6 mg, 6.25 mg, 6.5 mg, 6.75 mg, 7 mg, 7.25 mg, 7.5 mg, 7.75 mg, 8 mg, 8.25 mg, 8.5 mg, 8.75 mg, 9 mg, 9.25 mg, 9.5 mg, 9.75 mg, 10 mg. For oral administration, the compositions can be provided in the form of unit dosages such as tablets or capsules or liquids including from about or 0.01 to about or 1000 mg, such as for example, 0.01, 0.05, 0.075, 0.1, 0.25, 0.5, 0.75, 1, 2, 2.5, 3, 4, 5, 6, 7, 8, 9, 10, 15, 20, 25, 50, 75, 100, 125, 150, 175, 180, 190, 200, 225, 250, 300, 400, 500, 750, 800, 850, 900, 950 and 1000 milligrams of the active ingredient for the symptomatic adjustment of the dosage to the subject to be treated. In some embodiments, the compositions can be provided in the form of unit dosages such as tablets or capsules or liquids including from about or 0.01 to about or 1000 μg, such as for example, 0.01, 0.05, 0.075, 0.1, 0.25, 0.5, 0.75, 1, 2.5, 3, 4, 5, 6, 7, 8, 9, 10, 15, 20, 25, 50, 75, 100, 125, 150, 175, 180, 190, 200, 225, 250, 300, 350, 400, 450, 500, 550, 600, 650, 700, 750, 800, 850, 900, 950 and 1000 micrograms of the active ingredient for the symptomatic adjustment of the dosage to the subject to be treated.

The pharmaceutical composition including one or more than one compound provided herein can be administered at once, or can be divided into a number of smaller doses to be administered at intervals of time. It is understood that the precise dosage and duration of treatment is a function of the disease being treated and can be determined empirically using known testing protocols or by extrapolation from in vivo or in vitro test data. It is to be noted that concentrations and dosage values also can vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the compounds, compositions, methods and other subject matter provided herein.

Pharmaceutically acceptable derivatives include acids, bases, enol ethers and esters, salts, esters, hydrates, solvates and prodrug forms. The derivative is selected such that its pharmacokinetic properties are superior to the corresponding neutral compound.

Thus, effective concentrations or amounts of one or more of the compounds described herein or pharmaceutically acceptable derivatives or prodrugs thereof are mixed with a suitable pharmaceutical carrier or vehicle for systemic, topical or local administration to form pharmaceutical compositions. One or more than one compound provided herein is/are included in an amount effective for ameliorating one or more symptoms of, or for treating or preventing diseases or disorders associated with androgen receptor activity or in which androgen receptor activity is implicated, as described herein. The concentration of the one or more than one compound in the composition will depend on absorption, inactivation, excretion rates of the active compound, the dosage schedule, amount administered, particular formulation as well as other factors known to those of skill in the art.

The compositions are intended to be administered by a suitable route, including orally in the form of capsules, tablets, granules, powders or liquid formulations including syrups; parenterally, such as subcutaneously, intravenously, intramuscularly, with intersternal injection or infusion techniques (as sterile injectable aqueous (aq.) or non-aqueous solutions or suspensions); nasally, such as by inhalation spray; topically, such as in the form of a cream or ointment; rectally, such as in the form of suppositories; liposomally; and locally. The compositions can be in liquid, semi-liquid or solid form and are formulated in a manner suitable for each route of administration. In certain embodiments, administration of the formulation includes parenteral and oral modes of administration. In one embodiment, the compositions are administered orally.

In certain embodiments, the pharmaceutical compositions provided herein including one or more compounds provided herein is a solid (e.g., a powder, tablet, and/or capsule). In certain of such embodiments, a solid pharmaceutical composition including one or more compounds provided herein is prepared using ingredients known in the art, including, but not limited to, starches, sugars, diluents, granulating agents, gums, lubricants, binders, and disintegrating agents.

In certain embodiments, the pharmaceutical compositions provided herein including one or more compounds provided herein is a liquid or semi-liquid. In certain of such embodiments, a liquid pharmaceutical composition including one or more crystalline forms of the compound of Formula (I) may be prepared by dissolving the crystalline form of Formula (I) in a suitable solvent or mixtures of solvents including, but not limited to, water, methanol, ethanol, n-propanol, isopropanol, glycerol, propylene glycol, polyethylene glycol, acetone, dimethyl sulfoxide, chloroform, and isopropyl myristate. In other such embodiments, one or more crystalline forms of the compound of Formula (I) may be formulated as a suspension in a liquid dispersion medium comprising one or more liquids.

In certain embodiments, a pharmaceutical composition including one or more compounds provided herein is formulated as a depot preparation. Certain of such depot preparations are typically longer acting than non-depot preparations. In certain embodiments, such preparations are administered by implantation (for example, subcutaneously or intramuscularly) or by intramuscular injection. In certain embodiments, depot preparations are prepared using suitable polymeric or hydrophobic materials (for example, an emulsion in an acceptable oil) or ion exchange resins, or as sparingly soluble derivatives, for example, as a sparingly soluble salt.

In certain embodiments, a pharmaceutical composition including one or more compounds provided herein includes a delivery system. Examples of delivery systems include, but are not limited to, liposomes and emulsions. Certain delivery systems are useful for preparing certain pharmaceutical compositions including those including hydrophobic compounds. In certain embodiments, certain organic solvents such as dimethylsulfoxide are used.

In certain embodiments, a pharmaceutical composition including one or more compounds provided herein (active ingredient) includes one or more tissue-specific delivery molecules designed to deliver the pharmaceutical composition to specific tissues or cell types. For example, in certain embodiments, pharmaceutical compositions include liposomes coated with a tissue-specific antibody.

In certain embodiments, a pharmaceutical composition including one or more compounds provided herein includes a co-solvent system. Certain of such co-solvent systems include, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol including 3% w/v benzyl alcohol, 8% w/v of the nonpolar surfactant Polysorbate 80™, and 65% w/v polyethylene glycol 300. The proportions of such co-solvent systems can be varied considerably without significantly altering their solubility and toxicity characteristics. Furthermore, the identity of co-solvent components can be varied: for example, other surfactants can be used instead of Polysorbate 80™; the fraction size of polyethylene glycol can be varied; other biocompatible polymers can replace polyethylene glycol, e.g., polyvinyl pyrrolidone; and other sugars or polysaccharides can substitute for dextrose.

In certain embodiments, solutions or suspensions used for parenteral, intradermal, subcutaneous, or topical application can include any of the following components: a sterile diluent, such as water for injection, saline solution, fixed oil, polyethylene glycol, glycerine, propylene glycol or other synthetic solvent; antimicrobial agents, such as benzyl alcohol and methyl parabens; antioxidants, such as ascorbic acid and sodium bisulfite; chelating agents, such as ethylenediamine-tetraacetic acid (EDTA); buffers, such as acetates, citrates and phosphates; and agents for the adjustment of tonicity such as sodium chloride or dextrose. Parenteral preparations can be enclosed in ampules, disposable syringes or single or multiple dose vials made of glass, plastic or other suitable material.

In instances in which the compounds exhibit insufficient solubility, methods for solubilizing compounds can be used. Such methods are known to those of skill in this art, and include, but are not limited to, using cosolvents, such as dimethylsulfoxide (DMSO), using surfactants, such as surfactants that include polyoxyethylene derivatives of sorbitan monolaurate, such as TWEEN® or polysorbate surfactants, or dissolution in aqueous sodium bicarbonate. Derivatives of the compounds, such as prodrugs of the compounds also can be used in formulating effective pharmaceutical compositions.

In certain embodiments, a pharmaceutical composition including one or more compounds provided herein includes a sustained release system. A non-limiting example of such a sustained-release system is a semipermeable matrix of solid hydrophobic polymers. In certain embodiments, sustained release systems can, depending on their chemical nature, release compounds over a period of hours, days, weeks or months.

In certain embodiments, upon mixing or addition of the compound(s), the resulting mixture can be a solution, suspension or emulsion. The form of the resulting mixture depends upon a number of factors, including the intended mode of administration and the solubility of the compound in the selected carrier or vehicle. The effective concentration is sufficient for ameliorating the symptoms of the disease, disorder or condition treated and can be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil-water emulsions including suitable quantities of the compounds or pharmaceutically acceptable derivatives thereof. The pharmaceutically active compounds and derivatives thereof are typically formulated and administered in unit dosage forms.

The composition can include in addition to the one or more than one compound provided herein other ingredients, such as, but not limited to, a diluent such as lactose, sucrose, dicalcium phosphate, or carboxymethylcellulose; a lubricant, such as magnesium stearate, calcium stearate and talc; and a binder such as starch, natural gums, such as gum acacia, gelatin, glucose, molasses, polyvinylpyrrolidone, celluloses and derivatives thereof, povidone, crospovidones and other such binders known to those of skill in the art. Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols and ethanol, to thereby form a solution or suspension. If desired, the pharmaceutical composition to be administered also can include minor amounts of nontoxic auxiliary substances such as wetting agents, emulsifying agents, or solubilizing agents, or pH buffering agents, for example, acetate or sodium citrate, or cyclodextrin derivatives, sorbitan monolaurate, triethanolamine sodium acetate, triethanolamine oleate. Actual methods of preparing such dosage forms are known, or will be apparent, to those skilled in this art; for example, see *Remington's Pharmaceutical Sciences*, Mack Publishing Company, Easton, Pa., 15$^{th}$ edition (1975). The composition or formulation to be administered will, in any event, include a quantity of the active compound in an amount sufficient to alleviate the symptoms of the treated subject.

Dosage forms or compositions can be prepared to include one or more than one compound provided herein in the range of 0.005% to 100% with the balance made up from non-toxic carrier. For oral administration, a pharmaceutically acceptable non-toxic composition is formed by the incorporation of any of the normally employed excipients, such as, for example pharmaceutical grades of mannitol, lactose, starch, magnesium stearate, talcum, cellulose derivatives, sodium croscarmellose, glucose, sucrose, magnesium carbonate or sodium saccharin. Such compositions include solutions, suspensions, tablets, capsules, powders and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparation of these compositions are known to those skilled in the art. The contemplated compositions can include 0.001%-100% active ingredient, in one embodiment 0.1-85%, in another embodiment 75-95%. In some embodiments, the compositions include 1-10% active ingredient. In some embodiments, the compositions include 10-25% active ingredient. In some embodiments, the compositions includes 15-35% active ingredient. In some embodiments, the compositions include 40-60% active ingredient. In some embodiments, the compositions include 50-75% active ingredient. In some embodiments, the active ingredient is present at 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%.

In certain embodiments, the compounds can be administered in a form suitable for immediate release or extended release. Immediate release or extended release can be achieved with suitable pharmaceutical compositions or, particularly in the case of extended release, with devices such as subcutaneous implants or osmotic pumps. Exemplary compositions for topical administration include a topical carrier such as a mineral oil gelled with polyethylene (e.g., PLASTIBASE®).

In certain embodiments, compounds provided herein used in the pharmaceutical compositions can be provided as pharmaceutically acceptable salts with pharmaceutically compatible counter-ions. Pharmaceutically compatible salts can be formed with many acids, including, but not limited to, hydrochloric, sulfuric, acetic, citric, ascorbic, butyric, lactic, tartaric, malic, fumaric, succinic and valeric.

In certain embodiments, the pharmaceutical compositions include one or more than one compound provided herein in a therapeutically effective amount. In certain embodiments, the therapeutically effective amount is sufficient to prevent, alleviate or ameliorate symptoms of a disease or to prolong the survival of the subject being treated. Determination of a therapeutically effective amount is well within the capability of those skilled in the art.

The compositions can include in addition to the one or more than one compound provided herein other active compounds to obtain desired combinations of properties.

The compounds provided herein, or pharmaceutically acceptable derivatives or prodrugs thereof as described herein, also can be advantageously administered for therapeutic or prophylactic purposes together with another pharmacological agent known in the general art to be of value in treating one or more of the diseases or medical conditions referred to hereinabove, such as diseases or disorders associated with androgen receptor activity or in which androgen receptor activity is implicated. It is to be understood that such combination therapy constitutes a further aspect of the compositions and methods of treatment provided herein.

In certain embodiments, a pharmaceutical composition including one or more compounds provided herein is formulated as a prodrug. In certain embodiments, prodrugs are useful because they are easier to administer than the corresponding active form. For example, in certain instances, a prodrug can be more bioavailable (e.g., through oral administration) than is the corresponding active form. In certain instances, a prodrug can have improved solubility compared to the corresponding active form. In certain embodiments, a prodrug is an ester. In certain embodiments, such prodrugs are less water soluble than the corresponding active form. In certain instances, such prodrugs possess superior transmittal across cell membranes, where water solubility is detrimental to mobility. In certain embodiments, the ester in such prodrugs is metabolically hydrolyzed to carboxylic acid. In certain embodiments, a prodrug includes a short peptide (polyamino acid) bound to an acid group. In certain of such embodiments, the peptide is metabolized to form the corresponding active form.

In certain embodiments, a pharmaceutical composition including one or more compounds provided herein is useful for treating a conditions or disorder in a mammalian, and particularly in a human subject. Suitable administration routes include, but are not limited to, oral, rectal, transmucosal, intestinal, enteral, topical, suppository, through inhalation, intrathecal, intraventricular, intraperitoneal, intranasal, intraocular and parenteral (e.g., intravenous, intramuscular, intramedullary, and subcutaneous). In certain embodiments, pharmaceutical compositions are administered to achieve local rather than systemic exposures. For example, pharmaceutical compositions can be injected directly in the area of desired effect (e.g., in the renal or cardiac area). In certain embodiments in which the pharmaceutical composition is administered locally, the dosage regimen is adjusted to achieve a desired local concentration of a compound provided herein.

In certain embodiments, a pharmaceutical composition including one or more compounds provided herein is administered in the form of a dosage unit (e.g., tablet, capsule, pill, injection, bolus). In certain embodiments, such dosage units include a selective androgen receptor modulator provided herein in a dose from about or 0.01 µg/kg of body weight to about or 50 mg/kg of body weight. In certain embodiments, such dosage units include a selective androgen receptor modulator in a dose from about or 0.05 µg/kg of body weight to about or 40 mg/kg of body weight. In certain embodiments, such dosage units include a selective androgen receptor modulator in a dose from about or 0.1 µg/kg of body weight to about or 30 mg/kg of body weight. In certain embodiments, such dosage units include a selective androgen receptor modulator in a dose from about or 0.5 µg/kg of body weight to about or 25 mg/kg of body weight. In certain embodiments, such dosage units include a selective androgen receptor modulator in a dose from about or 1 µg/kg of body weight to about or 20 mg/kg of body weight. In certain embodiments, such dosage units include a selective androgen receptor modulator in a dose from about or 2 µg/kg of body weight to about or 15 mg/kg of body weight. In certain embodiments, such dosage units include a selective androgen receptor modulator in a dose from about or 10 µg/kg of body weight to about or 5 mg/kg of body weight. In certain embodiments, such dosage units include a selective androgen receptor modulator provided herein in a dose from about or 0.01 mg/kg of body weight to about or 1 mg/kg of body weight. In certain embodiments, such dosage units include a selective androgen receptor modulator in a dose from about or 0.05 mg/kg of body weight to about or 0.1 mg/kg of body weight.

In certain embodiments, such dosage units include a selective androgen receptor modulator in a dose from about or 0.001 µg/kg of body weight to about or 100 µg/kg of body weight. In certain embodiments, such dosage units include a selective androgen receptor modulator in a dose from about or 0.01 µg/kg of body weight to about or 10 µg/kg of body weight. In certain embodiments, such dosage units include a selective androgen receptor modulator in a dose from about or 0.1 µg/kg of body weight to about or 1 µg/kg of body weight. An approximate average adult body weight is 70 kg. Thus, for an adult of average body weight, a dose of 0.1 µg/kg of body weight is equivalent to 7 µg, a dose of 1 µg/kg of body weight is equivalent to 70 µg, a dose of 10 µg/kg of body weight is equivalent to 700 µg or 0.7 mg and a dose of 0.1 mg/kg of body weight is equivalent to 7 mg.

In certain embodiments, pharmaceutical compositions are administered as needed, once per day, twice per day, three times per day, or four or more times per day. It is recognized by those skilled in the art that the particular dose, frequency, and duration of administration depends on a number of factors, including, without limitation, the biological activity desired, the condition of the subject, and tolerance for the pharmaceutical composition.

In certain embodiments, a pharmaceutical composition provided herein is administered for a period of continuous therapy. For example, a pharmaceutical composition provided herein can be administered over a period of days, weeks, months, or years.

Dosage amount, interval between doses, and duration of treatment can be adjusted to achieve a desired effect. In certain embodiments, dosage amount and interval between doses are adjusted to maintain a desired concentration of compound in a subject. For example, in certain embodiments, dosage amount and interval between doses are adjusted to provide plasma concentration of a compound provided herein at an amount sufficient to achieve a desired effect. In certain of such embodiments the plasma concentration is maintained above the minimal effective concentration (MEC). In certain embodiments, pharmaceutical compositions provided herein are administered with a dosage regimen designed to maintain a concentration above the MEC for 10-90% of the time, between 30-90% of the time, or between 50-90% of the time.

Compositions for Oral Administration

In certain embodiments, oral pharmaceutical dosage forms are either solid, gel or liquid. The solid dosage forms are tablets, capsules, granules, and bulk powders. Types of oral tablets include compressed, chewable lozenges and tablets which can be enteric coated, sugar coated or film coated. Capsules can be hard or soft gelatin capsules, while granules and powders can be provided in non-effervescent or effervescent form with the combination of other ingredients known to those skilled in the art.

In certain embodiments, the formulations are solid dosage forms, such as capsules or tablets. The tablets, pills, capsules, troches and other solid dosage forms can include any of the following ingredients, or compounds of a similar nature: a binder; a diluent; a disintegrating agent; a lubricant; a glidant; a sweetening agent; and a flavoring agent.

In certain embodiments, pharmaceutical compositions for oral administration are push fit capsules made of gelatin. Certain of such push fit capsules include one or more compounds provided herein in admixture with one or more fillers such as lactose, binders such as starches, and/or lubricants such as talc or magnesium stearate and, optionally, stabilizers. In certain embodiments, pharmaceutical compositions for oral administration are soft, sealed capsules made of gelatin and a plasticizer, such as glycerol or sorbitol. In certain soft capsules, one or more compounds provided are be dissolved or suspended in suitable liquids, such as fatty oils, liquid paraffin, or liquid polyethylene glycols. In addition, stabilizers can be added.

In certain embodiments, pharmaceutical compositions are prepared for buccal administration. Certain of such pharmaceutical compositions are tablets or lozenges formulated in conventional manner. In some embodiments, the compositions are formulated as dissolvable films, such as those made with pullulan or described in the art (e.g., see U.S. Pat. Nos. 6,596,298, 7,067,116, 7,182,964 and 7,241,411).

Examples of binders for use in the compositions provided herein include microcrystalline cellulose, gum tragacanth, glucose solution, gum arabic, gelatin solution, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include croscarmellose sodium, sodium starch glycolate, alginic acid, sodium alginate, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol, xylitol and artificial sweetening agents such as saccharin. Flavoring agents include natural flavors extracted from plants such as fruits and synthetic blends of compounds which produce a pleasant sensation, such as, but not limited to peppermint and methyl salicylate, including spray dried natural and artificial flavors. Wetting agents include propylene glycol monostearate, sorbitan monooleate, diethylene glycol monolaurate and polyoxyethylene laural ether. Emetic coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

If oral administration is desired, the compound can be provided in a composition that protects it from the acidic environment of the stomach. For example, the composition can be formulated in an enteric coating that maintains its integrity in the stomach and releases the active compound in the intestine. The composition also can be formulated in combination with an antacid or other such ingredient.

When the dosage unit form is a capsule, it can include, in addition to material of the above type, a liquid carrier such as a fatty oil. In addition, dosage unit forms can include various other materials which modify the physical form of the dosage unit, for example, coatings of sugar and other enteric agents. The compounds also can be administered as a component of an elixir, suspension, syrup, wafer, sprinkle or chewing gum. A syrup can include, in addition to the active compounds, sucrose as a sweetening agent and certain preservatives, dyes and colorings and flavors.

The active materials also can be mixed with other active materials which do not impair the desired action, or with materials that supplement the desired action, such as antacids, H2 blockers (acid reducers), and diuretics.

Pharmaceutically acceptable carriers included in tablets are binders, lubricants, diluents, disintegrating agents, coloring agents, flavoring agents, and wetting agents. Enteric coated tablets, because of the enteric coating, resist the action of stomach acid and dissolve or disintegrate in the neutral or alkaline intestines. Sugar coated tablets are compressed tablets to which different layers of pharmaceutically acceptable substances are applied. Film coated tablets are compressed tablets which have been coated with a polymer or other suitable coating. Multiple compressed tablets are compressed tablets made by more than one compression cycle utilizing the pharmaceutically acceptable substances previously mentioned. Coloring agents also can be used in the above dosage forms. Flavoring and sweetening agents are used in compressed tablets, sugar coated, multiple compressed and chewable tablets. Flavoring and sweetening agents are especially useful in the formation of chewable tablets and lozenges.

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Pharmaceutically acceptable carriers used in elixirs include solvents. Syrups are concentrated aqueous solutions of a sugar, for example, sucrose, and can include a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic add, sodium benzoate and alcohol. Examples of non-aqueous liquids utilized in emulsions include mineral oil and cottonseed oil. Examples of emulsifying agents include gelatin, gum arabic, gum tragacanth, xanthan gum, propylene glycol alginate, bentonite, and surfactants such as polyoxyethylene sorbitan monooleate. Suspending agents include xanthan gum, sodium carboxymethylcellulose, pectin, tragacanth, Veegum and acacia. Diluents include lactose and sucrose. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic acids include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

For a solid dosage form, the solution or suspension, e.g., in propylene carbonate, vegetable oils or triglycerides, can be encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, can be diluted with a sufficient quantity of a pharmaceutically acceptable liquid carrier, e.g., water, to be easily measured for administration.

Alternatively, liquid or semi-solid oral formulations can be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. Nos. Re 28,819 and 4,358,603. Briefly, such formulations include, but are not limited to, those including a compound provided herein, a dialkylated mono- or poly-alkylene glycol, including, but not limited to, 1,2-dimethoxy-methane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl) acetals of lower alkyl aldehydes such as acetaldehyde diethyl acetal.

In all embodiments, tablets and capsules formulations can be coated as known by those of skill in the art in order to modify or sustain dissolution of the active ingredient. Thus, for example, they can be coated with a conventional enterically digestible coating, such as phenylsalicylate, waxes and cellulose acetate phthalate.

Exemplary compositions can include fast-dissolving diluents such as mannitol, lactose, sucrose, and/or cyclodextrins. Also included in such formulations can be high molecular weight excipients such as celluloses and microcrystalline celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., GANTREZ®); and agents to control release such as polyacrylic copolymer (e.g., CARBOPOL 934®). Lubricants, glidants, flavors, coloring agents and stabilizers also can be added for ease of fabrication and use.

In certain of such embodiments, a pharmaceutical composition for oral administration is formulated by combining one or more compounds provided herein with one or more pharmaceutically acceptable carriers. Certain of such carriers enable compounds provided herein to be formulated in dosage forms, such as tablets, pills, dragees, capsules, liquids, gels, syrups, slurries and suspensions, for oral ingestion by a subject. In certain embodiments, pharmaceutical compositions for oral use are obtained by mixing one or more compounds provided herein and one or more solid excipient. Suitable excipients include, but are not limited to, fillers, such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl cellulose, sodium carboxymethylcellulose, and/or polyvinylpyrrolidone (PVP). In certain embodiments, such a mixture is optionally ground and auxiliaries are optionally added. In certain embodiments, pharmaceutical compositions are formed to obtain tablets or dragee cores. In certain embodiments, disintegrating agents (e.g., cross linked polyvinyl pyrrolidone, agar, or alginic acid or a salt thereof, such as sodium alginate) are added.

In certain embodiments, dragee cores are provided with coatings. In certain of such embodiments, concentrated sugar solutions can be used, which can optionally include gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to tablets or dragee coatings.

In certain embodiments, a daily dosage regimen for a subject includes an oral dose of between 0.1 µg and 2000 mg of a compound provided herein. In certain embodiments, a daily dosage regimen for a subject includes an oral dose of between 1 µg and 500 mg of a compound provided herein. In certain embodiments, a daily dosage regimen for a subject includes an oral dose of between 10 µg and 100 mg of a compound provided herein. In certain embodiments, a daily dosage regimen for a subject includes an oral dose selected from among 0.01, 0.05, 0.075, 0.1, 0.25, 0.5, 0.75, 1, 2, 2.5, 3, 4, 5, 6, 7, 8, 9, 10, 15, 20, 25, 50, 75, 100, 125, 150, 175, 180, 190, 200, 225, 250, 300, 400, 500, 750, 800, 850, 900, 950 and 1000 milligrams of a compound provided herein. In certain embodiments, a daily dosage regimen is administered as a single daily dose. In certain embodiments, a daily dosage regimen is administered as two, three, four, or more than four doses.

Injectables, Solutions and Emulsions

In certain embodiments, the pharmaceutical composition is prepared for transmucosal administration. In certain of such embodiments penetrants appropriate to the barrier to be permeated are used in the formulation. Such penetrants are generally known in the art.

Parenteral administration, generally characterized by injection, either subcutaneously, intramuscularly or intravenously also is contemplated herein. Injectables can be prepared in conventional forms, either as liquid solutions or suspensions, solid forms suitable for solution or suspension in liquid prior to injection, or as emulsions. Suitable excipients are, for example, water, saline, dextrose, glycerol, mannitol, 1,3-butanediol, Ringer's solution, an isotonic sodium chloride solution or ethanol. In addition, if desired, the pharmaceutical compositions to be administered also can include minor amounts of non-toxic auxiliary substances such as wetting or emulsifying agents, pH buffering agents, stabilizers, solubility enhancers, and other such agents, such as for example, mono- or diglycerides, fatty acids, such as oleic acid, sodium acetate, sorbitan monolaurate, triethanolamine oleate and cyclodextrins. Implantation of a slow-release or sustained-release system, such that a constant level of dosage is maintained (see, e.g., U.S. Pat. No. 3,710,795) also is contemplated herein. Briefly, a compound provided herein is dispersed in a solid inner matrix, e.g., polymethyl-methacrylate, polybutylmethacrylate, plasticized or unplasticized polyvinylchloride, plasticized nylon, plasticized polyethylene-terephthalate, natural rubber, polyisoprene, polyisobutylene, polybutadiene, polyethylene, ethylene-vinylacetate copolymers, silicone rubbers, polydimethyl-siloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxy-ethanol copolymer, that is insoluble in body fluids. The compound diffuses through the outer polymeric membrane in a release rate controlling step. The percentage of active compound included in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions can be either aqueous or nonaqueous.

If administered intravenously, suitable carriers include physiological saline or phosphate buffered saline (PBS), and solutions including thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Anti-oxidants include sodium bisulfate. Local anesthetics include procaine hydrochloride. Suspending and dispersing agents include sodium carboxymethylceluose, hydroxy-propyl methylcellulose and polyvinylpyrrolidone. Emulsifying agents include Polysorbate 80 (TWEEN® 80). A sequestering or chelating agent of metal ions include EDTA. Pharmaceutical carriers also include ethyl alcohol, polyethylene glycol and propylene glycol for water miscible vehicles and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the subject or animal as is known in the art.

The unit dosage parenteral preparations are packaged in an ampoule, a vial or a syringe with a needle. All preparations for parenteral administration must be sterile, as is known and practiced in the art.

Illustratively, intravenous or intraarterial infusion of a sterile aqueous solution including an active compound is an effective mode of administration. Another embodiment is a sterile aqueous or oily solution or suspension including an active material injected as necessary to produce the desired pharmacological effect.

Injectables are designed for local and systemic administration. Typically a therapeutically effective dosage is formulated to include a concentration of at least about 0.1% w/w up to about 90% w/w or more, in some embodiments more than 1% w/w, of the active compound to the treated tissue(s). The active ingredient can be administered at once, or can be divided into a number of smaller doses to be administered at intervals of time. The precise dosage and duration of treatment is a function of the tissue being treated and can be determined empirically using known testing protocols or by extrapolation from in vivo or in vitro test data. It is to be noted that concentrations and dosage values also can vary with the age of the individual treated. It is to be further understood that for any particular subject, specific dosage regimens should be adjusted over time according to the individual need and the professional judgment of the person administering or supervising the administration of the formulations, and that the concentration ranges set forth herein are exemplary only and are not intended to limit the scope or practice of formulations provided herein.

The compounds can be formulated in any suitable vehicle or form. For example, they can be in micronized or other suitable form and/or can be derivatized to produce a more soluble active product or to produce a prodrug or for other purposes. The form of the resulting mixture depends upon a number of factors, including, for example, an intended mode of administration and the solubility of the compound in the selected carrier or vehicle. The effective concentration is sufficient for ameliorating the symptoms of the condition and can be empirically determined.

In certain embodiments, a pharmaceutical composition is prepared for administration by injection wherein the pharmaceutical composition includes a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers and/or suspending agents. Certain pharmaceutical compositions for injection are presented in unit dosage form, e.g., in ampules or in multi dose containers. Certain pharmaceutical compositions for injection are suspensions, solutions or emulsions in oily or aqueous vehicles, and can include formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions can include substances that increase the viscosity of the suspension, such as sodium carboxymethyl cellulose, sorbitol, or dextran. Optionally, such suspensions also can include suitable stabilizers or agents that increase the solubility of the compounds to allow for the preparation of highly concentrated solutions.

In certain embodiments, the pharmaceutical composition is prepared for administration by inhalation. Certain of such pharmaceutical compositions for inhalation are prepared in the form of an aerosol spray in a pressurized pack or a nebulizer. Certain of such pharmaceutical compositions include a propellant, e.g., dichlorodifluoromethane, trichlorofluoromethane, dichlorotetrafluoroethane, carbon dioxide or other suitable gas. In certain embodiments using a pressurized aerosol, the dosage unit can be determined with a valve that delivers a metered amount. In certain embodiments, capsules and cartridges for use in an inhaler or insufflator can be formulated. Certain of such formulations include a powder mixture of a compound provided herein and a suitable powder base such as lactose or starch.

In certain embodiments, the pharmaceutical compositions provided are administered by continuous intravenous infusion. In certain of such embodiments, from 0.01 µg to 500 mg of the composition is administered per day.

Lyophilized Powders

Of interest herein also are lyophilized powders, which can be reconstituted for administration as solutions, emulsions and other mixtures. They also can be reconstituted and formulated as solids or gels.

The sterile, lyophilized powder is prepared by dissolving a compound provided herein, or a pharmaceutically acceptable derivative thereof, in a suitable solvent. The solvent can include an excipient which improves the stability or other pharmacological component of the powder or reconstituted solution, prepared from the powder. Excipients that can be used include, but are not limited to, dextrose, sorbitol, fructose, corn syrup, xylitol, glycerin, glucose, sucrose or other suitable agent. The solvent also can include a buffer, such as citrate, sodium or potassium phosphate or other such buffer known to those of skill in the art at, typically, about neutral pH. Subsequent sterile filtration of the solution followed by lyophilization under standard conditions known to those of skill in the art provides the desired formulation. Generally, the resulting solution will be apportioned into vials for lyophilization. In some embodiments, each vial includes a single dosage of from 10 µg to 1000 mg. In another embodiment, each vial includes a single dosage of from 100 µg to 500 mg. In another embodiment, each vial includes a single dosage of from 0.1 mg to 50 mg. In another embodiment, each vial includes a single dosage of from 0.5 mg to 20 mg. In another embodiment, each vial includes a single dosage of 1 mg, 2 mg, 3 mg, 4 mg, 5 mg, 6 mg, 7 mg, 8 mg, 9 mg or 10 mg. In another embodiment, each vial includes multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, about 1 mg to 50 mg is added per mL of sterile water or other suitable carrier. In some embodiments, 5 mg to 35 mg is added per mL of sterile water or other suitable carrier. In other embodiments, 10 mg to 30 mg of lyophilized powder is added per mL of sterile water or other suitable carrier. The precise amount depends upon the selected compound. Such amount can be empirically determined.

Topical Administration

Topical mixtures are prepared as described for the local and systemic administration. The resulting mixture can be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration. Transdermal skin patches useful for administering the compounds disclosed herein include those well known to those of ordinary skill in that art.

The compounds or pharmaceutically acceptable derivatives thereof can be formulated as aerosols for topical application, such as by inhalation (see, e.g., U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will typically have diameters of less than 50 microns, in some embodiments less than 10 microns.

In certain embodiments, the pharmaceutical compositions for inhalation are prepared in the form of an aerosol spray in a pressurized pack or a nebulizer. Certain of such pharmaceutical compositions include a propellant, e.g., dichlorodifluoro-methane, trichlorofluoromethane, dichlorotetrafluoroethane, carbon dioxide or other suitable gas. In certain embodiments using a pressurized aerosol, the dosage unit can be determined with a valve that delivers a metered amount. In certain embodiments, capsules and cartridges for use in an inhaler or insufflator can be formulated. Certain of such formulations include a powder mixture of a compound provided herein and a suitable powder base such as lactose or starch.

Exemplary compositions for nasal aerosol or inhalation administration include solutions that can include, for example, benzyl alcohol or other suitable preservatives, absorption promoters to enhance absorption and/or bioavailability, and/or other solubilizing or dispersing agents such as those known in the art.

The compounds can be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients also can be administered. These solutions, particularly those intended for ophthalmic use, can be formulated as 0.01%-10% isotonic solutions, pH about 5-7, with appropriate salts. In certain embodiments in which the compositions is administered locally, the dosage regimen is adjusted to achieve a desired local concentration of a compound provided herein.

In certain embodiments, the pharmaceutical composition is prepared for topical administration. Certain of such pharmaceutical compositions include bland moisturizing bases, such as ointments or creams. Any of the ointment bases known in the art, including water in oil emulsion bases, oil in water emulsion bases, absorption bases, oleaginous bases and water soluble or water miscible bases can be used (e.g., see *Remington: The Science and Practice of Pharmacy,* 19th Ed. (Easton, Pa.: Mack Publishing Co., 1995) at pages 1399-1404). Oleaginous ointment bases are generally anhydrous and include, for example, vegetable oils, animal fats, and semisolid petroleum-based hydrocarbons. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin, stearic acid and polyethylene glycols of varying molecular weight. Creams are viscous liquids or semi-solid emulsions, and can be either oil-in-water or water-in-oil emulsions. Cream bases are water-washable, and contain an oil phase, an emulsifier, and an aqueous phase, which can include a fatty alcohol. The emulsifier in a cream formulation is generally a nonionic, anionic, cationic, or amphoteric surfactant. Lotions are preparations to be applied to the skin surface without friction, and often include a water or alcohol base, and include an emulsion and often solid particles (such as cocoa butter or fatty acid alcohols).

Exemplary suitable ointment bases include, but are not limited to, petrolatum, petrolatum plus volatile silicones, and lanolin. Cream bases, such as those including an emulsion of water, a mineral oil or petrolatum, one or more fatty alcohols or fatty esters, a polyoxyethylene ether or ester surfactant or polysorbate surfactant, also can be used. Exemplary suitable cream bases include, but are not limited to, cold cream (USP), hydrous lanolin and hydrophilic ointment (USP). The moisturizing bases can further contain various other emollients, emulsifiers, perfumes, colorants and preservatives.

Suitable water-in-oil emulsions are commercially available, e.g., blends of petrolatum, mineral oil, ceresin, lanolin alcohol, panthenol, glycerin and bisabolol under the designation Aquaphor™, available from Beiersdorf Futuro Inc. (Cincinnati, Ohio); blends of water, glycerin, panthenol, caprylic/capric triglyceride, dicaprylyl carbonate, octyl-dodecanol, C12-15 alkyl benzoate, dimethicone, squalane, tapioca starch, cetearyl alcohol, glyceryl stearate citrate, myristyl myristate, butylene glycol, benzyl alcohol, carbomer, phenoxyethanol, ammonium acryloyldimethyltaurateNP copolymer, sodium hydroxide, methylparaben, propylparaben, iodopropynl butylcarbamate, such as Eucerin™, available from Beiersdorf Futuro Inc. (Cincinnati, Ohio), blends of water, mineral oil, petrolatum, glycerin, isohexadecane, microcrystalline wax, lanolin alcohol, paraffin, panthenol, magnesium sulfate, decyl oleate, octyldodecanol, aluminum stearate, methylchloroisothiazolinone, methylisothiazolinone, citric acid and magnesium stearate, such as Nivea™ Cream, available from Beiersdorf Futuro Inc. (Cincinnati, Ohio).

Suitable oil-in-water emulsions are commercially available, e.g., water, mineral oil, petrolatum; sorbitol, stearic acid, lanolin, lanolin alcohol, cetyl alcohol, glyceryl stearate/PEG-100 stearate, triethanolamine, dimethicone, propylene glycol, microcrystalline wax, tri(PPG-3 myristyl ether) citrate, disodium EDTA, methylparaben, ethylparaben, propylparaben, xanthan gum, butylparaben and methyldibromo glutaronitrile, such as Lubriderm™ Cream, available from Pfizer (Morris Plains, N.J.); a blend of purified water, petrolatum, mineral oil, cetostearyl alcohol, propylene glycol, sodium laurel sulfate, isopropyl palmitate, imidazolidinyl urea, methylparaben and propylparaben, such as Dermabase™ cream, available from Paddock Industries, Inc. (Minneapolis, Minn.); and a blend of purified water, glycerin, hydrogenated polyisobutene, cetearyl alcohol and ceteareth-20, macadamia nut oil, dimethicone, tocopheryl acetate, stearoxytrimethylsilane (and) stearyl alcohol, panthenol, farnesol, benzyl alcohol, phenoxyethanol, acrylates/C10-30 alkyl acrylate crosspolymer, sodium Hydroxide and citric acid, such as Cetaphil™ lotion, available from Galderma Laboratories (Ft. Worth, Tex.).

In certain embodiments, the formulation, route of administration and dosage for the pharmaceutical composition provided herein can be chosen in view of a particular subject's condition (see e.g., Fingl et al., "The Pharmacological Basis of Therapeutics", Chapter 1, p. 1 (1975)). In certain embodiments, the pharmaceutical composition is administered as a single dose. In certain embodiments, a pharmaceutical composition is administered as a series of two or more doses administered over one or more days.

Compositions for Other Routes of Administration

In certain embodiments, the pharmaceutical composition is prepared for topical administration such as rectal administration. The pharmaceutical dosage forms for rectal administration include, but are not limited to rectal suppositories, capsules and tablets for systemic effect. In certain embodiments, a pharmaceutical agent is prepared for rectal administration, such as a suppositories or retention enema. Certain of such pharmaceutical agents include known ingredients, such as cocoa butter and/or other glycerides. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, Carbowax (polyoxyethylene glycol) and appropriate mixtures of mono-, di- and triglycerides of fatty acids. Combinations of the various bases can be used. In certain embodiments, the pharmaceutical compositions include moisturizing bases, such as ointments or creams. Agents to raise the melting point of suppositories include spermaceti and wax. Rectal suppositories can be prepared either by the compressed method or by molding. The typical weight of a rectal suppository is about 2 to 3 gm.

Tablets and capsules for rectal administration are manufactured using the same pharmaceutically acceptable substances and by the same methods as for formulations for oral administration.

Methods of Treatment Using Crystalline Forms of the Compound of Formula (I) and Compositions Thereof Methods of use of the compounds and compositions provided herein also are provided. The methods include in vitro and in vivo uses of the compounds and compositions for altering androgen receptor activity and for treatment, prevention, or amelioration of one or more symptoms of diseases or disorder that are modulated through androgen receptor activity, or in which androgen receptor activity is implicated. In certain embodiments, provided herein are methods of treating a subject by administering a compound provided herein. In certain embodiments, such subject exhibits symptoms or signs of a androgen receptor mediated condition. In certain embodiments, a subject is treated prophylactically to reduce or prevent the occurrence of a condition.

The crystalline forms of the compound of Formula (I) or a solvate thereof may be formulated into a composition for administering to a subject in need thereof. For example, in one embodiment, one or more crystalline forms of the compound of Formula (I) or a solvate thereof may be combined with one or more excipients into a solid formulation for administering to a subject in need thereof. In other embodiments, one or more crystalline forms of the compound of Formula (I) or a solvate thereof may be formulated into a liquid composition for administering to a subject in need thereof. In some such embodiments, the one or more crystalline forms of the compound of Formula (I) or a solvate thereof may be dissolved in one or more liquid solvents to form a solution for administering to a subject in need thereof. In other such embodiments, the one or more crystalline forms of the compound of Formula (I) or a solvate thereof may be dispersed in one or more liquids to form a suspension for administering to a subject in need thereof.

The compositions provided herein can be used in the treatment of a variety of conditions. For example, a composition comprising one or more crystalline forms of the compound of Formula (I) or a solvate thereof can be used to treat a condition including, but not limited to, maintenance of muscle strength and function (e.g., in the elderly); reversal or prevention of frailty or age-related functional decline ("ARFD") in the elderly (e.g., sarcopenia); treatment of catabolic side effects of glucocorticoids; prevention and/or treatment of reduced bone mass, density or growth (e.g., osteoporosis and osteopenia); treatment of chronic fatigue syndrome (CFS); chronic myalgia; treatment of acute fatigue syndrome and muscle loss following elective surgery (e.g., post-surgical rehabilitation); accelerating of wound healing; accelerating bone fracture repair (such as accelerating the recovery of hip fracture patients); accelerating healing of complicated fractures, e.g. distraction osteogenesis; in joint replacement; prevention of post-surgical adhesion formation; acceleration of tooth repair or growth; maintenance of sensory function (e.g., hearing, sight, olfaction and taste); treatment of periodontal disease; treatment of wasting secondary to fractures and wasting in connection with chronic obstructive pulmonary disease (COPD), chronic liver disease, AIDS, weightlessness, cancer cachexia, burn and trauma recovery, chronic catabolic state (e.g., coma), eating disorders (e.g., anorexia) and chemotherapy; treatment of cardiomyopathy; treatment of thrombocytopenia; treatment of growth retardation in connection with Crohn's disease; treatment of short bowel syndrome; treatment of irritable bowel syndrome; treatment of inflammatory bowel disease; treatment of Crohn's disease and ulcerative colitis; treatment of complications associated with transplantation; treatment of physiological short stature including growth hormone deficient children and short stature associated with chronic illness; treatment of obesity and growth retardation associated with obesity; treatment of anorexia (e.g., associated with cachexia or aging); treatment of hypercortisolism and Cushing's syndrome; Paget's disease; treatment of osteoarthritis; induction of pulsatile growth hormone release; treatment of osteochondro-dysplasias; treatment of depression, nervousness, irritability and stress; treatment of reduced mental energy and low self-esteem (e.g., motivation/assertiveness); improvement of cognitive function (e.g., the treatment of dementia, including Alzheimer's disease and short term memory loss); treatment of catabolism in connection with pulmonary dysfunction and ventilator dependency; treatment of cardiac dysfunction (e.g., associated with valvular disease, myocardial infarction, cardiac hypertrophy or congestive heart failure); lowering blood pressure; protection against ventricular dysfunction or prevention of reperfusion events; treatment of adults in chronic dialysis; reversal or slowing of the catabolic state of aging; attenuation or reversal of protein catabolic responses following trauma (e.g., reversal of the catabolic state associated with surgery, congestive heart failure, cardiac myopathy, burns, cancer, COPD); reducing cachexia and protein loss due to chronic illness such as cancer or AIDS; treatment of hyperinsulinemia including nesidioblastosis; treatment of immunosuppressed subjects; treatment of wasting in connection with multiple sclerosis or other neurodegenerative disorders; promotion of myelin repair; maintenance of skin thickness; treatment of metabolic homeostasis and renal homeostasis (e.g., in the frail elderly); stimulation of osteoblasts, bone remodeling and cartilage growth; regulation of food intake; treatment of insulin resistance, including NIDDM, in mammals (e.g., humans); treatment of insulin resistance in the heart; improvement of sleep quality and correction of the relative hyposomatotropism of senescence due to high increase in REM sleep and a decrease in REM latency; treatment of hypothermia; treatment of congestive heart failure; treatment of lipodystrophy (e.g., in subjects taking HIV or AIDS therapies such as protease inhibitors); treatment of muscular atrophy (e.g., due to physical inactivity, bed rest or reduced weight-bearing conditions); treatment of musculoskeletal impairment (e.g., in the elderly); improvement of the overall pulmonary function; treatment of sleep disorders; and the treatment of the catabolic state of prolonged critical illness; treatment of hirsutism, acne, seborrhea, androgenic alopecia, anemia, hyperpilosity, benign prostate hypertrophy, adenomas and neoplasias of the prostate (e.g., advanced metastatic prostate cancer) and malignant tumor cells containing the androgen receptor, such as is the case for breast, brain, skin, ovarian, bladder, lymphatic, liver and kidney cancers; cancers of the skin, pancreas, endometrium, lung and colon; osteosarcoma; hypercalcemia of malignancy; metastatic bone disease; treatment of spermatogenesis, endometriosis and polycystic ovary syndrome; counteracting preeclampsia, eclampsia of pregnancy and preterm labor; treatment of premenstrual syndrome; treatment of vaginal dryness; age related decreased testosterone levels in men, male menopause, hypogonadism, male hormone replacement, male and female sexual dysfunction (e.g., erectile dysfunction, decreased sex drive, sexual well-being, decreased libido), male and female contraception, hair loss, Reaven's Syndrome and the enhancement of bone and muscle performance/strength.

In certain embodiments, provided are methods for treating a subject by administering a composition comprising one or more crystalline forms of the compound of Formula (I) or a solvate thereof. Exemplary conditions that can be treated with the selective androgen receptor modulators provided herein include, but are not limited to, hypogonadism, wasting diseases, cancer cachexia, frailty, infertility, osteoporosis, hirsutism, acne, male-pattern baldness, prostatic hyperplasia, and cancer, including, but not limited to, various hormone-dependent cancers, including, without limitation, prostate and breast cancer. In certain embodiments, a selective androgen receptor agonist or partial agonist is used for male hormone replacement therapy. In certain embodiments, one or more selective androgen receptor agonists and/or partial agonists are used to stimulate hematopoiesis. In certain embodiments, a selective androgen receptor agonist or partial agonist is used as an anabolic agent. In certain embodiments, a selective androgen receptor agonist and/or partial agonist is used to improve athletic performance.

In another embodiment, a composition comprising one or more crystalline forms of the compound of Formula (I) or a solvate thereof is administered to a subject in order to treat a condition responsive to an AR modulator compound. The method includes administering to a subject having a condition responsive to an AR modulator compound a therapeutically effective amount of one or more than one compound provided herein to treat the condition responsive to an AR modulator compound. In some embodiments, the condition is treated by agonizing the androgen receptor. In some embodiments, the condition is treated by antagonizing the androgen receptor. In various embodiments, the condition treated is selected from among hypogonadism, lower than normal testosterone plasma levels, infertility, sexual arousal disorder, disorders of libido, muscle wasting, cachexia, sarcopenia, frailty, bone density loss, mood disorders (including lack of well being, lack of vigor, anger, irritability, sadness, tiredness, nervousness and depression), impaired cognitive function (including verbal fluency and spatial memory), neurodegenerative disorders, including Alzheimer's disease, mild cognition impairment, Lewis body dementia, and frontal temporal dementia, xerophthalmia, metabolic disorders, including dyslipidemia, atherosclerosis, and non-insulin dependent diabetes (NIDDM), cardiovascular disorders including but not limited to hypertension, coronary artery disease, and myocardial perfusion, obesity, anemia, prostate cancer, and schizophrenia. In other embodiments, a composition comprising one or more crystalline forms of the compound of Formula (I) or a solvate thereof can be administered to a subject in order to prevent a condition in the subject. In various embodiments, the condition prevented includes bone density loss, xerophthalmia, metabolic disorders, including dyslipidemia, atherosclerosis, and non-insulin dependent diabetes (NIDDM), cardiovascular disorders including hypertension, coronary artery disease, and myocardial perfusion, obesity and prostate cancer.

In certain embodiments, a composition comprising one or more crystalline forms of the compound of Formula (I) or a solvate thereof is used to treat acne, male-pattern baldness, wasting diseases, hirsutism, hypogonadism, osteoporosis, infertility, impotence, obesity, and cancer. In certain embodiments, one or more compounds provided herein are used to stimulate hematopoiesis. In certain embodiments, one or more compounds provided herein are used for contraception.

In certain embodiments, provided herein are methods for treating a subject having a condition caused by androgen deficiency or a condition ameliorated by androgen replacement. The methods include administering to the subject a therapeutically effective amount of a composition comprising one or more crystalline forms of the compound of Formula (I) or a solvate thereof, and thereby treating the condition. In certain embodiments, the condition is selected from among abdominal obesity, Alzheimer's disease, anemia, an arthritic condition, atherosclerosis, benign prostatic hyperplasia (BPH), cancer cachexia, cognitive decline, depression, metabolic syndrome, a muscular dystrophy, obesity, osteopenia, osteoporosis, a periodontal disease, prostate cancer, sexual dysfunction, sleep apnea, type II diabetes, bone fracture, frailty, wasting, aging skin, hypogonadism, post-menopausal symptoms in women, female sexual dysfunction, premature ovarian failure, atherosclerosis, hypercholesterolemia, hyperlipidemia, aplastic anemia and other hematopoietic disorders, pancreatic cancer, renal cancer, arthritis and joint repair.

Methods of Treating Muscle Wasting

In certain embodiments, provided herein are methods of treating, preventing, suppressing, inhibiting or reducing the incidence of muscle wasting in a subject. The methods include administering to the subject a composition comprising one or more crystalline forms of the compound of Formula (I) or a solvate thereof, in an amount effective to treat, prevent, suppress, inhibit or reduce muscle wasting in the subject. In some embodiments, the muscle wasting is caused by a condition selected from among andropause, a spinal muscular atrophy, a muscular dystrophy, myasthenia gravis, AIDS cachexia, cardiac cachexia, cancer cachexia, cancer, Chronic Obstructive Pulmonary Disease (COPD), emphysema, diabetes, HIV infection, acquired immunodeficiency syndrome (AIDS), sepsis, tuberculosis, renal failure, heart failure, cardiomyopathy, bed rest, disuse, inactivity, microgravity, malnutrition, sarcopenia and aging. In some embodiments, the composition comprising one or more crystalline forms of the compound of Formula (I) or a solvate thereof is orally administered to the subject. In one method, the compounds provided herein are used in a method for the treatment of muscular dystrophy, sarcopenia and frailty. In one embodiment, the methods include co-administering one or more than one compound provided herein with one or more agents selected from among interleukin-10 (IL-10), interleukin-4 (IL-4), a TNF inhibitor, fluorinated 4-azasteroid derivatives, glial growth factors, acetylcholine receptor inducing activity (ARIA), heregulins, neu differentiation factor, and neuregulins (e.g., see U.S. Pat. Nos. 6,444,642 and 7,037,888).

In one embodiment, provided herein are methods of treating a muscle-wasting condition associated with chronic illness. The methods include administering to the subject a composition comprising one or more crystalline forms of the compound of Formula (I) or a solvate thereof, in an amount effective to treat the muscle-wasting condition. In one embodiment, provided herein are methods for preventing a muscle wasting disorder in a subject, which include administering to the subject a composition comprising one or more crystalline forms of the compound of Formula (I) or a solvate thereof, in an amount effective to preventing a muscle wasting disorder in the subject. In one embodiment, provided herein are methods for suppressing a muscle wasting disorder in a subject, which include administering to the subject a composition comprising one or more crystalline forms of the compound of Formula (I) or a solvate thereof, in an amount effective to suppress the muscle wasting disorder in a subject. In one embodiment, provided herein are methods for reducing the incidence of a muscle wasting disorder in a subject, which include administering to the subject a composition comprising one or more crystalline forms of the compound of Formula (I) or a solvate thereof, in an amount effective to suppress the muscle wasting disorder in a subject.

Methods for identifying a subject in need of treatment for a muscular wasting disease are known in the art. For example, a subject in need of treatment for a muscular wasting disease will often generate less electrical activity during muscle contraction as compared to a healthy subject and this can be detected by electromyography. Alternative methods for diagnosis include, for example, blood tests and muscle biopsies. Suitably, blood tests can be run to determine the levels of various constituents of muscle and muscle fibers. For example, many muscular wasting diseases can be diagnosed by conducting a blood test to measure the level of creatinine in the blood. Creatinine is a breakdown product of creatine, which is an important constituent of muscle. Blood tests for determining the amount of creatine phosphokinase (CPK), which is an enzyme found predominantly in the heart, brain, and skeletal muscle, can be conducted to diagnose a subject in need for treatment of a muscular wasting disease. Specifically, when the total CPK level is substantially elevated, it usually indicates injury or stress to one or more of the heart, brain, and skeletal muscle. Subjects that may be affected by either Duchenne muscular dystrophy or Becker muscular dystrophy can be diagnosed by measuring the level of dystrophin. Typically, in subjects with either Duchenne muscular dystrophy or Becker muscular dystrophy, the level of dystrophin is deficient; but, in a subject with Duchenne muscular dystrophy, the level is more severely deficient.

Muscle biopsies also can be used to identify a subject in need of treatment for a muscular wasting disease. Generally, during a muscle biopsy, a small piece of muscle tissue is removed surgically for laboratory analysis. The analysis can reveal abnormalities in the muscle, such as inflammation, damage, or infection. The subject also can be diagnosed for a muscular wasting disease using magnetic resonance imagining (MRI). During an MRI, cross-sectional images of muscle are generated by a magnetic field and radio waves. Similar to the muscle biopsy analysis, the image generated by an MRI can reveal abnormalities in the muscle, such as inflammation, damage, or infection.

Methods of Improving Muscle Performance, Size and/or Strength

In certain embodiments, provided herein are methods of increasing muscle performance, muscle size, muscle strength, or any combination thereof in a subject. The methods include administering to the subject a composition comprising one or more crystalline forms of the compound of Formula (I) or a solvate thereof, in an amount effective to increase muscle performance, muscle size, and/or muscle strength in the subject.

In some embodiments, provided herein are methods of activating the function of the androgen receptor muscle tissue and blocking or inhibiting the function of the androgen receptor in the prostate of a male individual or in the uterus of a female individual. The methods include administering to the subject a composition comprising one or more crystalline forms of the compound of Formula (I) or a solvate thereof, in an amount effective to activate the function of the androgen receptor in muscle tissue and to block or inhibit the function of the androgen receptor in the prostate of a male individual or in the uterus of a female individual.

Methods of Improving Athletic Performance

In certain embodiments, a composition comprising one or more crystalline forms of the compound of Formula (I) or a solvate thereof is used to improve athletic performance. The methods include administering a composition comprising one or more crystalline forms of the compound of Formula (I) or a solvate thereof in a therapeutically effective amount to improve athletic performance. In some embodiments, one or more compounds provided herein are used, for example, to shorten the time normally needed to recover from physical exertion or to increase muscle strength. Athletes to whom one or more compounds provided herein can be administered include, but are not limited to, horses, dogs and humans. In certain embodiments, a composition comprising one or more crystalline forms of the compound of Formula (I) or a solvate thereof is administered to an athlete engaged in a professional or recreational competition, including, but not limited to weight-lifting, body-building, track and field events, and any of various team sports.

Methods of Treating Bone-Related Conditions

In certain embodiments, provided herein are methods of treating, preventing, suppressing, inhibiting or reducing the incidence of osteoporosis, osteopenia, glucocorticoid-induced osteoporosis or bone fracture in a subject. The methods include administering to the subject a composition comprising one or more crystalline forms of the compound of Formula (I) or a solvate thereof, in an amount effective to treat osteoporosis, osteopenia, glucocorticoid-induced osteoporosis or bone fracture in the subject. In one embodiment, the composition comprising one or more crystalline forms of the compound of Formula (I) or a solvate thereof is co-administered with an effective amount of at least one other therapeutic agent, such as an estrogen or estrogen derivatives, alone or in combination with progestin or progestin derivatives; a bisphosphonate; an anti-estrogen; a selective estrogen receptor modulators (SERM); an $\alpha_v\beta_3$ integrin receptor antagonist; a cathepsin inhibitor; a proton pump inhibitor; a PPAR$\gamma$ inhibitor; calcitonin; and osteoprotegerin. In one embodiment, the method is for the treatment of osteoporosis. In one embodiment, the method is for the treatment of osteopenia. In one embodiment, the method is for the treatment of glucocorticoid-induced osteoporosis. In one embodiment, the method is for the treatment of bone fracture.

In some embodiments, provided herein are methods of activating the function of the androgen receptor in bone tissue and blocking or inhibiting the function of the androgen receptor in the prostate of a male individual or in the uterus of a female individual. The methods include administering to the subject a composition comprising one or more crystalline forms of the compound of Formula (I) or a solvate thereof, in an amount effective to activate the function of the androgen receptor in bone tissue and to block or inhibit the function of the androgen receptor in the prostate of a male individual or in the uterus of a female individual.

In certain embodiments, provided herein are methods of increasing the strength of, or mass of a bone of a subject, or for promoting bone formation in a subject. The methods include administering a composition comprising one or more crystalline forms of the compound of Formula (I) or a solvate thereof in an amount effective to increase the strength of, or mass of a bone of a subject, or to promote bone formation in a subject.

In some embodiments, provided herein are methods for preventing a bone-related disorder in a subject, which include administering a composition comprising one or more crystalline forms of the compound of Formula (I) or a solvate thereof in an amount effective to prevent the bone-related disorder in the subject. In some embodiments, provided herein are methods for suppressing a bone-related disorder in a subject, which include administering a composition comprising one or more crystalline forms of the compound of Formula (I) or a solvate thereof in an amount effective to suppress the bone-related disorder in the subject. In some embodiments, provided herein are methods for inhibiting a bone-related disorder in a subject, which include administering a composition comprising one or more crystalline forms of the compound of Formula (I) or a solvate thereof in an amount effective to inhibit the bone-related disorder in the subject.

In one embodiment, the bone-related disorder is osteoporosis. In another embodiment, the bone-related disorder is osteopenia, In another embodiment, the bone-related disorder is increased bone resorption. In another embodiment, the bone-related disorder is bone fracture. In another embodiment, the bone-related disorder is bone frailty. In another embodiment, the bone-related disorder is any combination of osteoporosis, osteopenia, increased bone resorption, bone fracture and bone frailty.

In one embodiment, the osteoporosis results from androgen deprivation. In another embodiment, the osteoporosis follows androgen deprivation. In another embodiment, the osteoporosis is primary osteoporosis. In another embodiment, the osteoporosis is secondary osteoporosis. In another embodiment, the osteoporosis is postmenopausal osteoporosis. In another embodiment, the osteoporosis is juvenile osteoporosis. In another embodiment, the osteoporosis is idiopathic osteoporosis. In another embodiment, the osteoporosis is senile osteoporosis.

Methods of Treating Cancer

In certain embodiments, a composition comprising one or more crystalline forms of the compound of Formula (I) or a solvate thereof is used for treating, preventing, suppressing, inhibiting or reducing the incidence of cancer in a subject. Certain exemplary cancers include, but are not limited to, breast cancer, colorectal cancer, gastric carcinoma, glioma, head and neck squamous cell carcinoma, skin cancer, papillary renal carcinoma, leukemia, lymphoma, Li-Fraumeni syndrome, malignant pleural mesothelioma, melanoma, multiple myeloma, non-small cell lung cancer, synovial sarcoma, thyroid carcinoma, transitional cell carcinoma of urinary bladder, and prostate cancer, including, but not limited to prostatic hyperplasia. The methods include administering one or more compounds provided herein in a therapeutically effective amount to treat the cancer. In one embodiment, administration of the one or more than one compound provided herein to a subject afflicted with a cancerous condition alleviates the cancerous condition by killing the cancerous cells. In one embodiment, administration of the one or more than one compound provided herein to a subject afflicted with a cancerous condition results in the inhibition of growth and/or metastasis of the cancer.

In some embodiments, a composition comprising one or more crystalline forms of the compound of Formula (I) or a solvate thereof is administered in combination with one or more other therapeutic agents, such as, but not limited to, anti-proliferative agents, such as paclitaxel, a paclitaxel derivative, taxanes and vinca alkaloids, anti-tumor agents, such as mitomycin C or doxorubicin, hormones and antagonists, such as adreno-corticosteroids (prednisone), progestins (hydroxyprogesterone caproate, medroprogesterone acetate and megestrol acetate), estrogens (diethylstilbestrol and ethinyl estradiol), antiestrogens (tamoxifen), and androgens (testosterone propionate and fluoxymesterone), radionuclides, toxins and cytotoxic drugs, boron addends, chemotherapy agents, photodynamic therapy dyes, and antibiotics or combinations thereof to treat cancer. Many toxins and cytotoxic drugs are known in the art that have cytotoxic effects on cells, any of which can be used in connection with the methods provided herein. Examples of known cytotoxic agents useful in the present methods are listed, for example, in Goodman et al., "The Pharmacological Basis of Therapeutics," Sixth Edition, A. G. Gilman et al., eds., Macmillan Publishing Co., New York (1980). These include, but are not limited to, adrenocortical suppressants, such as mitotane; alkyl sulfonates, such as busulfan; ethylenimine derivatives, such as thiotepa; nitrosoureas, such as carmustine, lomustine, semustine and streptozocin; folic acid analogs, such as methotrexate; methyl hydrazine derivatives, such as procarbazine; nitrogen mustards, such as mechlorethamine, cyclophosphamide, melphalan, uracil mustard and chlorambucil; purine analogs, such as mercaptopurine and thioguanine; pyrimidine analogs, such as fluorouracil, cytarabine and azaribine; substituted urea compounds, such as hydroxyurea; taxol; triazenes, such as dacarbazine; and vinca alkaloids, such as vinblastine and vincristine.

Any antibiotic known in the art, such as aminoglycosides, bleomycin, cephalosporins and other beta-lactam antibiotics, chloramphenicol, clindamycin, dactinomycin, daunorubicin, doxorubicin, fusidic acid, macrolides, metronidazole, mithramycin, mitomycin, mupirocin, penicillins, rifamycins, sulfonamides, tetracyclines, trimethoprim and beta-lactam inhibitors, can be included in the formulation. Drugs that interfere with intracellular protein synthesis also can be used in the methods provided herein; such drugs are known to those skilled in the art and include puromycin, cycloheximide, and ribonuclease.

The methods provided herein also can include administration of a composition comprising one or more crystalline forms of the compound of Formula (I) or a solvate thereof in combination with dyes used photodynamic therapy for the treatment of cancer, and used in conjunction with appropriate non-ionizing and ionizing radiation. The use of porphyrins and other dyes used in photodynamic therapy can be used in the methods herein. Photodynamic therapy for the treatment of cancer is well known in the art (e.g., see U.S. Pat. Nos. 7,018,395, 7,011,812, 6,806,284, 6,723,750, 6,710,066, 6,630,128 and 6,622,729).

Methods of Treating Prostate Cancer

In certain embodiments, provided herein are methods for treating, preventing, suppressing, inhibiting or reducing the incidence of prostate cancer in a subject. The methods include administering a composition comprising one or more crystalline forms of the compound of Formula (I) or a solvate thereof in a therapeutically effective amount to treat the cancer. In some embodiments, the prostate cancer is androgen dependant prostate cancer. In certain embodiments, the prostate cancer is androgen independent prostate cancer. In certain embodiments, the prostate cancer is androgen independent, but androgen receptor dependant prostate cancer. In some embodiments, administration of the one or more than one compound provided herein to a subject afflicted with prostate cancer alleviates the prostate cancer by killing the cancerous cells. In one embodiment, administration of the one or more than one compound provided herein to a subject afflicted with prostate cancer results in the inhibition of growth and/or metastasis of the prostate cancer. In some embodiments, the a composition comprising one or more crystalline forms of the compound of Formula (I) or a solvate thereof is co-administered with another therapeutic agent, including, but not limited to, flutamide, bicalutamide and nilutamide, anti-tumor agent, such as toxins and cytotoxic drugs, which can be selectively targeted to react with prostate tumors by conjugating to a prostate tumor antigen, and radionuclides.

In certain embodiments, methods are provided for delaying the progression of prostate cancer in a subject suffering from prostate cancer. The methods include administering to the subject a composition comprising one or more crystalline forms of the compound of Formula (I) or a solvate thereof, in an amount effective to delay the progression of prostate cancer in the subject.

Methods of Treating Prostate Cancer

In certain embodiments, provided herein are methods for providing contraception in a subject. The methods include administering to the subject a composition comprising one or more crystalline forms of the compound of Formula (I) or a solvate thereof, in an amount effective to provide contraception in the subject. In some embodiments, provided herein are methods for providing contraception in a male subject. The methods include administering to the subject a composition comprising one or more crystalline forms of the compound of Formula (I) or a solvate thereof, in an amount effective to suppress sperm production in the subject, thereby effecting contraception in the subject. In one embodiment, the compounds provided herein inhibit spermatogenesis in a subject. In one embodiment, the method includes co-administering a composition comprising one or more crystalline forms of the compound of Formula (I) or a solvate thereof with an androgen, such as 19-nortestosterone, 7α-methyl-19-nortestosterone and 5α-dihydro-testosterone. In one embodiment, the method includes co-administration of a composition comprising one or more crystalline forms of the compound of Formula (I) or a solvate thereof that is an AR antagonist with testosterone.

Methods of Providing Hormone Therapy

In certain embodiments, provided herein are methods for providing hormone therapy to a subject. The method includes administering to the subject a composition comprising one or more crystalline forms of the compound of Formula (I) or a solvate thereof, in an amount effective to modulate androgen receptor activity, and thereby effect a change in an androgen-dependent condition.

Methods of Treating Postmenopausal Conditions

In certain embodiments, provided herein are methods for treating, preventing, suppressing, inhibiting or reducing the incidence of postmenopausal conditions in a subject. The methods include administering to the subject a composition comprising one or more crystalline forms of the compound of Formula (I) or a solvate thereof, in an amount effective to treat the postmenopausal condition. In one embodiment, the postmenopausal condition treated by the method includes, but is not limited to, loss of libido, decreased sexual activity, diminished feelings of physical well-being, fatigue and hot flashes. In one embodiment, the method includes co-administering a composition comprising one or more crystalline forms of the compound of Formula (I) or a solvate thereof with one or more estrogens, such as estrone, 2-hydroxyestrone, 2-methoxyestrone, 4-hydroxyestrone, 15-α-hydroxyestrone, 16-α-hydroxyestrone, 16-β-hydroxyestrone, estradiol (17β-estradiol), 2-hydroxy-estradiol, 2-methoxyestradiol, 4-hydroxy-estradiol, 16-oxoestradiol, estriol, 16-epiestriol and 17-epiestriol or combinations thereof. In one embodiment, the method includes co-administering a composition comprising one or more crystalline forms of the compound of Formula (I) or a solvate thereof with one or more estrogenic compound, such as estradiol valerate, estrone, estrone sulfate, an estrone sulfate piperazine salt or an ester thereof, or a synthetic estrogen. In one embodiment, the method includes co-administering a composition comprising one or more crystalline forms of the compound of Formula (I) or a solvate thereof with one or more agents selected from among alendronate, calcitonin, clodronate, clomiphene, clomiphene citrate, clonidine, conjugated estrogen, natural estrogen, synthetic estrogen, ethinyl estradiol, estradiol, enclomiphene, enclomiphene citrate, etidronate, ibandronate, medroxyprogesterone acetate, megestrol acetate, norethindrone acetate, pamidronate, progesterone, risedronate, tiludronate, zuclomiphene, zuclomiphene citrate and combinations thereof.

Methods of Treating Hematopoietic Disorders

Also provided herein are methods of treating, preventing, suppressing, inhibiting or reducing the incidence of a hematopoietic disorder in a subject. The methods include administering to the subject a composition comprising one or more crystalline forms of the compound of Formula (I) or a solvate thereof, in an amount effective to treat the hematopoietic disorder. In some embodiments, the hematopoietic disorder includes, but is not limited to, anemia, leukemia, and hematopoietic conditions caused by bone marrow transplantation or chemo-/radiation therapy. Also provided are methods of increasing the number of red blood cells in a mammal in need thereof. The method includes administering a therapeutically effective amount of a composition comprising one or more crystalline forms of the compound of Formula (I) or a solvate thereof, in an amount effective to increase the number of red blood cells in a subject. Also provided are methods of treating anemia, thrombocytopenia or neutropenia in a subject. The methods include administering to the subject in need of such treatment a composition comprising one or more crystalline forms of the compound of Formula (I) or a solvate thereof, in an amount effective to treat anemia, thrombocytopenia or neutropenia in the mammal. In some embodiments of these methods, a composition comprising one or more crystalline forms of the compound of Formula (I) or a solvate thereof is co-administered with a therapeutically effective amount of at least one hematopoietic cytokine. In some embodiments, the hematopoietic cytokine is selected from among erythropoietin, granulocyte-colony stimulating factor, granulocyte-macrophage-colony stimulating factor, interleukin-1, interleukin-3, interleukin-4, interleukin-5, interleukin-7, interleukin-9, interleukin-11, macrophage-colony stimulating factor, stem cell factor and thrombopoietin.

Also provided are methods of increasing serum EPO levels in a subject. The methods include administering a therapeutically effective amount of a composition comprising one or more crystalline forms of the compound of Formula (I) or a solvate thereof, in an amount effective to increase the serum EPO levels in the subject.

Methods of Treating Neurodegenerative Diseases and Disorders

In some embodiments, provided herein are methods of treating, preventing, suppressing, inhibiting or reducing the incidence of a neurodegenerative disease or disorder in a subject. The methods include administering to a subject having a neurodegenerative disease or disorder, a composition comprising one or more crystalline forms of the compound of Formula (I) or a solvate thereof, in an amount effective to treat the neurodegenerative disease or disorder. In some embodiments, the neurodegenerative disorder is Alzheimer's disease. In some embodiments, methods for preventing the onset or delaying the progression of Alzheimer's disease in patients are provided. The method includes administering to a subject a composition comprising one or more crystalline forms of the compound of Formula (I) or a solvate thereof, in an amount effective to prevent the onset or delay the progression of Alzheimer's disease in a subject. The method can include co-administering an effective amount of a composition comprising one or more crystalline forms of the compound of Formula (I) or a solvate thereof with a therapeutically-effective amount of a compound that inhibits the formation or release of β-amyloid. Any of the known inhibitors of the formation or release of β-amyloid can be used in the methods, including, but not limited to, compounds described in U.S. Pat. App. Pub. Nos. U.S. 2002/0025955, 2002/0022621 and U.S. 2003/0114496 and in WO 03/018543, WO 01/53255, WO 01/66564, WO 01/70677, WO 01/90084, WO 01/77144, WO 02/30912, WO 02/36555, WO 02/081435, WO 02/081433, WO 98/28268, WO 02/47671, WO 99/67221, WO 01/34639, WO 01/34571, WO 00/07995, WO 00/38618, WO 01/92235, WO 01/77086, WO 01/74784, WO 01/74796, WO 01/74783, WO 01/60826, WO 01/19797, WO 01/27108, WO 01/27091, WO 00/50391 and WO 02/057252.

Methods of Treating Cognitive Impairment

Also provided herein are methods for treating, preventing, suppressing, inhibiting or reducing the incidence of cognitive impairment in a subject. The methods include administering to a subject having cognitive impairment a composition comprising one or more crystalline forms of the compound of Formula (I) or a solvate thereof, in an amount effective to treat the cognitive impairment.

Methods of Treating Depression

Also provided herein are methods for treating, preventing, suppressing, inhibiting or reducing the incidence of depression in a subject. The methods include administering to a subject having cognitive impairment a composition comprising one or more crystalline forms of the compound of Formula (I) or a solvate thereof, in an amount effective to treat depression.

Methods of Treating Obesity

Also provided herein are methods of treating, preventing, suppressing, inhibiting or reducing the incidence of obesity in a subject. The methods include administering to a subject a composition comprising one or more crystalline forms of the compound of Formula (I) or a solvate thereof, in an amount effective to treat obesity. In one embodiment, a composition comprising one or more crystalline forms of the compound of Formula (I) or a solvate thereof that is an AR agonist is used to treat a male subject with abdominal adiposity. In one embodiment, a composition comprising one or more crystalline forms of the compound of Formula (I) or a solvate thereof that is an AR antagonist is used to treat a female subject with abdominal obesity.

Methods of Treating Insulin Resistance and Diabetes

Provided herein are methods of treating, preventing, suppressing, inhibiting or reducing the incidence of insulin resistance in a subject. The methods include administering to a subject a composition comprising one or more crystalline forms of the compound of Formula (I) or a solvate thereof, in an amount effective to treat insulin resistance. Also provided herein are methods of treating, preventing, suppressing, inhibiting or reducing the incidence of type 2 diabetes in a subject. The methods include administering to a subject a composition comprising one or more crystalline forms of the compound of Formula (I) or a solvate thereof, in an amount effective to treat type 2 diabetes. In some embodiments, the method for treating diabetes includes co-administering an effective amount of a composition comprising one or more crystalline forms of the compound of Formula (I) or a solvate thereof with an effective amount of an anti-diabetic drug, such as, but not limited to, thiazolidinedione-type drugs such as pioglitazone or rosiglitazone, sulfonylurea-type drugs, such as chlorpropamide, glimepiride, glipizide, glyburide or tolbutamide, a biguanide-type drug such as metformin, exenatide, acarbose, repaglinide, nateglinide, tolazamide or combinations thereof.

Also provided herein are methods of treating, preventing, suppressing, inhibiting or reducing the incidence of arterial hypertension, hyper-insulineamia, hyperglycaemia or dyslipidaemia characteristically appearing with insulin resistance. The methods include administering to a subject a composition comprising one or more crystalline forms of the compound of Formula (I) or a solvate thereof, in an amount effective to treat arterial hypertension, hyperinsulinemia, hyperglycaemia, type 2 diabetes or dyslipidaemia characteristically appearing with insulin resistance.

Methods of Treating Sexual Dysfunction

In certain embodiments, provided herein are methods of treating, preventing, suppressing, inhibiting or reducing the incidence of sexual dysfunction in a subject. The methods include administering to the subject a composition comprising one or more crystalline forms of the compound of Formula (I) or a solvate thereof, in an amount effective to treat or prevent sexual dysfunction in the subject. In some embodiments, the sexual dysfunction is male erectile dysfunction. In some embodiments, the sexual dysfunction is impotence.

In certain embodiments, provided herein are methods of increasing the libido of a male or female subject. The methods include administering to the subject in need thereof a composition comprising one or more crystalline forms of the compound of Formula (I) or a solvate thereof in an amount that is effective to increase the libido of the subject.

Methods of Treating Arthritic Conditions and Inflammatory Disorders

Also provided herein are methods for treating, preventing, suppressing, inhibiting or reducing the incidence of an arthritic condition or inflammatory disorder. The methods include administering a composition comprising one or more crystalline forms of the compound of Formula (I) or a solvate thereof in an amount effective for the treatment or prevention of an arthritic condition or an inflammatory disorder. In one embodiment, the arthritic condition or inflammatory disorder is selected from among osteoarthritis, Behcet's disease, bursitis, tendonitis, CPPD deposition disease, carpal tunnel syndrome, Ehlers-Danlos syndrome, fibromyalgia, gout, infectious arthritis, inflammatory bowel disease, juvenile arthritis, lupus erythematosus, Lyme disease, Marfan syndrome, myositis, osteoarthritis, osteogenesis imperfecta, osteonecrosis, polyarteritis, polymyalgia rheumatica, psoriatic arthritis, Raynaud's phenomenon, reflex sympathetic dystrophy syndrome, Reiter's syndrome, rheumatoid arthritis, scleroderma and Sjogren's syndrome. In one embodiment, the method is for treating, preventing, suppressing, inhibiting or reducing the incidence of osteoarthritis, which includes administering a composition comprising one or more crystalline forms of the compound of Formula (I) or a solvate thereof in an amount effective for the treatment or prevention of osteoarthritis. In certain embodiments of these methods, the composition comprising one or more crystalline forms of the compound of Formula (I) or a solvate thereof is co-administered with one or more drugs or agents known to treat or prevent arthritic conditions, such as corticosteroids, cytotoxic drugs (or other disease modifying or remission inducing drugs), gold treatment, methotrexate, aspirin, NSAIDs, COX-2 inhibitors and DMARDs (Disease-Modifying Anti-Rheumatic Drugs).

Exemplary DMARDs include, but are not limited to, leflunomide, auranofin, sulfasalazine, mycophenolate, myochrysine, cyclosporine, cyclophosphamide, azathioprine, chlorambucil, methotrexate, minocycline, penicillamine and hydroxychloroquine. Exemplary NSAIDs include, but are not limited to, diclofenac/misoprostol, diclofenac potassium, diclofenac, diflunisal, etodolac, fenoprofen, flurbiprofen, ibuprofen, indomethacin, ketoprofen, meclofenamate, mefanamic acid, meloxicam, nabumetone, naproxen and naproxen sodium, oxaprozin, piroxicam, sodium sulindac and tolmetin. Exemplary COX-2 inhibitors include, but are not limited to, celecoxib, rofecoxib and valdecoxib.

Methods of Improving Lipid Profile

In certain embodiments, provided herein are methods of improving the lipid profile in a subject. The methods include administering to the subject a composition comprising one or more crystalline forms of the compound of Formula (I) or a solvate thereof in an amount effective to effect the lipid profile in the subject. In one embodiment, the composition comprising one or more crystalline forms of the compound of Formula (I) or a solvate thereof is co-administered with another agent, such as an anti-cholesterol agent or lipid-lowering agent, such as, but not limited to, β-hydroxy-β-methylbutyric acid, lactoferrin, cholestyramine, colestipol, colesevelam, nicotinic acid, fibric acids (gemfibrozil, fenofibrate and clofibrate) and GMG-coA reductase inhibitors (lovastatin, pravastatin, simvastatin, fluvastatin, atorvastatin and cerivastatin).

In certain embodiments, provided herein are methods of reducing circulating lipid levels in a subject. The method includes administering to the subject a composition comprising one or more crystalline forms of the compound of Formula (I) or a solvate thereof in an amount effective to reduce circulating lipid levels in the subject.

Methods of Treating Atherosclerosis

In certain embodiments, provided herein are methods of treating, preventing, suppressing, inhibiting or reducing the incidence of atherosclerosis and its associated diseases including cardiovascular disorders, cerebrovascular disorders, peripheral vascular disorders, and intestinal vascular disorders in a subject. The methods include administering to the subject a composition comprising one or more crystalline forms of the compound of Formula (I) or a solvate thereof, alone or in combination with a selective estrogen receptor modulator (SERM) compound.

Methods of Treating Conditions Related to Androgen Decline

In certain embodiments, provided herein are methods of treating, preventing, suppressing, inhibiting or reducing the incidence of a condition related to androgen decline, such as in a male subject. The methods include administering to the subject a composition comprising one or more crystalline forms of the compound of Formula (I) or a solvate thereof in an amount effective to treat the condition related to androgen decline in the subject. In some embodiments, the condition is selected from among fatigue, depression, decreased libido, sexual dysfunction, erectile dysfunction, hypogonadism, osteoporosis, hair loss, obesity, sarcopenia, osteopenia, benign prostate hyperplasia, anemia, alterations in mood and cognition, and prostate cancer.

Methods of Treating Conditions Related to Androgen Deficiency

In certain embodiments, provided herein are methods of treating, preventing, suppressing, inhibiting or reducing the incidence of a condition related to androgen deficiency, such as in a female subject. The methods include administering to the subject a composition comprising one or more crystalline forms of the compound of Formula (I) or a solvate thereof, in an amount effective to treat the condition related to androgen decline in the subject. In one embodiment, the condition is selected from among sexual dysfunction, decreased sexual libido, sarcopenia, osteopenia, osteoporosis, alterations in cognition and mood, depression, anemia, hair loss, obesity, endometriosis, breast cancer, uterine cancer and ovarian cancer.

Methods of Use of the Compound and Compositions Thereof

In certain embodiments, one or more compounds or compositions provided herein can be co-administered with one or more other therapeutic agents. In certain embodiments, such one or more other therapeutic agents are designed to treat the same disease or condition as the one or more compounds or pharmaceutical compositions provided herein. In certain embodiments, such one or more other therapeutic agents are designed to treat a different disease or condition as the one or more compounds or compositions provided herein. In certain embodiments, such one or more other therapeutic agents are designed to treat an undesired effect of one or more compounds or compositions provided herein. In certain embodiments, one or more compounds or compositions provided herein is co-administered with another therapeutic agent to treat an undesired effect of that other agent.

In certain embodiments, compounds or compositions provided herein and one or more other therapeutic agents are administered at the same time. In some embodiments, compounds or compositions provided herein and one or more other therapeutic agents are administered at the different times. In certain embodiments, compounds or compositions provided herein and one or more other therapeutic agents are prepared together in a single formulation. In certain embodiments, compounds or compositions provided herein and one or more other therapeutic agents are prepared separately.

Examples of therapeutic agents that can be co-administered with compounds or compositions provided herein include, but are not limited to, analgesics (e.g., acetaminophen); anti-inflammatory agents, including, non-steroidal anti-inflammatory drugs (e.g., ibuprofen, COX-1 inhibitors and COX-2, inhibitors); salicylates; anti-biotics; antivirals; antifungal agents; antidiabetic agents (e.g., biguanides, glucosidase inhibitors, insulins, sulfonylureas, and thiazolidinediones); adrenergic modifiers; diuretics; hormones (e.g., anabolic steroids, androgen, estrogen, calcitonin, progestin, somatostan, and thyroid hormones); immuno-modulators; muscle relaxants; anti-histamines; osteoporosis agents (e.g., bisphosphonates, calcitonin, and estrogens); prostaglandins, antineoplastic agents; psychotherapeutic agents; sedatives; antibodies; and vaccines.

In other embodiments, therapeutic agents that can be co-administered with compounds or compositions provided herein include, but are not limited to, other modulators of nuclear hormone receptors or other suitable therapeutic agents useful in the treatment of the aforementioned disorders including: anti-diabetic agents; anti-osteoporosis agents; anti-obesity agents; anti-inflammatory agents; anti-anxiety agents; anti-depressants; anti-hypertensive agents; anti-platelet agents; anti-thrombotic and thrombolytic agents; cardiac glycosides; cholesterol/lipid lowering agents; mineralo-corticoid receptor antagonists; phosphodiesterase inhibitors; protein tyrosine kinase inhibitors; thyroid mimetics (including thyroid receptor agonists); anabolic agents; HIV or AIDS therapies; therapies used in the treatment of Alzheimer's and other cognitive disorders; therapies used in the treatment of sleeping disorders; antiproliferative agents; anti-tumor agents; bisphosphonates; estrogens; SERMs; anti-estrogens; cathepsin inhibitors; $\alpha_v\beta_3$ integrin receptor antagonists; calcitonin; PPARγ inhibitors; osteoprotegerin; and proton pump inhibitors.

EXAMPLES AND EXPERIMENTAL METHODS

Additional embodiments are disclosed in further detail in the following examples, which are not in any way intended to limit the scope of the claims.

X-ray Powder Diffraction (XRPD)

Some XRPD patterns were collected using a PANalytical X'Pert Pro diffractometer. The specimen was analyzed using Cu radiation produced using an Optix long fine-focus source. An elliptically graded multilayer mirror was used to focus the Cu Kα X-rays of the source through the specimen and onto the detector. The specimen was sandwiched between 3-micron thick films, analyzed in transmission geometry, and rotated to optimize orientation statistics. A beam-stop and helium purge were used to minimize the background generated by air scattering. Soller slits were used for the incident and diffracted beams to minimize axial divergence. Diffraction patterns were collected using a scanning position-sensitive detector (X'Celerator) located 240 mm from the specimen. Prior to the analysis a silicon specimen (NIST standard reference material 640c) was analyzed to verify the position of the silicon 111 peak.

Alternatively, X-ray powder diffraction (XRPD) analyses were performed using an Inel XRG-3000 diffractometer equipped with a CPS (Curved Position Sensitive) detector with a 2θ range of 120°. Real time data were collected using Cu-Kα radiation at a resolution of 0.03° 2θ. The tube voltage and amperage were set to 40 kV and 30 mA, respectively. The monochromator slit was set at 5 mm (or 2 mm) by 160 μm. The pattern is displayed from 2.5-40° 2θ. Samples were prepared for analysis by packing them into thin-walled glass capillaries. Each capillary was mounted onto a goniometer head that is motorized to permit spinning of the capillary during data acquisition. The samples were analyzed for 5 min. Instrument calibration was performed using a silicon reference standard.

Thermogravimetric Analysis (TG)

Thermogravimetric analyses were performed using a TA Instruments 2950 thermogravimetric analyzer. Each sample was placed in an aluminum sample pan and inserted into the TG furnace. The furnace was heated under nitrogen at a rate of 10° C./min, up to a final temperature of 350° C. Nickel and Alumel™ were used as the calibration standards.

Thermogravimetric Fourier-Transform Infrared Spectroscopy Analysis (TG-FTIR)

Thermogravimetric Fourier-Transform Infrared Spectroscopy measurements were carried out with a Netzsch Thermo-Microbalance TG 209 coupled to a Bruker FTIR Spectrometer Vector 22 (sample pans with a pinhole, N2 atmosphere, heating rate 10 K/min, range 25 to 250° C.).

Differential Scanning calorimetry Analysis (DSC)

In Differential scanning calorimetry (DSC) was performed using a TA Instruments differential scanning calorimeter 2920 or Q2000. The sample was placed into an aluminum DSC pan, and the weight accurately recorded. The pan was covered with a lid and then crimped. The sample cell was heated under a nitrogen purge at a rate of 10° C./min, up to a final temperature of 250° C. Indium metal was used as the calibration standard. Reported temperatures are at the transition maxima.

$^1$H Nuclear Magnetic Resonance (NMR)

The solution $^1$H-NMR spectrum was acquired at ambient temperature with a Varian $^{UNITY}$INOVA-400 spectrometer at a $^1$H Larmor frequency of 399.796 MHz. The sample was dissolved in DMSO-d$_6$. The spectrum was referenced to internal tetramethylsilane (TMS) at 0.0 ppm.

Dynamic Vapor Sorption (DVS)

Moisture sorption/desorption data were collected on a VTI SGA-100 Vapor Sorption Analyzer. Sorption and desorption data were collected over a range of 5% to 95% relative humidity (RH) at 10% RH intervals under an nitrogen purge. Samples were not dried prior to analysis. Equilibrium criteria used for analysis were less than 0.0100% weight change in 5 minutes, with a maximum equilibration time of 3 hours if the weight criterion was not met. Data were not corrected for the initial moisture content of the samples. NaCl and PVP were used as calibration standards.

Indexing Studies

The XRPD patterns of various crystalline forms were indexed using DASH version 3.1. The solutions were further refined via Pawley refinement using DASH version 3.1. The indexed solutions were verified and illustrated using Check-Cell version 11/01/04.

Measurement of the Approximate Solubility

Aliquots of various solvents were added to measured amounts of compound with agitation (typically sonication) at ambient or elevated temperatures until complete dissolution was achieved, as judged by visual observation.

The approximate solubility at ambient temperature must be known in order to carry out systematic crystallization experiments. The compound showed high solubilities in most of the organic solvents tested. The material showed low solubilities in cyclohexane, hexanes, water, and aqueous solvent mixtures with higher water content. The approximate solubility of the starting material at ambient are given in Table 1 below.

TABLE 1

Approximate Ambient Solubility of Starting Compound of Formula (I)

| Solvent | Solubility (mg/ml) |
| --- | --- |
| acetone | >112 |
| acetonitrile | >110 |
| 1-butanol | 37 |
| 2-butanone | >107 |
| tert-butyl methyl ether | >111 |
| chloroform | 37 |
| cyclohexane | <2 |
| dichloromethane | 37 |
| diethyl ether | 58 |
| 1,4-dioxane | >111 |
| ethanol | >104 |
| ethyl acetate | >108 |
| hexafluoroisopropanol | >106 |
| hexanes | <2 |
| isopropanol | >102 |
| isopropyl ether | 55 |
| methanol | >116 |
| methyl isobutyl ketone | >100 |
| 1-propanol | 55 |
| tetrahydrofuran | >102 |
| toluene | 15 |
| 2,2,2-trifluoroethanol | 51 |
| water | <2 |
| acetone/water 50:50 v/v | 9 |
| acetone/water 20:80 v/v | <2 |
| acetonitrile/water 20:80 v/v | <2 |
| 1,4-dioxane/water 20:80 v/v | <2 |
| ethanol/water 20:80 v/v | <2 |
| hexafluoroisopropanol/water 20:80 v/v | <2 |
| isopropanol/water 20:80 v/v | <2 |
| methanol/water 20:80 v/v | <2 |
| 1-propanol/water 20:80 v/v | <2 |
| tetrahydrofuran/water 20:80 v/v | <2 |
| 2,2,2-trifluoroethanol/water 20:80 v/v | <2 |

Example 1: Polymorph Screen Experiments

Polymorph screen experiments were carried out utilizing precipitation, slow cool, slow evaporation, and slurry experiments. All experiments were conducted on approximately a 10 mg scale unless designated as scale-ups. All experiments were conducted under light-sensitive conditions. The starting material (i.e., the compound of Formula (I)) was designated as Form E+C after analysis via X-ray powder diffraction. Thermal data indicated that the starting material was not solvated.

Crash Precipitation (CP)

Solutions of compound were prepared in various solvents and filtered through a 0.2-μm nylon filter. Aliquots of various antisolvents were dispensed with stirring until precipitation occurred. If necessary, samples were placed in the freezer (approximately −25 to −10° C.) to facilitate precipitation. Solids were collected by vacuum filtration and analyzed.

Fast Evaporation (FE)

Solutions of compound were prepared in various solvents in which samples were sonicated between aliquot additions. Once a mixture reached complete dissolution, as judged by visual observation, the solution was filtered through a 0.2-μm nylon filter. The solution was allowed to evaporate in a dark fume hood from an open vial. Solutions were allowed to evaporate to dryness. The solids were isolated and analyzed.

Slow Cool (SC)

Saturated solutions of compound were prepared in various solvents at an elevated temperature and filtered warm through a 0.2-μm nylon filter into a warm vial. The vial was capped and left on the hot plate, and the hot plate was turned off to allow the sample to slow cool to ambient temperature. If no or very few solids were present after cooling to ambient temperature, the sample was placed in the refrigerator (approximately 2 to 8° C.) and/or the freezer (approximately −25 to −10° C.) for further cooling. Solids were collected by vacuum filtration or by withdrawing solvent via pipette and allowing the solids to air dry at ambient conditions or under nitrogen prior to analysis.

Slow Evaporation (SE)

Solutions of compound were prepared in various solvents in which samples were sonicated between aliquot additions. Once a mixture reached complete dissolution, as judged by visual observation, the solution was filtered through a 0.2-μm nylon filter. The solution was allowed to evaporate in a dark fume hood from a vial covered with aluminum foil perforated with one pinhole unless otherwise specified. Solutions were allowed to evaporate to dryness unless designated as partial slow evaporations. The solids were isolated and analyzed.

Slurry Experiments

Solutions of compound were prepared by adding enough solids to a given solvent at ambient conditions so that undissolved solids were present. The mixture was then loaded onto an orbit shaker in a sealed vial at ambient temperature for an extended period of time, typically approximately 1 week. The solids were isolated by vacuum filtration or by withdrawing solvent via pipette and allowing the solids to air dry at ambient conditions prior to analysis.

Over 50 polymorph screen experiments were conducted on the compound of Formula (I). Form E, as well as mixtures of forms E, C, and B, was produced from most of these experiments, with Form E resulting with the highest frequency. A mixture of forms E and C was recovered from slurries in cyclohexane and the following solvents containing 80% water:acetone, acetonitrile, 1,4-dioxane, ethanol, methanol, 1-propanol, 2-propanol, and 2,2,2-trifluoroethanol. A mixture of forms E and C likely resulted from slurry in hexanes and precipitated from ethyl acetate:hexanes (50: 50 v/v) at approximately 51° C. A slow evaporation experiment in methanol resulted in a mixture of Forms E+C with minor Form B by XRPD. A new crystalline XRPD pattern, designated as Form E, was observed from the majority of slow evaporation experiments, as well as from slurries in water and HFIPA:water (20:80 v/v), crash precipitation in toluene with hexanes, and slow cooling experiments utilizing 50:50 v/v mixtures of isopropanol:cyclohexane, acetone: water, and ethanol:water. Possible single crystals were grown by slow evaporation in HFIPA:water (20:80 v/v). A small portion of the sample was submitted for XRPD and exhibited x-ray amorphous material with form B peaks. Slow evaporations in methylene chloride, hexafluoroisopropanol, isopropyl ether, and methyl isobutyl ketone all gave mixtures of form B with minor E+C present, based on XRPD. The details of various polymorph screen experiments and results are provided in Table 2 below.

TABLE 2

Polymorph Screens for the Compound of Formula (I)

| Solvent/System | Conditions | XRPD Result |
| --- | --- | --- |
| acetone | SE | Form E |
|  | SE, scale up | Form E |
|  | SE, scale up | Form E |
|  | SE, scale up | Form E |
| acetonitrile | SE | Form E |
| 1-butanol | SE | Form E |
| 2-butanone | SE | Form E |
| 2-butanone/hexanes 50:50 v/v | SC. Freezer 20 days | — |
| tert-butyl methyl ether | SE | Form E |
| chloroform | SE | Form E |
| cyclohexane | slurry, RT, 7 days | Form E + C |
| dichloromethane | SE | likely Form B + minor Form E + C |
| diethyl ether | SE | Form E |
| 1,4-dioxane | SE | Form E |
| ethanol | SE | Form E |
| ethyl acetate | SE | Form E |
| ethyl acetate/hexanes 50:50 v/v | precipitation at 51° C. | Form E + C (small sample) |
| hexafluoroisopropanol | SE | Form B + minor Form E + C |
| hexanes | slurry, RT, 7 days | Form E + C (small sample) |
|  | filtrate from slurry | insufficient solid |
| isopropanol | SE | Form E |
| isopropanol/ cyclohexane 50:50 v/v | SC, refrigerator for 7 hours, freezer for 7 days | Form E |
| isopropyl ether | SE (Sample 1) | likely Form B + minor Form E + C (small sample) |
|  | SE, stored under light-sensitive conditions for 15 days (Sample 1) | likely Form B + minor Form E + C (small sample) |
|  | SE, scale-up | Form E + possible Form B |
|  | SE, scale-up, seeded with crystals from Sample 1 | Form B + minor Form E + C (small sample) |
| methanol | SE | Form E + C + minor Form B |
| methyl isobutyl ketone | SE | Form B + minor Form E + C |
| 1-propanol | SE | Form E |
| tetrahydrofuran | SE | Form E |
| tetrahydrofuran/ cyclohexane 50:50 v/v | SC, freezer for 17 days SE | — Form E |
| toluene | SE | Form E |
|  | SC, freezer for 20 days | — |
|  | CP with hexanes | Form E |
| 2,2,2-trifluoroethanol | SE | Form E |
| water | slurry, RT, 7 days | Form E (small sample) |
| acetone/water 50:50 v/v | SE | Form E |
|  | SC, freezer, 7 days | — |
|  | SC refrigerator, 7 days | Form E |
| acetone/water 20:80 v/v | slurry, RT, 7 days | Form E + C |
| acetonitrile/water 20:80 v/v | slurry, RT, 7 days | Form E + C |
| 1,4-dioxane/water 20:80 v/v | slurry, RT, 7 days | Form E + C |

TABLE 2-continued

Polymorph Screens for the Compound of Formula (I)

| Solvent/System | Conditions | XRPD Result |
|---|---|---|
| ethanol/water 20:80 v/v | slurry, RT, 7 days | Form E + C |
| ethanol/water 50:50 v/v | SC | Form E |
| hexafluoroisopropanol/water 20:80 v/v | slurry, RT, 7 days | Form E |
| | Filtrate from slurry above, SE (partial) | Amorphous + possible Form B |
| isopropanol/water 20:80 v/v | slurry, RT, 7 days | Form E + C |
| methanol/water 20:80 v/v | slurry, RT, 7 days | Form E + C |
| 1-propanol/water 20:80 v/v | slurry, RT, 7 days | Form E + C |
| tetrahydrofuran/water 20:80 v/v | slurry, RT, 5 days | — |
| | SE, 29 days | — |
| | FE | possibly amorphous + possible Form E + C |
| 2,2,2-trifluoroethanol/water 20:80 v/v | slurry, RT, 7 days | Form E + C |

Example 2: Interconversion Slurries

Crystal forms of the compound of Formula (I) were weighed out in approximately equal amounts and combined as desired. Aliquots of saturated solutions of compound in various solvents were filtered (0.2-µm nylon filter) into vials containing solid mixtures such that undissolved solids were present. The mixture was then agitated by either loading it onto an orbit shaker or adding a cross-shaped stir bar and allowing the mixture to stir in a sealed vial at stated conditions. The solids were isolated by vacuum filtration and analyzed.

Interconversion slurries were conducted as individual pairings between the E+C mixture and Form E material and between forms C and E. The experiments were carried out in cyclohexane and acetone:water 20:80, at room temperature for 7 days. Additional slurries were set up in toluene at room temperature for 1 day and at approximately 5° C. for 2 days. The results of these slurries are presented below in Table 3.

A second set of interconversion slurries was conducted in which all unique patterns were slurried together at 50° C. in cyclohexane and ethanol:water 50:50. A mixture of Form C with a likely minor component of the E+C mixture was obtained from ethanol:water 50:50, and Form C resulted from the slurry in cyclohexane, indicating Form C is the most stable form at both conditions. The results of these slurries are presented below in Table 4.

The interconversion studies show that crystal Form C is the most thermodynamically stable form in cyclohexane, acetone:water (20:80 v/v) and toluene at ambient temperature and in ethanol:water (50:50 v/v) at approximately 50° C. Thus, Form C is the thermodynamically most stable form at ambient temperatures to 50° C. Form E is the most stable form in toluene at approximately 5° C.

TABLE 3

Interconversion Studies for Crystal Forms of Compound of Formula (I)

| Crystal Form Source 1 | Crystal Form Source 2 | Solvent System | Conditions | XRPD Result |
|---|---|---|---|---|
| E + C | E | cyclohexane | slurry, RT, 7 days | Form E |
| | E | acetone/water 20:80 v/v | slurry, RT, 7 days | Form E |
| | E | toluene | slurry, RT, 1 day | Form C |
| | B + minor E + C | cyclohexane | slurry, RT, 7 days | Form E + C with minor B |
| | | acetone/water 20:80 v/v | slurry, RT, 7 days | Form E + C with minor B |
| | — | toluene | slurry, −5° C., 2 days | Form E |
| C | E | cyclohexane | slurry, RT, 7 days | Form C + likely minor E + C |
| | E | acetone/water 20:80 v/v | slurry, RT, 7 days | mostly Form C with minor peaks from Form E |
| | E | acetone/water 50:50 v/v | slurry, RT, 1 day | — |
| | | toluene | slurry, RT, 1 day | Form C |

TABLE 4

Interconversion Studies for Crystal Forms of Compound of Formula (I)

| Crystal Form Starting Material | Solvent System | Conditions | Description | XRPD Result |
|---|---|---|---|---|
| E + C<br>E<br>B + minor E + C<br>C | cyclohexane | slurry, 50° C., 7 days | off-white, small needles, birefringent | Form C |
| E + C<br>E<br>B + minor E + C<br>C | ethanol/water 50:50 v/v | slurry, 50° C., 7 days | Light yellow, aggregates of thick needles, birefringent | Form C + likely minor E + C |

Example 3: Heating Experiment

The starting crystal Form was heated to 120° C. and the resulting material was analyzed by XRPD. The results are summarized in Table 5 below and indicate that crystal Form C is the thermodynamically more stable crystal form.

TABLE 5

Heating Study for Crystal Form E + C of Compound of Formula (I)

| Conditions | Description | XRPD Result |
|---|---|---|
| heated to 120° C. | Light yellow, small needles and aggregates, birefringent | Form C |
| | Light yellow, small needles and morphology unknown, birefringent | Form C |

Example 4: Characterization of Crystalline Samples

The crystalline solid forms were characterized by XRPD, thermogravimetry (TG), DSC and selected samples by solution NMR.

The XRPD results of crystalline Form C (FIG. 1) show good crystallinity. A melting temperature at approximately 163° C. was observed using differential scanning calorimetry (FIG. 5). Crystalline Form C was non-hygroscopic by automated vapor sorption/desorption analysis (FIG. 9). Solution NMR shows the spectrum of crystalline Form C (FIG. 10) was similar to that of the starting material (not shown).

Figure 3:
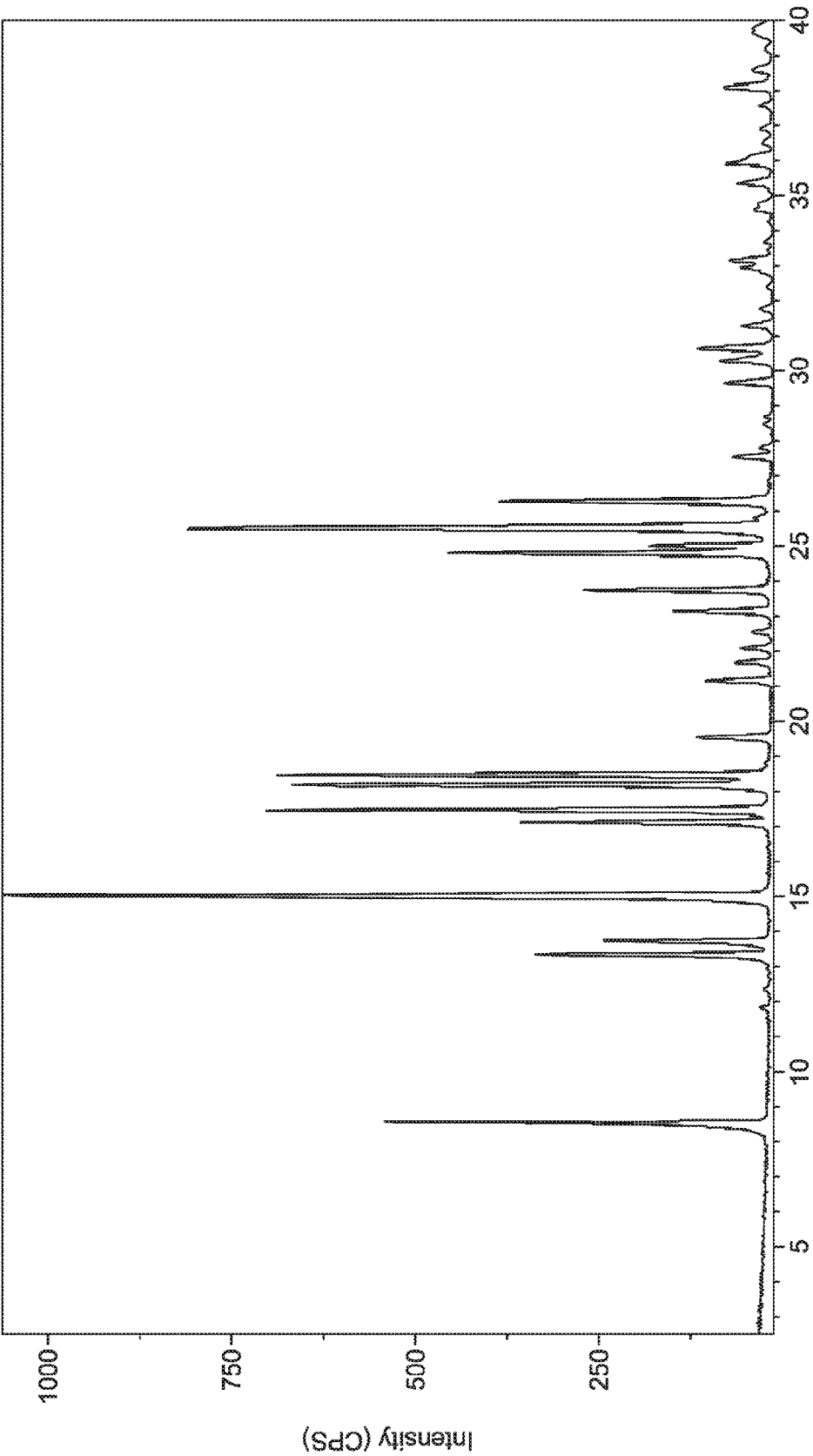
FIG. 3 is an X-ray powder diffraction pattern of crystalline Forms C+E of Formula (I).
Figure 7:
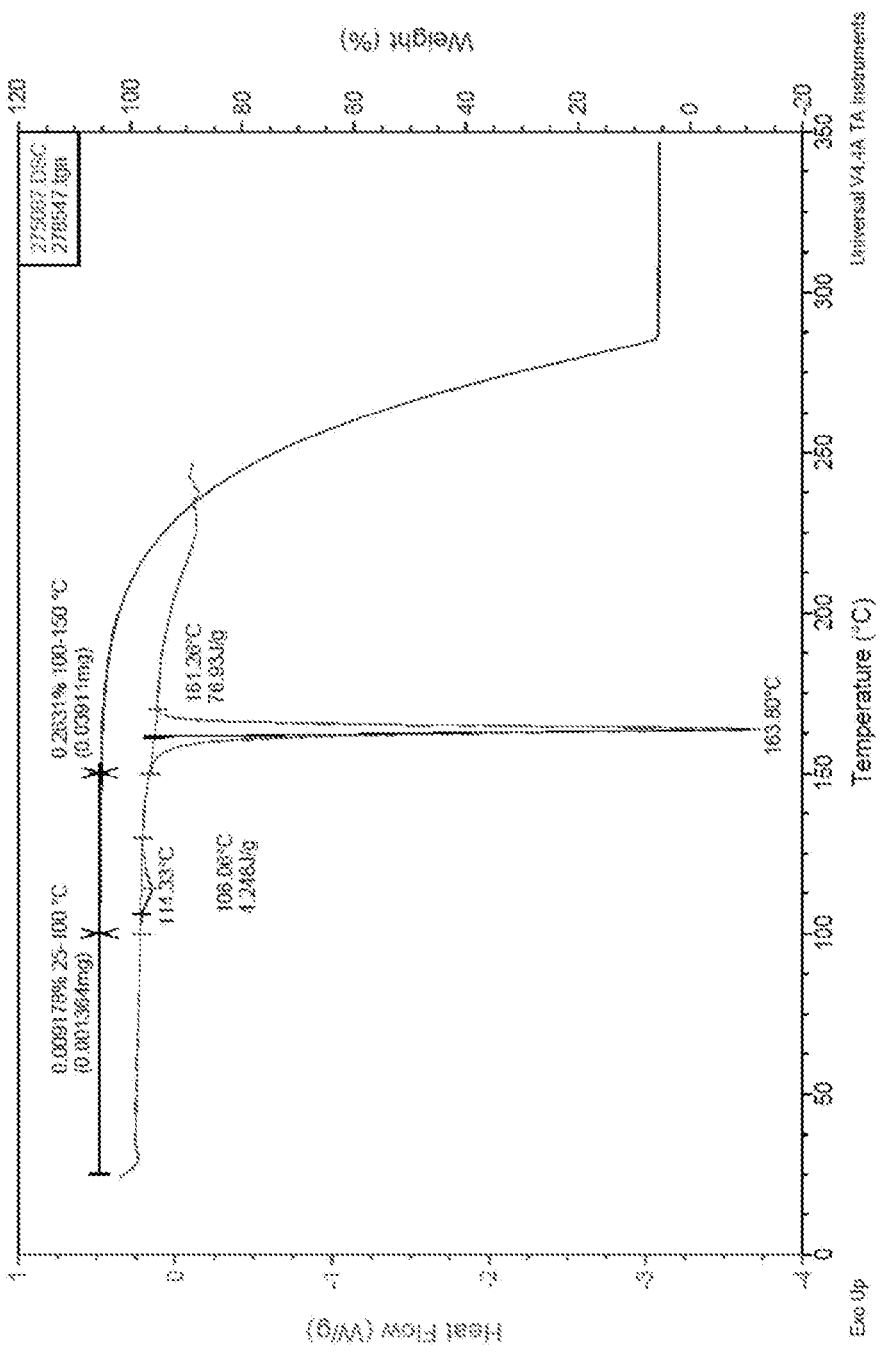
FIG. 7 shows a differential scanning calorimetry and thermogravimetric analysis overlay for crystalline Forms E+C of compound of Formula (I).
Figure 8:
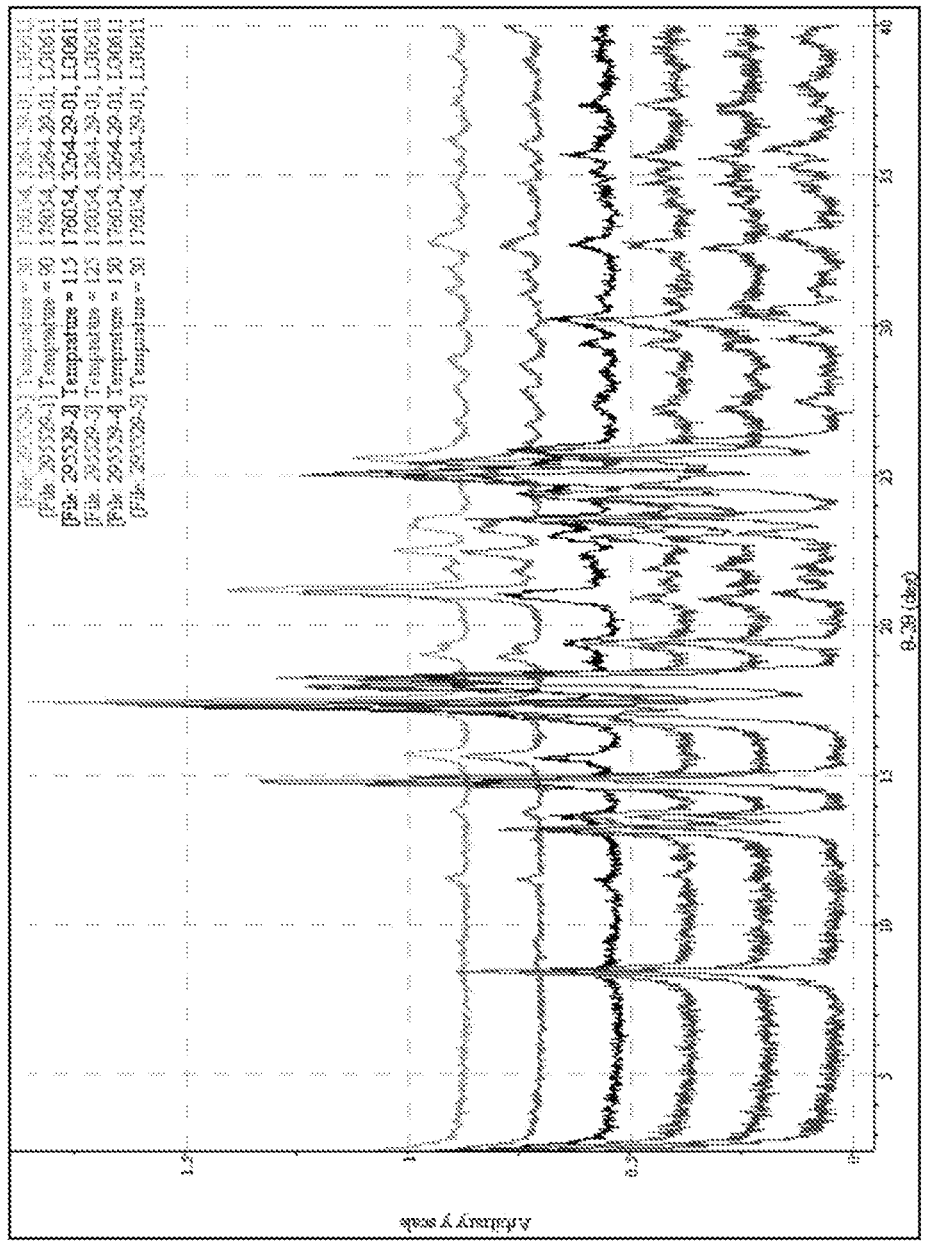
FIG. 8 is a VT-XRPD analysis of crystalline Form E of Formula (I).

The XRPD results of crystalline Form E (FIG. 2) show good crystallinity. Differential scanning calorimetry and thermogravimetric analysis results show a minor endotherm at approximately 120° C. followed by an intense endotherm at approximately 162° C. (FIG. 6). Crystalline Form E was unsolvated and determined to be slightly hygroscopic. The XRPD results of crystalline Forms E+C (FIG. 3) show good crystallinity. Differential scanning calorimetry results for crystalline Forms E+C were very similar to that of Form E (FIG. 7). The E+C mixture was slightly hygroscopic and unsolvated. Both Form E and the mixture of forms E+C appear to undergo the same endothermic transition at approximately 114-120° C., possibly indicating conversion to a more stable form, prior to melting at approximately 162-164° C. Analysis by VT-XRPD confirmed conversion to Form C upon heating to 115° C., observed as a mixture of forms E+C at this temperature (FIG. 8). Form conversion was complete by 125° C. in the solid state. Form C remained stable upon heating to 150° C. and cooling down to ambient temperature.

The XRPD results of crystalline Forms B (FIG. 4) show good crystallinity. Form B material always included small amounts of crystalline Forms E+C. Form B+minor E+C was unsolvated with a probable melt at approximately 159° C. The material likely underwent a form transformation upon heating at approximately 150° C.

Interconversion slurries among all forms of the compound of Formula (I) ultimately indicated that Form C is the most thermodynamically stable form in cyclohexane, acetone:water 20:80, and toluene at ambient temperature and in cyclohexane and ethanol:water 50:50 at approximately 50° C. Thus, Form C is the thermodynamically most stable form at ambient to 50° C. Form E is the most stable form in toluene at approximately 5° C. The DSC data and interconversion results suggest that forms C and E are enantiotropic with a transition temperature less than ambient.

Crystalline Form E and crystalline Form C were indexed based on their respective XRPD patterns, with the results summarized below in Table 1. Successful indexing of these patterns indicates that the respective samples are composed primarily of a single crystalline phase. To confirm the tentative indexing solution, the molecular packing motifs within the crystallographic unit cells must be determined. However, no attempts at molecular packing were performed.

TABLE 6

| Indexing Solution and Derived Quantities | | |
|---|---|---|
| | Form/Pattern | |
| Family and Space Group | Form C Orthorhombic $P2_12_12_1$ (#19) | Form E Orthorhombic $P2_12_12_1$ (#19) |
| Z'/Z | 1/4 | 1/4 |
| a (Å) | 7.181 | 8.366 |
| b (Å) | 14.320 | 11.659 |
| c (Å) | 14.993 | 15.160 |
| α (deg) | 90 | 90 |
| β (deg) | 90 | 90 |

TABLE 6-continued

| Indexing Solution and Derived Quantities | | |
|---|---|---|
| | Form/Pattern | |
| Family and Space Group | Form C Orthorhombic $P2_12_12_1$ (#19) | Form E Orthorhombic $P2_12_12_1$ (#19) |
| γ (deg) | 90 | 90 |
| Volume (Å³/cell) | 1541.6 | 1478.8 |
| V/Z | 385.4 | 369.7 |

Example 5: X-Ray Powder Diffraction (XRPD) Measurements of Crystalline Form C

XRPD measurements of crystalline Form C of compound of Formula (I) were measured. Observed peaks are shown in Table 7. Prominent peaks are listed in Table 8. Note that none of the peaks are known to be representative or characteristic of this material since the state of preferred orientation in this sample is not known.

The range of data collected may be instrument dependent. Under most circumstances, peaks within the range of up to about 30° 2θ were selected. Rounding algorithms were used to round each peak to the nearest 0.01° 2θ, based on the instrument used to collect the data and/or the inherent peak resolution. The location of the peaks along the x-axis (° 2θ) in both the figures and the tables were determined using proprietary software and rounded to one or two significant figures after the decimal point based upon the above criteria. Peak position variabilities are given to within +0.2° 2θ. For d-space listings, the wavelength used to calculate d-spacings was 1.541874 Å, the weighted average of the Cu-Kα₁ and Cu-Kα₂ wavelength.

TABLE 7

| Observed Peaks for Crystalline Form C | | |
|---|---|---|
| Diffraction angle °2θ (deg) | d space (Å) | Intensity (%) |
| 8.53 ± 0.20 | 10.368 | 89 |
| 11.79 ± 0.20 | 7.508 | 4 |
| 12.36 ± 0.20 | 7.164 | 3 |
| 13.32 ± 0.20 | 6.645 | 52 |
| 13.69 ± 0.20 | 6.647 | 34 |
| 15.00 ± 0.20 | 5.908 | 100 |
| 17.08 ± 0.20 | 5.19 | 36 |
| 17.47 ± 0.20 | 5.077 | 83 |
| 18.17 ± 0.20 | 4.882 | 66 |
| 18.45 ± 0.20 | 4.808 | 81 |
| 19.51 ± 0.20 | 4.551 | 17 |
| 21.13 ± 0.20 | 4.205 | 11 |
| 21.65 ± 0.20 | 4.105 | 6 |
| 22.06 ± 0.20 | 4.209 | 7 |
| 22.55 ± 0.20 | 3.943 | 5 |
| 23.13 ± 0.20 | 3.45 | 17 |
| 23.72 ± 0.20 | 3.751 | 30 |
| 24.76 ± 0.20 | 3.597 | 24 |
| 24.99 ± 0.20 | 3.563 | 18 |
| 25.52 ± 0.20 | 3.49 | 55 |
| 26.24 ± 0.20 | 3.396 | 25 |
| 27.53 ± 0.20 | 3.24 | 7 |
| 29.62 ± 0.20 | 3.016 | 8 |

Table 10 provides XRPD data identified as "Prominent Peaks". Prominent peaks are a subset of the entire observed peak list. Prominent peaks are selected from observed peaks by identifying preferably non-overlapping, low-angle peaks, with strong intensity.

TABLE 8

Prominent Peaks for Crystalline Form C

| Diffraction angle °2θ (deg) | d space (Å) | Intensity (%) |
|---|---|---|
| 8.53 ± 0.20 | 10.368 | 89 |
| 13.32 ± 0.20 | 6.645 | 52 |
| 13.69 ± 0.20 | 6.647 | 34 |
| 15.00 ± 0.20 | 5.908 | 100 |
| 17.08 ± 0.20 | 5.19 | 36 |
| 17.47 ± 0.20 | 5.077 | 83 |
| 18.17 ± 0.20 | 4.882 | 66 |
| 18.45 ± 0.20 | 4.808 | 81 |
| 19.51 ± 0.20 | 4.551 | 17 |
| 21.13 ± 0.20 | 4.205 | 11 |
| 23.13 ± 0.20 | 3.45 | 17 |
| 23.72 ± 0.20 | 3.751 | 30 |
| 25.52 ± 0.20 | 3.49 | 55 |
| 26.24 ± 0.20 | 3.396 | 25 |

Example 6: X-Ray Powder Diffraction (XRPD) Measurements of Crystalline Form E

XRPD measurements of crystalline Form E of compound of Formula (I) were measured. Observed peaks are shown in Table 9. Prominent peaks are listed in Table 10.

The range of data collected may be instrument dependent. Under most circumstances, peaks within the range of up to about 30° 2θ were selected. Rounding algorithms were used to round each peak to the nearest 0.01° 2θ, based on the instrument used to collect the data and/or the inherent peak resolution. The location of the peaks along the x-axis (° 2θ) in both the figures and the tables were determined using proprietary software and rounded to one or two significant figures after the decimal point based upon the above criteria. Peak position variabilities are given to within ±0.2° 2θ. For d-space listings, the wavelength used to calculate d-spacings was 1.541874 Å, the weighted average of the Cu-Kα$_1$ and Cu-Kα$_2$ wavelength.

TABLE 9

Observed Peaks for Crystalline Form E

| Diffraction angle °2θ (deg) | d space (Å) | Intensity (%) |
|---|---|---|
| 9.55 ± 0.20 | 9.263 | 4 |
| 11.65 ± 0.20 | 7.594 | 12 |
| 12.99 ± 0.20 | 6.815 | 3 |
| 13.91 ± 0.20 | 6.367 | 9 |
| 14.24 ± 0.20 | 6.218 | 3 |
| 15.18 ± 0.20 | 5.837 | 2 |
| 15.76 ± 0.20 | 5.622 | 21 |
| 17.52 ± 0.20 | 5.062 | 100 |
| 19.12 ± 0.20 | 4.641 | 9 |
| 19.44 ± 0.20 | 4.566 | 6 |
| 21.23 ± 0.20 | 4.185 | 48 |
| 21.93 ± 0.20 | 4.053 | 3 |
| 22.57 ± 0.20 | 3.94 | 10 |
| 23.32 ± 0.20 | 3.815 | 11 |
| 23.62 ± 0.20 | 3.767 | 10 |
| 24.67 ± 0.20 | 3.609 | 2 |
| 25.26 ± 0.20 | 3.526 | 6 |
| 25.64 ± 0.20 | 3.474 | 16 |
| 25.92 ± 0.20 | 3.437 | 4 |
| 26.89 ± 0.20 | 3.315 | 2 |
| 28.05 ± 0.20 | 3.181 | 2 |
| 28.97 ± 0.20 | 3.083 | 2 |

Table 10 provides XRPD data identified as "Prominent Peaks". Prominent peaks are a subset of the entire observed peak list. Prominent peaks are selected from observed peaks by identifying preferably non-overlapping, low-angle peaks, with strong intensity.

TABLE 10

Prominent Peaks for Crystalline Form E

| Diffraction angle °2θ (deg) | d space (Å) | Intensity (%) |
|---|---|---|
| 9.55 ± 0.20 | 9.263 | 4 |
| 11.65 ± 0.20 | 7.594 | 12 |
| 12.99 ± 0.20 | 6.815 | 3 |
| 13.91 ± 0.20 | 6.367 | 9 |
| 15.76 ± 0.20 | 5.622 | 21 |
| 17.52 ± 0.20 | 5.062 | 100 |
| 19.12 ± 0.20 | 4.641 | 9 |
| 19.44 ± 0.20 | 4.566 | 6 |
| 21.23 ± 0.20 | 4.185 | 48 |
| 21.93 ± 0.20 | 4.053 | 3 |
| 22.57 ± 0.20 | 3.94 | 10 |
| 23.32 ± 0.20 | 3.815 | 11 |
| 23.62 ± 0.20 | 3.767 | 10 |
| 25.26 ± 0.20 | 3.526 | 6 |
| 25.64 ± 0.20 | 3.474 | 16 |

Example 7: X-Ray Powder Diffraction (XRPD) Measurements of Crystalline Form B

XRPD measurements of crystalline Form B of compound of Formula (I) were measured. Observed peaks are shown in Table 11. Prominent peaks are listed in Table 12. Note that none of the peaks are known to be representative or characteristic of this material since the state of preferred orientation in this sample is not known.

The range of data collected may be instrument dependent. Under most circumstances, peaks within the range of up to about 30° 2θ were selected. Rounding algorithms were used to round each peak to the nearest 0.01° 2θ, based on the instrument used to collect the data and/or the inherent peak resolution. The location of the peaks along the x-axis (° 2θ) in both the figures and the tables were determined using proprietary software and rounded to one or two significant figures after the decimal point based upon the above criteria. Peak position variabilities are given to within ±0.2° 2θ. For d-space listings, the wavelength used to calculate d-spacings was 1.541874 Å, the weighted average of the Cu-Kαi and Cu-Kα$_2$ wavelength.

TABLE 11

Observed Peaks for Crystalline Form B

| Diffraction angle °2θ (deg) | d space (Å) | Intensity (%) |
|---|---|---|
| 9.01 ± 0.20 | 9.819 | 18 |
| 10.32 ± 0.20 | 8.571 | 14 |
| 11.70 ± 0.20 | 7.561 | 13 |
| 12.67 ± 0.20 | 6.985 | 15 |
| 13.26 ± 0.20 | 6.676 | 21 |
| 13.95 ± 0.20 | 6.347 | 12 |
| 14.75 ± 0.20 | 6.006 | 13 |
| 15.96 ± 0.20 | 5.55 | 76 |
| 17.10 ± 0.20 | 5.185 | 20 |
| 17.55 ± 0.20 | 5.053 | 100 |
| 19.15 ± 0.20 | 4.636 | 17 |
| 19.84 ± 0.20 | 4.476 | 15 |
| 21.26 ± 0.20 | 4.18 | 38 |
| 21.88 ± 0.20 | 4.062 | 17 |
| 22.61 ± 0.20 | 3.933 | 16 |
| 23.40 ± 0.20 | 3.801 | 14 |

TABLE 11-continued

Observed Peaks for Crystalline Form B

| Diffraction angle °2θ (deg) | d space (Å) | Intensity (%) |
|---|---|---|
| 23.65 ± 0.20 | 3.763 | 13 |
| 24.55 ± 0.20 | 3.627 | 44 |
| 25.38 ± 0.20 | 3.51 | 17 |
| 25.66 ± 0.20 | 3.472 | 18 |
| 26.18 ± 0.20 | 3.405 | 27 |
| 27.42 ± 0.20 | 3.252 | 12 |
| 28.29 ± 0.20 | 3.155 | 11 |
| 29.22 ± 0.20 | 3.056 | 13 |

Table 12 provides XRPD data identified as "Prominent Peaks". Prominent peaks are a subset of the entire observed peak list. Prominent peaks are selected from observed peaks by identifying preferably non-overlapping, low-angle peaks, with strong intensity.

TABLE 12

Prominent Peaks for Crystalline Form B

| Diffraction angle °2θ (deg) | d space (Å) | Intensity (%) |
|---|---|---|
| 9.01 ± 0.20 | 9.819 | 18 |
| 10.32 ± 0.20 | 8.571 | 14 |
| 11.70 ± 0.20 | 7.561 | 13 |
| 12.67 ± 0.20 | 6.985 | 15 |
| 13.26 ± 0.20 | 6.676 | 21 |
| 15.96 ± 0.20 | 5.55 | 76 |
| 17.55 ± 0.20 | 5.053 | 100 |
| 21.26 ± 0.20 | 4.18 | 38 |
| 21.88 ± 0.20 | 4.062 | 17 |
| 22.61 ± 0.20 | 3.933 | 16 |
| 24.55 ± 0.20 | 3.627 | 44 |
| 26.18 ± 0.20 | 3.405 | 27 |

Although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the invention.

What is claimed is:

1. A crystalline form of a compound of Formula (I):

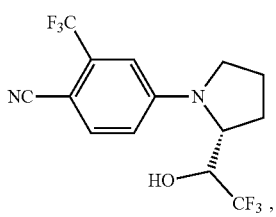

or a solvate thereof,
wherein the crystalline form exhibits an X-ray powder diffraction pattern comprising at least one characteristic peak, wherein said characteristic peak is selected from the group consisting of approximately 8.5, 11.8, 12.4, 13.3, 13.7, 15.0, 17.1, 17.5, 18.2, 18.5, 19.5, 21.1, 21.7, 22.1, 26.6, 23.1, 23.7, 24.8, 25.0, 25.5, 26.2, 27.5, and 29.6 degrees 2θ.

2. The crystalline form of claim 1, wherein the crystalline form exhibits an X-ray powder diffraction pattern comprising at least three characteristic peaks, wherein said characteristic peaks are selected from the group consisting of 8.5, 13.3, 13.7, 15.0, 17.5, 18.2, 18.5, 19.5, 21.1, 23.1, 23.7, 25.5, and 26.2 degrees 2θ.

3. The crystalline form of claim 1, wherein the crystalline form has a melting point of about 163° C.

4. A crystalline form of a compound of Formula (I):

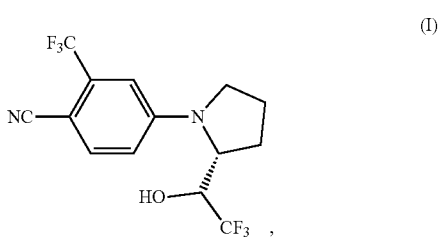

or a solvate thereof,
wherein the crystalline form exhibits an X-ray powder diffraction pattern comprising at least one characteristic peak, wherein said characteristic peak is selected from the group consisting of approximately 9.6, 11.7, 13.0, 13.9, 14.2, 15.2, 15.8, 17.5, 19.1, 19.4, 21.2, 21.9, 22.6, 23.3, 23.6, 24.7, 25.3, 25.6, 25.9, 26.9, 28.1, and 29.0 degrees 2θ.

5. The crystalline form of claim 4, wherein the crystalline form exhibits an X-ray powder diffraction pattern comprising at least three characteristic peaks, wherein said characteristic peaks are selected from the group consisting of 9.6, 11.7, 13.0, 13.9, 15.8, 17.5, 19.1, 19.4, 21.2, 21.9, 22.6, 23.3, 23.6, 25.3, and 25.6 degrees 2θ.

6. The crystalline form of claim 4, wherein the crystalline form has a melting point of about 162° C.

7. A crystalline form of a compound of Formula (I):

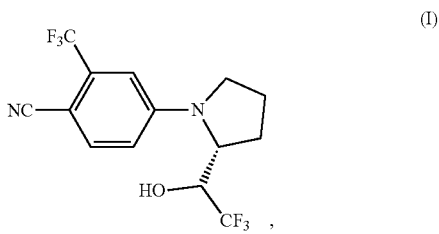 [SMILES: N#Cc1ccc(N2CCC[C@@H]2C(O)C(F)(F)F)cc1C(F)(F)F]

or a solvate thereof,
wherein the crystalline form exhibits an X-ray powder diffraction pattern comprising at least one characteristic peak, wherein said characteristic peak is selected from the group consisting of approximately 9.0, 10.3, 11.7, 12.7, 13.3, 14.0, 14.8, 16.0, 17.1, 17.6, 19.2, 19.8, 21.3, 21.9, 22.6, 23.4, 23.7, 24.6, 25.4, 25.7, 26.2, 27.4, 28.3, and 29.2 degrees 2θ.

8. The crystalline form of claim 7, wherein the crystalline form exhibits an X-ray powder diffraction pattern comprising at least three characteristic peaks, wherein said characteristic peaks are selected from the group consisting of 9.0, 10.3, 11.7, 12.7, 13.3, 16.0, 17.6, 21.3, 21.9, 22.6, 24.6, and 26.2 degrees 2θ.

9. The crystalline form of claim 7, wherein the crystalline form has a melting point of about 162° C.

10. The crystalline form of claim 1, wherein the crystalline form is unsolvated.

11. A composition comprising the crystalline form of claim 1, wherein the total weight of the compound of Formula (I) in the composition comprises greater than 80% by weight of the crystalline form.

12. The composition of claim 11, wherein the crystalline form is crystalline Form C.

13. A method of treating a disease or disorder comprising administering to a subject a therapeutically effective amount of a composition comprising the crystalline form of claim 1, wherein the disease or disorder is selected from the group consisting of: aging skin; Alzheimer's disease; anemias; anorexia; arthritis; arteriosclerosis; atherosclerosis; bone disease; distraction osteogenesis; reduced bone mass, density or growth; bone weakening; musculoskeletal impairment; cachexia; cancer; cardiac dysfunction; catabolic side effects of glucocorticoids; Crohn's disease; growth retardation in connection with Crohn's disease; short bowel syndrome; irritable bowel syndrome; inflammatory bowel disease; ulcerative colitis; cognitive decline and impairment; dementia; short term memory loss; contraception (male and female); chronic obstructive pulmonary disease (COPD); chronic bronchitis; decreased pulmonary function; emphysema; decreased libido in both men and women; depression; nervousness, irritability and/or stress; reduced mental energy and low self-esteem; dyslipidemia; erectile dysfunction; frailty; age-related functional decline ("ARFD") in the elderly; growth hormone deficiency; hematopoietic disorders; hormone replacement (male and female); hyper-cholesterolemia; hyperinsulinemia; hyperlipidemia; hypertension; hyperandrogenemia; hypogonadism; hypothermia; impotence; insulin resistance; type 2 diabetes; lipodystrophy; male menopause; metabolic syndrome (syndrome X); loss of muscle strength and/or function; muscular dystrophies; muscle loss following surgery; muscular atrophy; neurodegenerative diseases; neuromuscular disease; decreased platelet count; platelet aggregation disorders; obesity; osteoporosis; osteopenia; glucocorticoid-induced osteoporosis; osteochondro-dysplasias; periodontal disease; premenstrual syndrome; postmenopausal symptoms in women; Reaven's syndrome; rheumatological disease; sarcopenia; male and female sexual dysfunction; physiological short stature; tooth damage; thrombocytopenia; vaginal dryness; atrophic vaginitis; ventricular dysfunction; and wasting.

14. The process of claim 13, wherein the disease or disorder is selected from the group consisting of: loss of muscle strength and/or function; muscular dystrophies; muscle loss following surgery; and muscular atrophy.

15. A composition comprising a crystalline form of claim 4, wherein the total weight of the compound of Formula (I) in the composition comprises greater than 80% by weight of the crystalline form.

16. The composition of claim 15, wherein the crystalline form is crystalline Form E.

17. A method of treating a disease or disorder comprising administering to a subject a therapeutically effective amount of a composition comprising the crystalline form of claim 4, wherein the disease or disorder is selected from the group consisting of: aging skin; Alzheimer's disease; anemias; anorexia; arthritis; arteriosclerosis; atherosclerosis; bone disease; distraction osteogenesis; reduced bone mass, density or growth; bone weakening; musculoskeletal impairment; cachexia; cancer; cardiac dysfunction; catabolic side effects of glucocorticoids; Crohn's disease; growth retardation in connection with Crohn's disease; short bowel syndrome; irritable bowel syndrome; inflammatory bowel disease; ulcerative colitis; cognitive decline and impairment; dementia; short term memory loss; contraception (male and female); chronic obstructive pulmonary disease (COPD); chronic bronchitis; decreased pulmonary function; emphysema; decreased libido in both men and women; depression; nervousness, irritability and/or stress; reduced mental energy and low self-esteem; dyslipidemia; erectile dysfunction; frailty; age-related functional decline ("ARFD") in the elderly; growth hormone deficiency; hematopoietic disorders; hormone replacement (male and female); hyper-cholesterolemia; hyperinsulinemia; hyperlipidemia; hypertension; hyperandrogenemia; hypogonadism; hypothermia; impotence; insulin resistance; type 2 diabetes; lipodystrophy; male menopause; metabolic syndrome (syndrome X); loss of muscle strength and/or function; muscular dystrophies; muscle loss following surgery; muscular atrophy; neurodegenerative diseases; neuromuscular disease; decreased platelet count; platelet aggregation disorders; obesity; osteoporosis; osteopenia; glucocorticoid-induced osteoporosis; osteochondro-dysplasias; periodontal disease; premenstrual syndrome; postmenopausal symptoms in women; Reaven's syndrome; rheumatological disease; sarcopenia; male and female sexual dysfunction; physiological short stature; tooth damage; thrombocytopenia; vaginal dryness; atrophic vaginitis; ventricular dysfunction; and wasting.

18. The process of claim 17, wherein the disease or disorder is selected from the group consisting of: loss of muscle strength and/or function; muscular dystrophies; muscle loss following surgery; and muscular atrophy.

19. A composition comprising a crystalline form of claim 7, wherein the total weight of the compound of Formula (I) in the composition comprises greater than 80% by weight of the crystalline form.

20. The composition of claim 19, wherein the crystalline form is crystalline Form B.

21. A method of treating a disease or disorder comprising administering to a subject a therapeutically effective amount of a composition comprising the crystalline form of claim 7, wherein the disease or disorder is selected from the group consisting of: aging skin; Alzheimer's disease; anemias; anorexia; arthritis; arteriosclerosis; atherosclerosis; bone disease; distraction osteogenesis; reduced bone mass, density or growth; bone weakening; musculoskeletal impairment; cachexia; cancer; cardiac dysfunction; catabolic side effects of glucocorticoids; Crohn's disease; growth retardation in connection with Crohn's disease; short bowel syndrome; irritable bowel syndrome; inflammatory bowel disease; ulcerative colitis; cognitive decline and impairment; dementia; short term memory loss; contraception (male and female); chronic obstructive pulmonary disease (COPD); chronic bronchitis; decreased pulmonary function; emphysema; decreased libido in both men and women; depression; nervousness, irritability and/or stress; reduced mental energy and low self-esteem; dyslipidemia; erectile dysfunction; frailty; age-related functional decline ("ARFD") in the elderly; growth hormone deficiency; hematopoietic disorders; hormone replacement (male and female); hyper-cholesterolemia; hyperinsulinemia; hyperlipidemia; hypertension; hyperandrogenemia; hypogonadism; hypothermia; impotence; insulin resistance; type 2 diabetes; lipodystrophy; male menopause; metabolic syndrome (syndrome X); loss of muscle strength and/or function; muscular dystrophies; muscle loss following surgery; muscular atrophy;

neurodegenerative diseases; neuromuscular disease; decreased platelet count; platelet aggregation disorders; obesity; osteoporosis; osteopenia; glucocorticoid-induced osteoporosis; osteochondro-dysplasias; periodontal disease; premenstrual syndrome; postmenopausal symptoms in women; Reaven's syndrome; rheumatological disease; sarcopenia; male and female sexual dysfunction; physiological short stature; tooth damage; thrombocytopenia; vaginal dryness; atrophic vaginitis; ventricular dysfunction; and wasting.

22. The method of claim 21, wherein the disease or disorder is selected from the group consisting of: loss of muscle strength and/or function; muscular dystrophies; muscle loss following surgery; and muscular atrophy.

\* \* \* \* \*